United States Patent
Dimopoulos et al.

(10) Patent No.: US 8,822,455 B2
(45) Date of Patent: Sep. 2, 2014

(54) FUSED AMINODIHYDROTHIAZINE DERIVATIVES

(75) Inventors: Paschalis Dimopoulos, Hatfield Hertfordshire (GB); Adrian Hall, Hatfield Hertfordshire (GB); Yoichi Kita, Tsukuba (JP); Andrew Madin, Hatfield Hertfordshire (GB); Nicola Louise Shuker, Hatfield Hertfordshire (GB)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/978,062

(22) PCT Filed: Jan. 5, 2012

(86) PCT No.: PCT/EP2012/050122
§ 371 (c)(1),
(2), (4) Date: Sep. 18, 2013

(87) PCT Pub. No.: WO2012/093148
PCT Pub. Date: Jul. 12, 2012

(65) Prior Publication Data
US 2014/0011802 A1  Jan. 9, 2014

(30) Foreign Application Priority Data
Jan. 6, 2011 (GB) ................................. 1100181.5

(51) Int. Cl.
C07D 513/14  (2006.01)
A61K 31/542  (2006.01)

(52) U.S. Cl.
USPC .......................................... 514/224.2; 544/48

(58) Field of Classification Search
CPC .............................. C07D 513/14; A61K 31/542
USPC ........................................ 544/48; 514/224.2
See application file for complete search history.

(56) References Cited

U.S. PATENT DOCUMENTS

| | | | |
|---|---|---|---|
| 3,227,713 A | 1/1966 | Behner et al. | |
| 3,235,551 A | 2/1966 | Schubert et al. | |
| 6,642,237 B1 | 11/2003 | Tata et al. | |
| 7,189,715 B2 | 3/2007 | Jerussi et al. | |
| 7,648,983 B2 | 1/2010 | Audia et al. | |
| 8,158,620 B2 | 4/2012 | Suzuki et al. | |
| 8,198,269 B2 | 6/2012 | Motoki et al. | |
| 8,278,441 B2 * | 10/2012 | Mergott et al. | 544/48 |
| 8,338,407 B2 | 12/2012 | Hall et al. | |
| 8,426,584 B2 | 4/2013 | Mitasev et al. | |
| 8,501,733 B2 | 8/2013 | Motoki et al. | |
| 8,592,408 B2 | 11/2013 | Hall et al. | |
| 2004/0110743 A1 | 6/2004 | Miyamato et al. | |
| 2006/0052406 A1 | 3/2006 | Fisher et al. | |
| 2006/0111370 A1 | 5/2006 | Zhu et al. | |
| 2007/0021454 A1 | 1/2007 | Coburn et al. | |
| 2007/0287692 A1 | 12/2007 | Wu et al. | |
| 2008/0139538 A1 | 6/2008 | McGaughey et al. | |
| 2008/0200445 A1 | 8/2008 | Zhu et al. | |
| 2009/0082560 A1 | 3/2009 | Kobayashi et al. | |
| 2009/0209755 A1 | 8/2009 | Suzuki et al. | |
| 2010/0075957 A1 | 3/2010 | Tamura et al. | |
| 2010/0093999 A1 | 4/2010 | Motoki et al. | |
| 2010/0160290 A1 | 6/2010 | Kobayashi et al. | |
| 2010/0317850 A1 | 12/2010 | Suzuki et al. | |
| 2011/0009395 A1 | 1/2011 | Audia et al. | |
| 2011/0152253 A1 | 6/2011 | Motoki et al. | |

(Continued)

FOREIGN PATENT DOCUMENTS

| | | |
|---|---|---|
| EP | 1 942 105 | 7/2008 |
| EP | 2 233 474 | 9/2010 |

(Continued)

OTHER PUBLICATIONS

International Search Report and Written Opinion in International Application No. PCT/EP2012/050122, mailed Mar. 6, 2012, 15 pages.
International Preliminary Report in International Application No. PCT/EP2012/050122, mailed Jul. 18, 2013, 12 pages.
Abdel-Magid et al., "Reductive Amination of Aldehydes and Ketones with Sodium Triacetoxyborohydride. Studies on Direct and Indirect Reductive Amination Procedures," *J. Org. Chem.*, 61(11):3849-3862 (1996).

(Continued)

*Primary Examiner* — Kahsay Habte
(74) *Attorney, Agent, or Firm* — Fish & Richardson P.C.

(57) ABSTRACT

The present invention relates to a fused aminodihydrothiazine derivative of formula (I):

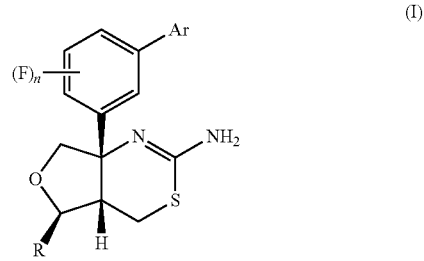

wherein
R is hydrogen or $C_{1-6}$alkyl, optionally substituted by one to five halogen atoms;
n is 0, 1, 2 or 3;
Ar is phenyl or a 5- or 6-membered heteroaromatic group containing 1, 2 or 3 N atoms, which Ar is optionally substituted by one to three substituents selected from hal, hydroxyl, —CN, $C_{1-6}$alkyl, $C_{2-3}$alkenyl, $C_{2-3}$alkynyl, $C_{1-6}$alkoxy, $C_{3-6}$cycloalkoxy and pyrazine, where $C_{1-6}$alkyl and $C_{1-6}$alkoxy are optionally substituted by one to three halogen atoms;
and pharmaceutically acceptable salts thereof;
which compound has an Aβ production inhibitory effect or a BACE1 inhibitory effect and is useful as a prophylactic or therapeutic agent for a neurodegenerative disease caused by Aβ and typified by Alzheimer-type dementia.

13 Claims, No Drawings

(56) References Cited

U.S. PATENT DOCUMENTS

| | | |
|---|---|---|
| 2011/0207723 A1 | 8/2011 | Motoki et al. |
| 2012/0094984 A1 | 4/2012 | Suzuki et al. |
| 2012/0190672 A1 | 7/2012 | Hall et al. |
| 2012/0190848 A1 | 7/2012 | Mitasev et al. |
| 2012/0202804 A1 | 8/2012 | Ellard et al. |
| 2012/0202828 A1 | 8/2012 | Castro Pineiro et al. |
| 2013/0197244 A1 | 8/2013 | Mitasev et al. |
| 2013/0203740 A1 | 8/2013 | Hall et al. |
| 2013/0203741 A1 | 8/2013 | Suzuki et al. |

FOREIGN PATENT DOCUMENTS

| | | |
|---|---|---|
| JP | 09-067355 | 3/1997 |
| JP | 2004-149429 | 5/2004 |
| WO | WO 01/87293 | 11/2001 |
| WO | WO 02/096897 | 12/2002 |
| WO | WO 2004/014843 | 2/2004 |
| WO | WO 2004/043916 | 5/2004 |
| WO | WO 2005/058311 | 6/2005 |
| WO | WO 2005/097767 | 10/2005 |
| WO | WO 2006/041404 | 4/2006 |
| WO | WO 2006/041405 | 4/2006 |
| WO | WO 2006/059234 | 6/2006 |
| WO | WO 2006/138264 | 12/2006 |
| WO | WO 2007/011810 | 1/2007 |
| WO | WO 2007/049532 | 5/2007 |
| WO | WO 2007/114771 | 10/2007 |
| WO | WO 2007/139230 | 12/2007 |
| WO | WO 2008/073365 | 6/2008 |
| WO | WO 2008/133273 | 11/2008 |
| WO | WO 2008/133274 | 11/2008 |
| WO | WO 2009/067081 | 5/2009 |
| WO | WO 2009/091016 | 7/2009 |
| WO | WO 2009/131974 | 10/2009 |
| WO | WO 2009/134617 | 11/2009 |
| WO | WO 2009/151098 | 12/2009 |
| WO | WO 2010/013302 | 2/2010 |
| WO | WO 2010/013794 | 2/2010 |
| WO | WO 2010/021680 | 2/2010 |
| WO | WO 2010/038686 | 4/2010 |
| WO | WO 2010/105179 | 9/2010 |
| WO | WO 2011/005738 | 1/2011 |
| WO | WO 2011/009897 | 1/2011 |
| WO | WO 2011/009898 | 1/2011 |
| WO | WO 2012/003274 | 1/2012 |
| WO | WO 2012/093148 | 7/2012 |
| WO | WO 2012/098461 | 7/2012 |
| WO | WO 2012/100179 | 7/2012 |

OTHER PUBLICATIONS

Agarwal et al., "Pyridinium chlorochromate. An improved method for its synthesis and use of anhydrous acetic acid as catalyst for oxidation reactions," Tetrahedron, 1990, 46:4417-4420.

Ames et al., "Methods for detecting carcinogens and mutagens with the *Salmonella*/mammalian -microsome mutagenicity test," *Mutat. Res.*, 31:347-364 (1975).

Aranyos et al., "Novel Electron-Rich Bulky Phosphine Ligands Facilitate the Palladium-Catalyzed Preparation of Diaryl Ethers," *J Am Chem Soc.*, 121(18):4369-4378 (1999).

Arnone et al., An Enantiospecific Entry to Fluoro Substituted Aminocyclopentanols through Intramolecular Nitrile Oxide, Nitrone, and Oxime Cycloaddition Reactions, *Tetrahedron: Asymmetry* 5(6):1019-1028 (1994).

Aschwanden et al., "Reduction of 2,3-dihydroisoxazoles to beta-amino ketones and beta-amino alcohols," *Org. Lett.*, 7(25):5741-5742 (2005).

Barange et al., "A Remarkable Accelerating Effect of Ag-Salt on Intramolecular Cyclization of o-(1-Alkynyl)benzenesulfonamides," *J. Org. Chem.*, 72(22):8547-8550 (2007).

Barlow et al., "Intervalence Transitions in the Mixed-Valence Monocations of Bis(triarylamines) Linked with Vinylene and Phenylene—Vinylene Bridges," *J. Am. Chem. Soc.*, 127(48):16900-16911 (2005).

Bennua-Shalmowski and Vorbruggen, "A facile conversion of primary or secondary alcohols with n-perfluorobutane-sulfonyl fluoride/1,8-diazabicyclo[5.4.0]undec-7-ene into their corresponding fluorides," Tetrahedron Lett., 1995, 36:2611-2614.

Berge et al., "Pharmaceutical salts," *J. Pharm. Sci.*, 66:1-19 (1977).

Bobrov et al., "Interaction of Quinone Oxide with Thiourea" *Chemistry and Chemical Technology*, 33(10):15-18 (1990) (original and English language translation).

Boeckman et al., "The Dess-Martin Periodinane: 1,1,1 -Triacetoxy-1,1 -Dihydro-1,2-Benziodoxo1-3(1H)-One," Org. Synth. Coll., 2004, 10:696, 6 pages.

Brzostwska et al., "Chiral Prodyes: Synthesis and Full Characterization of (S)-1-Phenylethylamides of the Optically Active Q-Methyldihydrofluoresceins," *Heterocycles*, 32(10):1968-1972 (1991).

Butler et al., "A Facile Synthesis of New 5H-Indazolo[3,2-b]benzo[d]-1,3-oxazines via One-Pot Intramolecular Bisheterocyclizations," *J. Org. Chem.*, 73(1):234-240 (2008).

Chakrabarty et al., "DBU, a highly efficient reagent for the facile regeneration of (hetero)arylamines from their acetamides and benzamides: influence of solvent, temperature, and microwave irradiation," *Synth. Commun.*, 32(2):265-272 (2002).

Coates et al., "Annelative ring expansion via intramolecular [2 + 2] photocycloaddition of .alpha.,.beta.-unsaturated .gamma.-lactones and reductive cleavage: synthesis of hydrocyclopentacyclooctene-5-carboxylates," *J Org. Chem.*, 47(19):3597-3607 (1982).

Cohen et al., "Synthesis of 2-Amino-5,6-dihydro-4H-1,3-thiazines and Related Compounds by Acid Catalyzed Cyclization of Allylic Isothiuronium Salts," *Journal of Heterocyclic Chemistry*, 14:717-723 (1977).

Corey and Kim, "New and highly effective method for the oxidation of primary and secondary alcohols to carbonyl compounds," J. Am. Chem. Soc., 1972, 94(21):7586-7587.

Corey and Suggs, "Pyridinium Chlorochromate. An efficient reagent for oxidation of primary and secondary alcohols to carbonyl compounds," Tetrahedron Lett., 1975, 16, 2647-2650.

Crisp and Meyer, "Palladium-catalyzed, carbonylative, intramolecular coupling of hydroxyvinyl triflates. Synthesis of substituted .alpha.,.beta.-butenolides," *J. Org. Chem.*, 57(25):6972-6975 (1992).

Cross et al., International Union of Pure and Applied Chemistry (IUPAC) Rules for the Nomenclature of Organic Chemistry, Section E, Stereochemistry, *Pure & Applied Chemistry*, 45:11-30 (1976).

Danheiser et al., "An annulation method for the synthesis of highly substituted polycyclic aromatic and heteroaromatic compounds," *J Am. Chem. Soc.*, 112(8):3093-3100 (1990).

Darses et al., "Palladium-catalyzed cross-coupling reactions of arenediazonium tetrafluoroborates with aryl- and alkenylboronic acids," Bulletin de la Societe Chimique de France 1996, 133(11), 1095-1102.

De Lucca et al., "Discovery and Structure—Activity Relationship of N-(Ureidoalkyl)-Benzyl-Piperidines as Potent Small Molecule CC Chemokine Receptor-3 (CCR3) Antagonists," *J Med. Chem.*, 45(17)3794-3804 (2002).

Dess and Martin, "Readily accessible 12-I-5 oxidant for the conversion of primary and secondary alcohols to aldehydes and ketones," J. Org. Chem. 1983, 48:4155-4156.

Dorwald, F.A., Side Reactions in Organic Synthesis, 2005, Wiley: VCH, Weinheim, p. IX, 15 pages.

Edwards et al., "Application of Fragment-Based Lead Generation to the Discovery of Novel, Cyclic Amidine β-Secretase Inhibitors with Nanomolar Potency, Cellular Activity, and High Ligand Efficiency," *J. Med. Chem.*, 50(24):5912-5925 (2007).

Fang et al., "Synthesis, Antibacterial, and Cytotoxic Evaluation of Certain 7-Substituted Norfloxacin Derivatives," *J. Med. Chem.*, 43(20):3809-3812 (2000).

Farina and Krishnamurthy, "The Stille Reaction," J Org. React. 1998, 50, 1-652.

Forman et al., "Differential Effects of the Swedish Mutant Amyloid Precursor Protein on β-Amyloid Accumulation and Secretion in Neurons and Nonneuronal Cells," *The Journal of Biological Chemistry*, 272(51):32247-32253 (1997).

(56) References Cited

OTHER PUBLICATIONS

Fuller et al., "Succinct Synthesis of β-Amino Acids via Chiral Isoxazolin," *J. Am. Chem. Soc.*, 127(15):5376-5383 (2005).
Fuller et al., "Synthesis and Structural Characteristics of Geminally Disubstituted β-Amino Acids," *Synlett.*, 8:1409-1413 (2004).
Fulop et al., "Synthesis of Stereoisomers 2-Phenylimino-3,1-Perhydro-Benzoxazines and 3, 1-Perhydrobenzothiazines," *Org Prep Proced Int'l*, 20:73-82 (1988).
Glenner et al., "Alzheimer's Disease: Initial report of the purification and characterization of a novel cerebrovascular amyloid protein," *Biochemical and Biophysical Research Communications*, 120(3):885-890 (1984).
Gloor et al., "Molecular and cellular permeability control at the blood-brain barrier," *Brain Res. Rev.*, 36:258-264 (2001).
Gong et al., "Alzheimer's disease-affected brain: Presence of oligomeric Aβ ligands (ADDLs) suggests a molecular basis for reversible memory loss," *Proceeding National Academy of Science USA*, 100(18):10417-10422 (2003).
Gouras et al., "Intraneuronal Aβ42 Accumulation in Human Brain," *American Journal of Pathology*, 156(1):15-20 (2000).
Green et al., "Mutagen testing using TRP+ reversion in *Escherichia coli*," *Mutat. Res.*, 38:3-32 (1976).
Greene and Wuts, "Protective Groups in Organic Chemistry, Second Edition", *John Wiley & Sons* p. 327-330 (1991).
Greene and Wuts, "Protective Groups in Organic Chemistry, Third Edition", *John Wiley & Sons*, p. 17-245 (1999).
Greene and Wuts, "Protective Groups in Organic Chemistry, Third Edition", *John Wiley & Sons*, p. 293-329 (1999).
Greene and Wuts, "Protective Groups in Organic Chemistry, Third Edition", *John Wiley & Sons*, p. 494-572 (1999).
Greene and Wuts, "Protective Groups in Organic Chemistry, Third Edition", *John Wiley & Sons*, p. 506-507 (1999).
Greene and Wuts, "Protective Groups in Organic Chemistry, Third Edition", *John Wiley & Sons*, p. 531-537 (1999).
Greene and Wuts, "Protective Groups in Organic Chemistry, Third Edition", *John Wiley & Sons*, p. 642-643 (1999).
Greene et al., "Protective Groups in Organic Chemistry, Third Edition," *John Wiley & Sons*, 404-408 (1999).
Greene et al., "Protective Groups in Organic Chemistry, Third Edition," *John Wiley & Sons*, 518-525 (1999).
Greene and Wuts "Protective Groups in Organic Chemistry, Third Edition", *John Wiley & Sons* p. 102-104 (1999).
Gu et al., "Facile One-Pot Synthesis of 6-Monosubstituted and 6,12-Disubstituted 5,11-Dihydroindolo[3,2-b]carbazoles and Preparation of Various Functionalized Derivatives," J. Org. Chem., 72(19):7207-7213 (2007).
Hall et al., "Comparative pharmacokinetic-pharmacodynamic responses in rat and cynomolgus monkey for a novel BACE inhibitor ER-901356," *11th Int'l Conf on Alzheimer's & Parkinson's Diseases (AD/PD 2013)*, 4 pages, (Mar. 6-10, 2013).
Han et al., "Diverse Synthesis of Novel Bisterpyridines via Suzuki-Type Cross-Coupling," *Org. Lett.*, 9(4):559-562 (2007).
Hassner et al. "Stereochemistry. 82. Conformation of fused five-membered heterocyclic rings derived from the intramolecular oxime olefin cycloaddition reaction," *J Org. Chem.*, 58(17):4539-4546 (1993).
Hassner, "Interamolecular Oxime Olefin Cycloadditions. Stereospecific Formation of Functionalized Pyrrolidines," *Tetrahedron Letters*, 29 (41):5313-5316 (1988).
He et al., "Utility of unbound plasma drug levels and P-glycoprotein transport data in prediction of central nervous system exposure," *Xenobiotica*, 39:687-693 (2009).
Heany et al., "The influence of oxime stereochemistry in the generation of nitrones from omega-alkenyloximes by cyclization or 1,2-prototropy," *J Chem. Soc., Perkin Trans.*, 1:341-349 (Jan. 1, 1998).
Hitchcock et al., "Structure-brain exposure relationships," *J. Med. Chem.*, 49:7559-7583 (2006).
Hock et al., "Antibodies against β-Amyloid Slow Cognitive Decline in Alzheimer's Disease," *Neuron*, 38:547-554 (2003).
Howbert et al., "Novel agents effective against solid tumors: the diarylsulfonylureas. Synthesis, activities, and analysis of quantitative structure-activity relationships," *J Med. Chem.*, 33:2393-2407 (1990).
Hussain et al., "Oral administration of a potent and selective non-peptidic BACE-1 inhibitor decreases beta-cleavage of amyloid precursor protein and amyloid-beta production in vivo," *J. Neurochem.*, 100:802-809 (2007).
Iserloh et al., "Discovery of an orally efficaceous 4-phenoxypyrrolidine-based BACE-1 inhibitor," *Bioorg. Med. Chem. Lett.*, 18:418-422 (2008).
Ishikawa et al., "Synthesis of A-Ring Fragments of 1α,25-Dihydroxyvitamin $D_3$ and Taxane Diterpenoids: Effective Construction of Conjugated Formylcyclohexene Frameworks from Isoxazolines," *Tetrahedron*, 54(22):5869-5882 (1998).
Ishiyama et al., "Palladium(0)-Catalyzed Cross-Coupling Reaction of Alkoxydiboron with Haloarenes: A Direct Procedure for Arylboronic Esters," J. Org. Chem. 1995, 60(23):7508-7510.
Iwata et al., "Radiosynthesis of O-[$^{11}$C]methyl-L-tyrosine and O-[$^{18}$F]Fluoromethyl-L-tyrosine as potential PET tracers for imaging amino acid transport," *J Labelled Compounds & Radiopharmaceuticals*, 46(6):555-566 (2003).
Jarrett et al., "The Carboxy Terminus of the β Amyloid Protein is Critical for the Seeding of Amyloid Formation: Implications for the Pathogenesis of Alzheimer's Disease," *Biochemistry*, 32(18):4693-4697 (1993).
Ji et al., "Synthesis and Structure—Activity Relationship Studies of 3,6-Diazabicyclo[3.2.0]heptanes as Novel α4β2 Nicotinic Acetylcholine Receptor Selective Agonists," *J Med. Chem.*, 50(22):5493-5508 (2007).
Kalvass et al., "Influence of nonspecific brain and plasma binding on CNS exposure: implications for rational drug discovery," *Biopharm. Drug Dispos.*, 23:327-338 (2002).
Katagiri et al., "Synthesis of Chiral Spiro 3-Oxazolin-5-one 3-Oxides (Chiral Nitrones) via a Nitrosoketene Intermediate and Their Asymmetric 1,3-Dipolar Cycloaddition Reactions Leading to the EPC Synthesis of Modified Amino Acids," *Tetrahedron*, 53(16):5725-5746 (1997).
Kearney et al., "Solid-Phase Synthesis of 2-Aminothiazoles," *J Org. Chem.*, 63(1):196-200 (1998).
King et al., "Highly general stereo-, regio-, and chemo-selective synthesis of terminal and internal conjugated enynes by the Pd-catalysed reaction of alkynylzinc reagents with alkenyl halides," J. Chem. Soc., Chem. Commun., 1977, 683-684.
Knauer and Kunz, "Palladium-catalysed C—C coupling reactions in the enantioselective synthesis of 2,4-disubstituted 4,5-dehydropiperidines using galactosylamine as a stereodifferentiating auxiliary," *Tetrahedron: Asymmetry*, 16(2):529-539 (2005).
Kuo et al., "A Synthesis of Estrone via Novel Intermediates, Mechanism of the Coupling Reaction of a Vinyl Carbinol with a β Diketone," *Journal of Organic Chemistry*, 33(8):3126-3132 (1968).
Kusuhara et al., "Efflux transport systems for drugs at the blood-brain barrier and blood-cerebrospinal fluid barrier (Part 1)," *Drug Discov. Today*, 6:150-156 (2001).
Kwong et al., "Copper-Catalyzed Coupling of Alkylamines and Aryl Iodides: An Efficient System Even in an Air Atmosphere," *Org. Lett.*, 4(4):581-584 (2002).
L'Heureux et al., "Aminodifluorosulfinium Salts: Selective Fluorination Reagents with Enhanced Thermal Stability and Ease of Handling," J. Org. Chem., 2010, 75:3401-3411.
Lal et al., "Bis(2-methoxyethyl)aminosulfur trifluoride: a new broad-spectrum deoxofluorinating agent with enhanced thermal stability," Chem. Commun. 1999, 215-216.
Lal et al., "Bis(2-methoxyethyl)aminosulfur Trifluoride: A New Broad-Spectrum Deoxofluorinating Agent with Enhanced Thermal Stability," J. Org. Chem. 1999, 64:7048-7054.
Leroux et al., "Trifluoromethoxy Substituted Anilines: Metalation as the Key Step for Structural Elaboration," *J. Org. Chem.*, 68(12):4693-4699 (2003).
Ley et al., "Tetrapropylammonium Perruthenate, Pr4N+RuO4-, TPAP: A Catalytic Oxidant for Organic Synthesis," Synthesis, 1994, 639-666.

(56) References Cited

OTHER PUBLICATIONS

Lin et al., "Role of P-glycoprotein in pharmacokinetics: clinical implications," Clin. Pharmacokinet., 42:59-98 (2003).
Lin, "How significant is the role of P-glycoprotein in drug absorption and brain uptake?," Drugs of Today, 40:5-22 (2004).
Littke et al., "Versatile Catalysts for the Suzuki Cross-Coupling of Arylboronic Acids with Aryl and Vinyl Halides and Triflates under Mild Conditions," J. Am. Chem. Soc., 122(17):4020-4028 (2000).
Liu et al., "A practical and chemoselective reduction of nitroarenes to anilines using activated iron," Adv. Synth. Caral., 347:217-219 (2005).
Mahar et al., "Passive permeability and P-glycoprotein-mediated efflux differentiate central nervous system (CNS) and non-CNS marketed drugs," J. Pharmacol. Exp. Ther., 303:1029-1037 (2002).
Malamas et al., "Design and synthesis of aminohydantoins as potent and selective human $\beta$- secretase (BACE1) inhibitors with enhanced brain permeability," Bioorg. Med. Chem. Lett., 20:6597-6605 (2010).
Mancuso and Swern, "Activated dimethyl sulfoxide: Useful reagents for synthesis," Synthesis, 1981, 3:165-185.
Martin et al., "Simple and Efficient Preparation of Ketones from Morpholine Amides," Synlett, 1997, 12:1414-1416.
Masters et al., "Amyloid plaque core protein in Alzheimer disease and Down syndrome," Proceeding National Academy of Science USA, 82:4245-4249 (1985).
Matassa et al., "Synthesis and in vitro LTD4 antagonist activity of bicyclic and monocyclic cyclopentylurethane and cyclopentylacetamide N-arylsulfonyl amides," J Med. Chem., 33(9):2621-2629 (1990).
Maurer, "Relationship between exposure and nonspecific binding of thirty-three central nervous system drugs in mice," Drug Metab. Dispos., 33:175-181 (2005).
McCann et al., "Detection of carcinogens as mutagens in the Salmonella/microsome test: assay of 300 chemicals," Proc. Natl. Acad. Sci. USA., 72:5135-5139 (1975).
McCann et al., "Detection of carcinogens as mutagens in the Salmonella/microsome test: assay of 300 chemicals: discussion," Proc. Natl. Acad. Sci. USA, 73:950-954 (1976).
Meredith et al., "P-Glycoprotein Efflux and Other Factors Limit Brain Amyloid $\beta$ Reduction by 62 -Site Amyloid Precursor Protein-Cleaving Enzyme 1 Inhibitors in Mice," J. Pharmacol. Exp. Ther, 326(2):502-513 (2008).
Middleton, "New fluorinating reagents. Dialkylaminosulfur fluorides," J. Org. Chem. 1975, 40:574-578.
Milstein and Stille, "A general, selective, and facile method for ketone synthesis from acid chlorides and organotin compounds catalyzed by palladium," J. Am. Chem. Soc. 1978, 100:3636-3638.
Miyaura and Suzuki, "Palladium-Catalyzed Cross-Coupling Reactions of Organoboron Compounds," Chem. Rev., 1995, 95(7):2457-2483.
Murata et al., "Novel Palladium(0)-Catalyzed Coupling Reaction of Dialkoxyborane with Aryl Halides: Convenient Synthetic Route to Arylboronates," J. Org. Chem. 1997, 62(19):6458-6459.
Nahm et al., N-Methoxy-N-Methylamides as Effective Acylating Agents, Tetrahedron Lett., 22(39):3815-3818 (1981).
Nerdinger et al., "Combined Directed ortho Metalation/Suzuki—Miyaura Cross-Coupling Strategies. Regiospecific Synthesis of Chlorodihydroxybiphenyls and Polychlorinated Biphenyls," J Org. Chem., 72(16):5960-5967 (2007).
Nussbaumer et al., "Highly selective TFAA-cleavage of tertiary 2,4-dimethoxybenzylamines and its use in the synthesis of secondary amines," Tetrahedron, 47(26):4591-4602 (1991).
Parikh and Doering, "Sulfur trioxide in the oxidation of alcohols by dimethyl sulfoxide," J. Am. Chem. Soc., 1967, 89(21):5505-5507.
Patani and LaVoie, Bioisosterism: A Rational Approach in Drug Design, Chem. Rev. 1996, 96, pp. 3147-3176.
Pfitzner and Moffat, "A New and Selective Oxidation of Alcohols," J. Am. Chem. Soc., 1963, 85(19):3027-3028.
Prakash et al., "Perfluoroalkylation with Organosilicon Reagents," Chem. Rev., 97:757-786 (1997).

Quach and Batey, "Ligand- and Base-Free Copper(II)-Catalyzed C—N Bond Formation: Cross-Coupling Reactions of Organoboron Compounds with Aliphatic Amines and Anilines," Org. Lett., 5(23):4397-4400 (2003).
Rao et al., "Improved Synthesis of Mirtazapine," Org. Prep. Proced. Int., 39(4):399-402 (2007).
Rolandsgard et al., "Stereoselective preparation of spirane bridged, sandwiched bisarenes," Tetrahedron, 61(16):4128-4140 (2005).
Romero et al., "Discovery, synthesis, and bioactivity of bis(heteroaryl)piperazines. 1. A novel class of non-nucleoside HIV-1 reverse transcriptase inhibitors," J Med. Chem., 37(7):999-1014 (1994).
Rosowsky et al., "Synthesis and biological activity of the 2-desamino and 2-desamino-2-methyl analogues of aminopterin and methotrexate," J. Med. Chem., 34(1):227-234 (1991).
Sankaranarayanan et al., "First demonstration of cerebrospinal fluid and plasma A beta lowering with oral administration of a beta-site amyloid precursor protein-cleaving enzyme 1 inhibitor in nonhuman primates," J Pharmacol. Exp. Ther., 328:131-140 (2009).
Sankaranarayanan et al., "In Vivo 62 -Secretase 1 Inhibition Leads to Brain A$\beta$ Lowering and Increased $\alpha$-Secretase Processing of Amyloid Precursor Protein without Effect on Neuregulin-1," Pharmacol. Exp. Ther, 324(3):957-969 (2008).
Sapountzis et al., "Synthesis of Functionalized Nitroarylmagnesium Halides via an Iodine—Magnesium Exchange," J. Org. Chem., 70(7):2445-2454 (2005).
Sase et al., "One-Pot Negishi Cross-Coupling Reactions of in Situ Generated Zinc Reagents with Aryl Chlorides, Bromides, and Triflates," J. Org. Chem., 2008, 73(18):7380-7382.
Satoh et al., "Synthesis of 4-substituted phenylalanine derivatives by cross-coupling reaction of p-boronophenylalanines," Tet. Lett. 1997, 38(44):7645-7648.
Scheuner et al., "Secreted amyloid $\beta$-protein similar to that in the senile plaques of Alzheimer's disease is increased in vivo by the presenilin 1 and 2 and APP mutations linked to familial Alzheimer's disease," Nature Medicine, 2(8):864-870 (1996).
Schinkel, "P-Glycoprotein, a gatekeeper in the blood-brain barrier," Adv. Drug Deliv. Rev., 36:179-194 (1999).
Schwizer et al., "Antagonists of the myelin-associated glycoprotein: A new class of tetrasaccharide mimics," Bioorg. Med. Chem., 14:4944-4957 (2006).
Selles and Mueller, "Expedient Synthesis of Highly Substituted Fused Heterocoumarins," Org. Lett., 6(2):277-279 (2004).
Shao et al., "4-(2-Pyridyl)piperazine- 1 -benzimidazoles as potent TRPV1 antagonists," Bioorg. Med. Chem. Lett., 15(3):719-723 (2005).
Shing et al., "Intramolecular nitrile oxide-alkene cycloaddition of sugar derivatives with unmasked hydroxyl group(s)," Org. Lett., 9(5):753-756 (2007).
Singh et al., "Recent Advances in Nucleophilic Fluorination Reactions of Organic Compounds Using Deoxofluor and DAST," Synthesis, 2002, 17:2561-2578.
Soderberg, Section 13.1: Tautomers —Chemwiki, retrieved on Oct. 30, 2013 http://chemwiki.ucdavis.edu/Organic_Chemistry/Organic_Chemistry_With_a_Biological_Emphasis/ Chapter_13%03A_Reactions_with_stabilized_carbanion_intermediates_1/Section_13.1%3A_Tautomers, 5 pages.
Stille et al., "4-Methoxy-4'-Nitrobiphenyl," Org. Synth., 1998, Coll. vol. 9:553.
Stille, "The Palladium-Catalyzed Cross-Coupling Reactions of Organotin Reagents with Organic Electrophiles [New Synthetic Methods (58)]," Angew. Chem. Int. Ed. Engl. 1986, 25:508-524.
Summerfield et al., "Central nervous system drug disposition: the relationship between in situ brain permeability and brain free fraction," J. Pharmacol. Exp. Ther., 322:205-213 (2007).
Suzuki, "Cross-coupling Reactions of Organoboron Compounds with Organice Halides," Metal-Catalyzed Cross-Coupling Reactions 1998, 49-97.
Suzuki, "Recent advances in the cross-coupling reactions of organoboron derivatives with organic electrophiles, 1995-1998," J Organometallic Chem. 1999, 576, 147-168.

(56) References Cited

OTHER PUBLICATIONS

Suzuki, "Synthetic studies via the cross-coupling reaction of organoboron derivatives with organic halides," Pure Appl. Chem. 1991, 63, 419-422.

Tamao et al., "Selective carbon-carbon bond formation by cross-coupling of Grignard reagents with organic halides. Catalysis by nickel-phosphine complexes," J. Am. Chem. Soc. 1972, 94 (12):4374-4376.

Tamayo et al., Design and synthesis of potent pyridazine inhibitors of p38 MAP kinase, *Bioorg. Med. Chem. Lett.*,15(9):2409-2413 (2005).

Tao et al., "Copper-catalyzed synthesis of aryl azides and 1-aryl-1,2,3-triazoles from boronic acids," *Tetrahedron Lett.*, 48:3525-3529 (2007).

Tidewell, "Oxidation of Alcohols by Activated Dimethyl Sulfoxide and Related Reactions: An Update," Synthesis, 1990, 857-870.

Tidwell, "Oxidation of Alcohols to Carbonyl Compounds via Alkoxysulfonium Ylides: The Moffatt, Swern, and Related Oxidations," Org. React. 1990, 39:297-572.

Trainor, "The importance of plasma protein binding in drug discovery," *Expert Opin. Drug Discov.*, 2:51-64 (2007).

Tzschucke et al., "Arenes to Anilines and Aryl Ethers by Sequential Iridium-Catalyzed Borylation and Copper-Catalyzed Coupling," *Org. Lett.*, 9(5):761-764 (2007).

Tzvetkov et al., Synthesis and photoinitiated radical cyclization of allyl- and propynyloxymethyl substituted cyclopentanones to tetrahydrocyclopenta[c]furanols, *Tetrahedron Lett.*, 46(45):7751-7755 (2005).

Ueno, "Molecular anatomy of the brain endothelial barrier: an overview of the distributional features," *Curr. Med. Chem.*, 14:1199-1206 (2007).

Uno et al., "Reaction of 2-Isoxazolines with Organolithiums in the Presence of Boron Trifluoride," *Bull. Chem. Soc. Jpn.*, 66:2730-2737 (1993).

Vedejs et al., "Enantiocontrolled Synthesis of (1S,2S)-6-Desmethyl-(methylaziridino)mitosene," *J. Am. Chem. Soc.*, 122(22):5401-5402 (2000).

Vedejs et al., "Synthetic Enantiopure Aziridinomitosenes: Preparation, Reactivity, and DNA Alkylation Studies," *J. Am. Chem. Soc.*, 125(51):15796-15806 (2003).

Watanabe et al., "A convenient method for the synthesis of $\Delta 1,6$-bicyclo[4.n.0]alken-2-ones," *Tetrahedron Lett.*, 40(46):8133-8136 (1999).

Whisler et al., "Synthetic applications of lithiated N-Boc allylic amines as asymmetric homoenolate equivalents," *J. Org. Chem.*, 68:1207-1215 (2003).

Willis and Strongin, "Palladium-catalyzed cross-coupling of aryldiazonium tetrafluoroborate salts with arylboronic esters," Tet. Lett. 2000, 41(33):6271-6274.

Zhou and Fu, "Palladium-Catalyzed Negishi Cross-Coupling Reactions of Unactivated Alkyl Iodides, Bromides, Chlorides, and Tosylates," J. Am. Chem. Soc., 2003, 125(41):12527-12530.

\* cited by examiner

FUSED AMINODIHYDROTHIAZINE DERIVATIVES

The present invention relates to a fused aminodihydrothiazine derivative and pharmaceutical use thereof. More particularly, the present invention relates to a fused aminodihydrothiazine derivative which has an amyloid-β (hereinafter referred to as Aβ) protein production inhibitory effect or a beta-site amyloid-β precursor protein cleavage enzyme 1 (hereinafter referred to as BACE1 or beta-secretase) inhibitory effect and is effective for treating a neurodegenerative disease caused by Aβ protein, in particular, Alzheimer-type dementia, Downs syndrome or the like, and to a pharmaceutical composition comprising the fused aminodihydrothiazine derivative as an active ingredient.

Alzheimer's disease is a disease characterized by degeneration and loss of neurons as well as formation of senile plaques and neurofibrillary tangles. Currently, only the symptoms of Alzheimer's disease are treated using a symptom-improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as breakdown products of amyloid precursor proteins (hereinafter referred to as Aβ) are highly involved in degeneration and loss of neurons and onset of symptoms of dementia. Aβ-proteins have, as main components, Aβ40 consisting of 40 amino acids and Aβ42 with two amino acids added at the C-terminal. The Aβ40 and Aβ42 are known to have high aggregability and to be main components of senile plaques. Further, it is known that the Aβ40 and Aβ42 are increased by mutation in APP and presenilin genes which is observed in familial Alzheimer's disease. Accordingly, a compound that reduces production of Aβ40 and Aβ42 is expected to be a progression inhibitor or prophylactic agent for Alzheimer's disease.

Aβ is produced by the cleavage of APP by beta-secretase (BACE1) and subsequently by gamma-secretase. For this reason, attempts have been made to create gamma-secretase and beta-secretase inhibitors in order to inhibit Aβ production.

Published International patent application WO2009/151098 (Shionogi & Co., Ltd.) describes a sulfur-containing heterocyclic derivative of formula (A) having β-secretase activity:

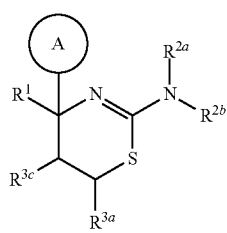

(A)

where $R^1$, $R^{2a}$, $R^{2b}$, $R^{3a}$, $R^{3c}$ and ring A are defined therein.

Published International patent application WO2008/133274 (Shionogi & Co., Ltd.) describes aminodihydrothiazine derivatives substituted with cyclic groups of formula (B):

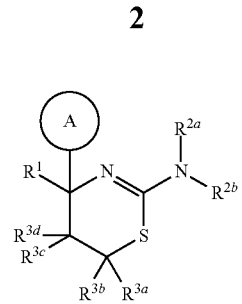

(B)

where $R^1$, $R^{2a}$, $R^{2b}$, $R^{3a}$, $R^{3b}$, $R^{3c}$, $R^{3d}$ and ring A are defined therein, which are useful as remedies for diseases induced by the production, secretion, or deposition of amyloid β protein.

Published International patent application WO2008/133273 (Shionogi & Co., Ltd.) describes a pharmaceutical composition for the treatment of Alzheimer's disease which contains a compound of formula (C):

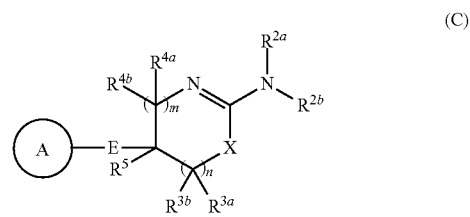

(C)

where $R^{2a}$, $R^{2b}$, $R^{3a}$, $R^{3b}$, $R^{4a}$, $R^{4b}$, $R^5$, m, n, X, E and ring A are defined therein.

Published International patent application WO2007/049532 and European patent application EP1942105 (both Shionogi & Co., Ltd.) describe aminodihydrothiazine derivatives of formula (D):

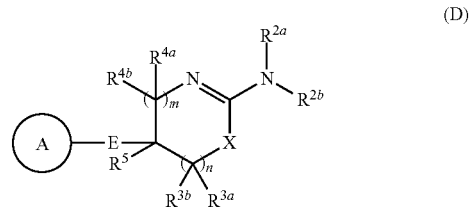

(D)

where $R^{2a}$, $R^{2b}$, $R^{3a}$, $R^{3b}$, $R^{4a}$, $R^{4b}$, $R^5$, m, n, X, E and ring A are defined therein, as BACE 1 inhibitors.

Published International patent application WO2009/134617 (Eli Lilly and Company) describes aminodihydrothiazine derivatives of formula (E) as BACE inhibitors for the treatment of Alzheimer's disease:

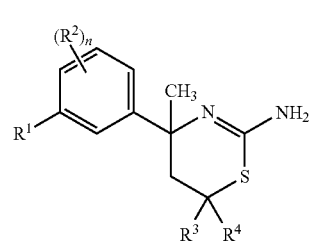

(E)

where $R^1$, $R^2$, $R^3$, $R^4$ and n are defined therein.

Published International patent application WO2010/021680 (Vitae Pharmaceuticals, Inc.) describes compounds of formula (F) as inhibitors of BACE activity useful as therapeutic agents in the treatment of diseases characterised by elevated β-amyloid deposits or β-amyloid levels in a patient:

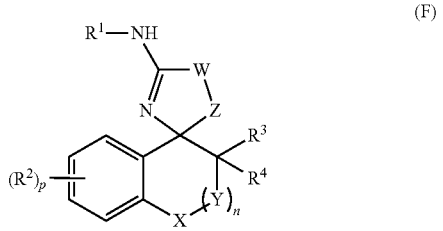

(F)

where $R^1$, $R^2$, $R^3$, $R^4$, W, X, Y, Z, n and p are defined therein.

Published International patent application WO2010/105179 (Vitae Pharmaceuticals, Inc.; Boehringer Ingelheim International GmbH) describes compounds of formula (G) as BACE inhibitors useful as therapeutic agents in the treatment of diseases characterised by elevated β-amyloid deposits or β-amyloid levels in a patient:

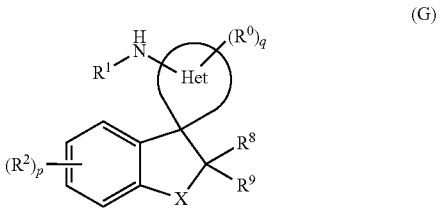

(G)

where ring Het, X, $R^0$, $R^1$, $R^2$, $R^8$, $R^9$, p and q are defined therein.

Fused aminodihydrothiazine compounds of formula (H) have already been described in published International patent application WO2009/091016 and US patent application 2009/0209755 (both Eisai R&D Management Co., Ltd.):

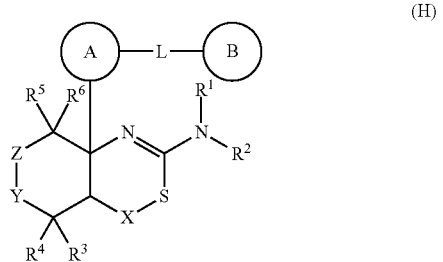

(H)

wherein ring A represents a $C_{6-14}$aryl group or the like; L represents —NR$^e$CO— [wherein R$^e$ represents a hydrogen atom or the like] or the like; ring B represents a $C_{6-14}$aryl group or the like; X represents a $C_{1-3}$alkylene group or the like; Y represents a single bond or the like; Z represents a $C_{1-3}$alkylene group or the like; $R^1$ and $R^2$ independently represent a hydrogen atom or the like; and $R^3$, $R^4$, $R^5$ and $R^6$ independently represent a hydrogen atom, a halogen atom or the like. The compounds of the present invention represent a selection over the genus of compounds disclosed in WO2009/091016.

Further fused aminodihydrothiazine compounds of formula (I) have been described in published International patent application WO2010/038686 (Eisai R&D Management Co., Ltd.):

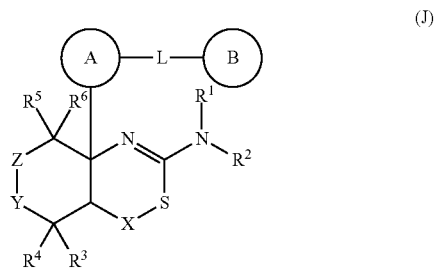

(J)

wherein ring A represents a $C_{6-14}$aryl group or the like; L represents —NR$^e$CO— [wherein R$^e$ represents a hydrogen atom or the like] or the like; the ring B represents a $C_{6-14}$aryl group or the like; X represents a $C_{1-3}$alkylene group or the like; Y represents a single bond or the like; Z represents an oxygen atom or the like; $R^1$ and $R^2$ each independently represents a hydrogen atom or the like; and $R^3$, $R^4$, $R^5$ and $R^6$ each independently represents a hydrogen atom, a halogen atom or the like.

An object of the present invention is to provide further compounds that have an Aβ production inhibitory effect or a BACE1 inhibitory effect and are useful as prophylactic or therapeutic agents for a neurodegenerative disease caused by Aβ and typified by Alzheimer-type dementia, which compounds are fused aminodihydrothiazine derivatives.

Thus, the present invention provides a compound of formula (I):

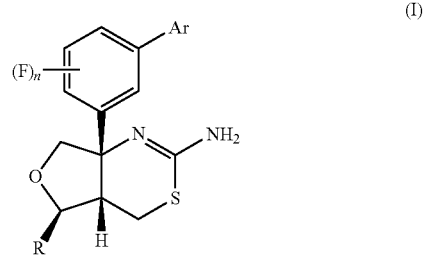

(I)

wherein

R is hydrogen or $C_{1-6}$alkyl, optionally substituted by one to five halogen atoms;

n is 0, 1, 2 or 3;

Ar is phenyl or a 5- or 6-membered heteroaromatic group containing 1, 2 or 3 N atoms, which Ar is optionally substituted by one to three substituents selected from hal, hydroxyl, —CN, $C_{1-6}$alkyl, $C_{2-3}$alkenyl, $C_{2-3}$alkynyl, $C_{1-6}$alkoxy, $C_{3-6}$cycloalkoxy and pyrazine, where $C_{1-6}$alkyl and $C_{1-6}$alkoxy are optionally substituted by one to three halogen atoms;

and pharmaceutically acceptable salts thereof.

In one embodiment of the present invention, R is hydrogen or $C_{1-3}$alkyl, optionally substituted by one to three fluorine or chlorine atoms. Preferably, R is hydrogen or $C_{1-2}$alkyl, optionally substituted by one to three fluorine atoms. More preferably, R is $C_{1-2}$alkyl, optionally substituted by one to three fluorine atoms. Most preferably, R is methyl, monofluoromethyl, difluoromethyl, trifluoromethyl, ethyl, monofluoroethyl, difluoroethyl or trifluoroethyl. Examples of suitable R groups include methyl, monofluoromethyl, difluoromethyl and trifluoromethyl.

In one embodiment of the present invention, R is methyl.

In one embodiment of the present invention, R is monofluoromethyl,

In another embodiment of the present invention, n is 0, 1 or 2.

In another embodiment of the present invention, n is 1.

In another embodiment of the present invention, n is 2.

In another embodiment of the present invention, n is 1, 2 or 3, and one of the fluorine atoms is attached to the 6-position of the phenyl ring:

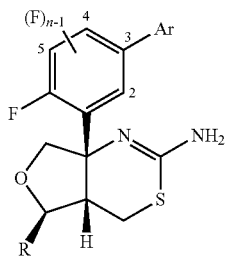

In another embodiment of the present invention, Ar is phenyl or a 5- or 6-membered heteroaromatic group containing 1, 2 or 3 N atoms, which Ar is optionally substituted by one to three substituents selected from hal, —CN, $C_{1-6}$alkyl, $C_{2-3}$alkenyl, $C_{2-3}$alkynyl, $C_{1-6}$alkoxy, and pyrazine, where $C_{1-6}$alkyl and $C_{1-6}$alkoxy are optionally substituted by one to three halogen atoms.

In another embodiment of the present invention, Ar is phenyl or a 5- or 6-membered heteroaromatic group containing 1, 2 or 3 N atoms, which Ar is optionally substituted by one or two substituents selected from hal, —CN, $C_{1-3}$alkyl, $C_{2-3}$alkynyl, $C_{1-3}$alkoxy and pyrazine, where $C_{1-3}$alkyl and $C_{1-3}$alkoxy are optionally substituted by one to three fluorine atoms.

Preferably, Ar is phenyl, pyridinyl, pyrimidinyl, pyrazinyl, pyridazinyl, pyrazolyl or imidazolyl, which Ar is optionally substituted by one or two substituents selected from fluorine, —CN, $C_{1-2}$alkyl, $C_{1-2}$alkoxy, trifluoromethyl and pyrazine. Examples of suitable Ar groups are phenyl,

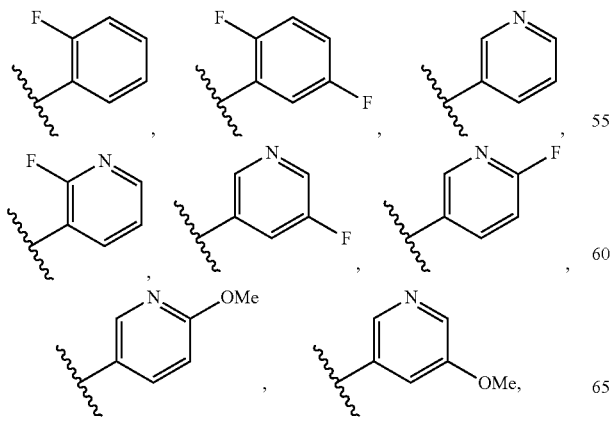

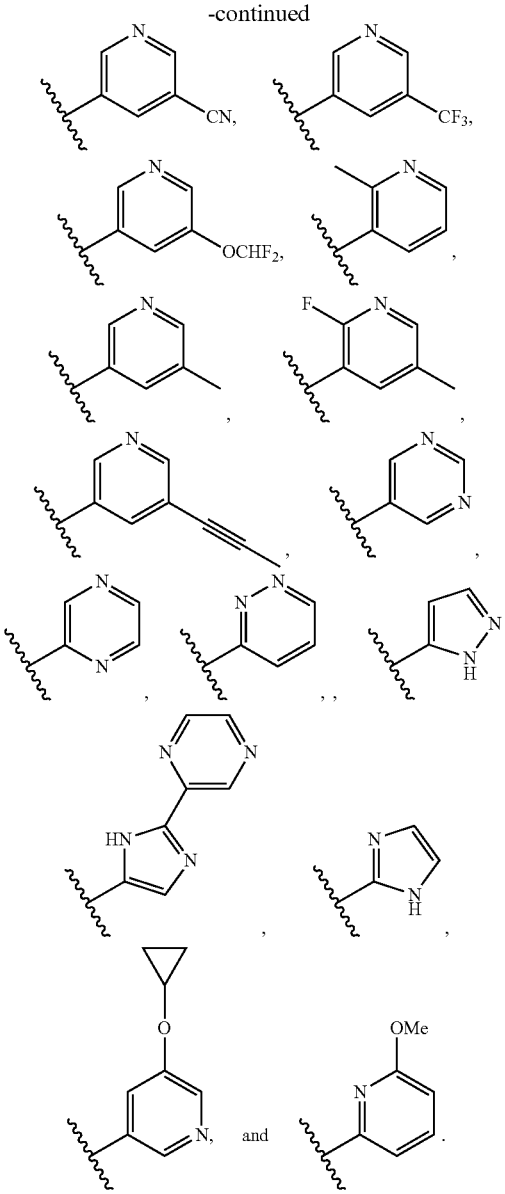

One favoured group of compounds of the present invention is the compound of formula (Ia) and pharmaceutically acceptable salts thereof:

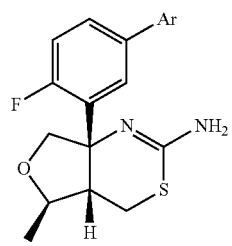

wherein Ar is hereinbefore defined.

In one embodiment, the present invention provides a compound of formula (Ia) wherein Ar is phenyl, pyridinyl, pyrimidinyl, pyridazinyl, pyrazolyl or imidazolyl, which Ar is optionally substituted by one or two substituents selected from fluorine, —CN, $C_{1-2}$alkyl, $C_{1-2}$alkoxy, cyclopropoxy, trifluoromethyl, difluoromethoxy and pyrazine.

In one embodiment, the present invention provides a compound of formula (Ib) and pharmaceutically acceptable salts thereof:

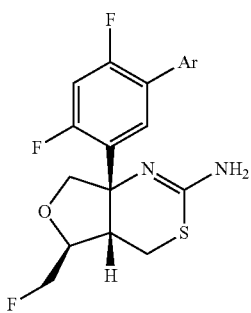

(Ib)

wherein Ar is hereinbefore defined.

In one embodiment, the present invention provides a compound of formula (Ib) wherein Ar is pyridinyl or pyrimidinyl, which Ar is optionally substituted by one or two substituents selected from fluorine, $C_{1-2}$alkyl, and $C_{1-2}$alkoxy.

Preferred compounds of the present invention are:
(4aS,5R,7aS)-7a-(2-Fluoro-5-(pyrimidin-5-yl)phenyl)-5-methyl-4a,5,7,7a-tetrahydro-4H-furo[3,4-d][1,3]thiazin-2-amine,
(4aS,5R,7aS)-7a-(2-Fluoro-5-(1H-imidazol-2-yl)phenyl)-5-methyl-4a,5,7,7a-tetrahydro-4H-furo[3,4-d][1,3]thiazin-2-amine,
(4aS,5R,7aS)-7a-(2-fluoro-5-(2-(pyrazin-2-yl)-1H-imidazol-5-yl)phenyl)-5-methyl-4a,5,7,7a-tetrahydro-4H-furo[3,4-d][1,3]thiazin-2-amine,
(4aS,5R,7aS)-7a-(2-Fluoro-5-(pyridin-3-yl)phenyl)-5-methyl-4a,5,7,7a-tetrahydro-4H-furo[3,4-d][1,3]thiazin-2-amine,
(4aS,5R,7aS)-7a-(4-Fluoro-[1,1'-biphenyl]-3-yl)-5-methyl-4a,5,7,7a-tetrahydro-H-furo[3,4-d][1,3]thiazin-2-amine,
(4aS,5R,7aS)-7a-(2',4-difluoro-[1,1'-biphenyl]-3-yl)-5-methyl-4a,5,7,7a-tetrahydro-4H-furo[3,4-d][1,3]thiazin-2-amine,
(4aS,5R,7aS)-7a-(2-Fluoro-5-(2-fluoropyridin-3-yl)phenyl)-5-methyl-4a,5,7,7a-tetrahydro-4H-furo[3,4-d][1,3]thiazin-2-amine,
(4aS,5R,7aS)-7a-(2-fluoro-5-(5-methoxypyridin-3-yl)phenyl)-5-methyl-4a,5,7,7a-tetrahydro-4H-furo[3,4-d][1,3]thiazin-2-amine,
(4aS,5R,7aS)-7a-(2-Fluoro-5-(5-fluoropyridin-3-yl)phenyl)-5-methyl-4a,5,7,7a-tetrahydro-4H-furo[3,4-d][1,3]thiazin-2-amine,
(4aS,5R,7aS)-7a-(2-Fluoro-5-(6-fluoropyridin-3-yl)phenyl)-5-methyl-4a,5,7,7a-tetrahydro-4H-furo[3,4-d][1,3]thiazin-2-amine,
(4aS,5R,7aS)-7a-(2-Fluoro-5-(6-methoxypyridin-3-yl)phenyl)-5-methyl -4a,5,7,7a-tetrahydro-4H-furo[3,4-d][1,3]thiazin-2-amine,
(4aS,5R,7aS)-5-Methyl-7a-(2',4,5'-trifluoro-[1,1'-biphenyl]-3-yl)-4a,5,7,7a-tetrahydro-4H-furo[3,4-d][1,3]thiazin-2-amine,
5-(3-((4aS,5R,7aS)-2-Amino-5-methyl-4a,5,7,7a-tetrahydro-4H-furo[3,4-d][1,3]thiazin-7a-yl)-4-fluorophenyl)nicotinonitrile;
(4aS,5R,7aS)-7a-(2-Fluoro-5-(5-(trifluoromethyl)pyridin-1-yl)phenyl)-5-methyl-4a,5,7,7a-tetrahydro-4H-furo[3,4-d][1,3]thiazin-2-amine;
(4aS,5R,7aS)-7a-(2-Fluoro-5-(5-methylpyridin-3-yl)phenyl)-5-methyl-4a,5,7,7a-tetrahydro-4H-furo[3,4-d][1,3]thiazin-2-amine,
(4aS,5R,7aS)-7a-(2-Fluoro-5-(2-fluoro-5-methylpyridin-3-yl)phenyl)-5 yl-4a,5,7,7a-tetrahydro-4H-furo[3,4-d][1,3]thiazin-2-amine,
(4aS,5R,7aS)-7a-(2-Fluoro-5-(1H-pyrazol-5-yl)phenyl)-5-methyl-4a,5,7,7a-tetrahydro-4H-furo[3,4-d][1,3]thiazin-2-amine,
(4aS,5R,7aS)-7a-(2-fluoro-5-(2-methylpyridin-3-yl)phenyl)-5-methyl-4a,5,7,7a-tetrahydro-4H-furo[3,4-d][1,3]thiazin-2-amine,
(4aS,5R,7aS)-7a-(2-fluoro-5-(5-(prop-1-yn-1-yl)pyridin-3-yl)phenyl)-5-methyl-4a,5,7,7a-tetrahydro-4H-furo[3,4-d][1,3]thiazin-2-amine,
(4aS,5R,7aS)-7a-(2-fluoro-5-(1-methyl-1H-pyrazol-5-yl)phenyl)-5-methyl-4a,5,7,7a-tetrahydro-4H-furo[3,4-d][1,3]thiazin-2-amine,
(4aS,5R,7aS)-7a-(5-(5-cyclopropoxypyridin-3-yl)-2-fluorophenyl)-5-methyl-4a,5,7,7a-tetrahydro-4H-furo[3,4-d][1,3]thiazin-2-amine,
(4aS,5R,7aS)-7a-(2-fluoro-5-(pyridazin-2-yl)phenyl)-5-methyl-4a,5,7,7a-tetrahydro-4H-furo[3,4-d][1,3]thiazin-2-amine,
(4aS,5R,7aS)-7a-(2-fluoro-5-(pyridazin-3-yl)phenyl)-5-methyl-4a,5,7,7a-tetrahydro-4H-furo[3,4-d][1,3]thiazin-2-amine,
(4aS,5R,7aS)-7a-(2-fluoro-5-(6-methoxypyridin-2-yl)phenyl)-5-methyl-4a,5,7,7a-tetrahydro-4H-furo[3,4-d][1,3]thiazin-2-amine,
6-(3-((4aS,5R,7aS)-2-amino-5-methyl-4a,5,7,7a-tetrahydro-4H-furo[3,4-d][1,3]thiazin-7a-yl)-4-fluorophenyl)pyridin-2(1H)-one,
(4aS,5R,7aS)-7a-(5-(5-(difluoromethoxy)pyridin-3-yl)-2-fluorophenyl)-5-methyl-4a,5,7,7a-tetrahydro-4H-furo[3,4-d][1,3]thiazin-2-amine,
(4aS,5S,7aS)-7a-(2,4-Difluoro-5-(pyrimidin-5-yl)phenyl)-5-(fluoromethyl)-4a,5,7,7a-tetrahydro-4H-furo[3,4-d][1,3]thiazin-2-amine,
(4aS,5S,7aS)-7a-(2,4-difluoro-5-(2-fluoropyridin-3-yl)phenyl)-5-(fluoromethyl)-4a,5,7,7a-tetrahydro-4H-furo[3,4-d][1,3]thiazin-2-amine,
(4aS,5S,7aS)-7a-(2,4-difluoro-5-(5-methoxypyridin-3-yl)phenyl)-5-fluoromethyl)-4a,5,7,7a-tetrahydro-4H-furo[3,4-d][1,3]thiazin-2-amine,
(4aS,5S,7aS)-7a-(2,4-difluoro-5-(6-fluoropyridin-3-yl)phenyl)-5-(fluoromethyl)-4a,5,7,7a-tetrahydro-4H-furo[3,4-d][1,3]thiazin-2-amine,
(4aS,5R,7aS)-7a-(2,4-Difluoro-5-(pyrimidin-5-yl)phenyl)-5-methyl-4a,5,7,7a-tetrahydro-4H-furo[3,4-d][1,3]thiazin-2-amine,
and pharmaceutically acceptable salts thereof.

In one embodiment, the present invention provides a compound (4aS,5R,7aS)-7a-(2-Fluoro-5-(pyrimidin-5-yl)phenyl)-5-methyl-4a,5,7,7a-tetrahydro-4H-furo[3,4-d][1,3]thiazin-2-amine, or a pharmaceutically acceptable salt thereof.

In another embodiment, the present invention provides a compound (4aS,5R,7aS)-7a-(2-fluoro-5-(5-(prop-1-yn-1-yl)pyridin-3-yl)phenyl)-5-methyl-4a,5,7,7a-tetrahydro-4H-furo[3,4-d][1,3]thiazin-2-amine, or a pharmaceutically acceptable salt thereof.

In another embodiment, the present invention provides a compound (4aS,5R,7aS)-7a-(2-fluoro-5-(pyrazin-2-yl)phenyl)-5-methyl-4a,5,7,7a-tetrahydro-4H-furo[3,4-d][1,3]thiazin-2-amine, or a pharmaceutically acceptable salt thereof.

In another embodiment, the present invention provides a compound (4aS,5R,7aS)-7a-(5-(5-(difluoromethoxy)pyridin-3-yl)-2-fluorophenyl)-5-methyl-4a,5,7,7a-tetrahydro-4H-furo[3,4-d][1,3]thiazin-2-amine, or a pharmaceutically acceptable salt thereof.

In another embodiment, the present invention provides a compound (4aS,5S,7aS)-7a-(2,4-Difluoro-5-(pyrimidin-5-yl)phenyl)-5-(fluoromethyl)-4a,5,7,7a-tetrahydro-4H-furo[3,4-d][1,3]thiazin-2-amine, or a pharmaceutically acceptable salt thereof.

When any variable occurs more than one time in formula (I) or in any substituent, its definition on each occurrence is independent of its definition at every other occurrence.

As used herein, the terms "Hal" and "halogen atom" refer to fluorine, chlorine, bromine and iodine and are preferably fluorine or chlorine, more preferably fluorine.

As used herein, the term "$C_{1-6}$alkyl" refers to an alkyl group having 1 to 6 carbon atoms. Preferable examples of the group include linear or branched alkyl groups such as methyl, ethyl, n-propyl, isopropyl, n-butyl, isobutyl, t-butyl, n-pentyl, isopentyl, neopentyl, n-hexyl, 1-methylpropyl, 1,2-dimethylpropyl, 1-ethylpropyl, 1-methyl-2-ethylpropyl, 1-ethyl-2-methylpropyl, 1,1,2-trimethylpropyl, 1-methylbutyl, 2-methylbutyl, 1,1-dimethylbutyl, 2,2-dimethylbutyl, 2-ethylbutyl, 1,3-dimethylbutyl, 2-methylpentyl and 3-methylpentyl. The group is more preferably methyl, ethyl or n-propyl.

As used herein, the term "$C_{2-3}$alkenyl" refers to an alkenyl group having 2 to 3 carbon atoms. Preferable examples of the group include linear or branched alkenyl groups such as vinyl, allyl, 1-propenyl and isopropenyl.

As used herein, the term "$C_{2-3}$alkynyl" refers to an alkynyl group having 2 to 3 carbon atoms. Preferable examples of the group include ethynyl, 1-propynyl and 2-propynyl.

As used herein, the term "$C_{1-6}$alkoxy" refers to an alkyl group having 1 to 6 carbon atoms in which one methylene group is replaced by an oxygen atom. Examples of the group include methoxy, ethoxy, n-propoxy, isopropoxy, n-butoxy, isobutoxy, sec-butoxy, t-butoxy, n-pentoxy, isopentoxy, sec-pentoxy, t-pentoxy, n-hexyloxy, isohexyloxy, 1,2-dimethylpropoxy, 2-ethylpropoxy, 1-methyl-2-ethylpropoxy, 1-ethyl-2-methylpropoxy, 1,1,2-trimethylpropoxy, 1,1-dimethylbutoxy, 2,2-dimethylbutoxy, 2-ethylbutoxy, 1,3-dimethylbutoxy, 2-methylpentoxy, 3-methylpentoxy and hexyloxy.

As used herein the term "$C_{3-6}$cycloalkoxy" refers to an alkoxy group wherein the alkyl component forms a cyclic ring having 3 to 6 carbon atoms. Examples of the group include cyclopropoxy, cyclobutoxy, cyclopentoxy and cyclohexoxy.

As used herein, the term "5- or 6-membered heteroaromatic" refers to a heteroatom-containing aromatic cyclic group containing 1, 2 or 3 N atoms and having 5 or 6 members in total. Examples of the group include pyrrolyl, imidazolyl, pyrazolyl, pyridinyl, pyridazinyl, pyrimidinyl, pyrazinyl, triazolyl and triazinyl. When Ar is pyridinyl examples of a pyridinyl group substituted with a hydroxyl include tautomers thereof such as 2-pyridones.

Where a compound or group is described as "optionally substituted", it may be unsubstituted or substituted by one or more substituents, for example, 1, 2 or 3 substituents.

Specific compounds within the scope of this invention include those named in the Examples below and their pharmaceutically acceptable salts.

The compound of formula (I) is not limited to a specific isomer and includes all possible isomers (such as a keto-enol isomer, an imine-enamine isomer, a diastereoisomer and a rotamer) and mixtures thereof; including racemates. For example, the compound of formula (I) includes the following tautomers:

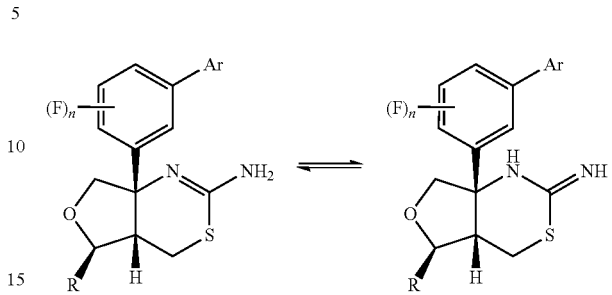

The compounds of the present invention contain three chiral centers located on the tetrahydrofuro-thiazinyl ring within formula (I), at the 4a, 5 and 7a ring positions. For the avoidance of doubt, compounds according to the present invention may be present as a mixture with one or more other possible stereoisomers, for example in a racemic mixture. However, in one embodiment, the present invention provides a compound of formula (I) which is stereochemically pure at the (4a, 5, 7a) positions. In the context of the present specification, the term stereochemically pure denotes a compound which has 80% or greater by weight of one stereoisomer and 20% or less by weight of other stereoisomers. In a further embodiment, the compound of formula (I) has 90% or greater by weight of one stereoisomer and 10% or less by weight of other stereoisomers. In a yet further embodiment, the compound of formula (I) has 95% or greater by weight of one stereoisomer and 5% or less by weight of other stereoisomers. In a still further embodiment, the compound of formula (I) has 97% or greater by weight of the one stereoisomer and 3% or less by weight of other stereoisomers.

In one embodiment, the present invention provides a compound of formula (Ia) wherein the stereochemical configuration at the 4a, 5 and 7a ring positions is (4aS,5R,7aS). In a further aspect of this embodiment, the compound of formula (Ia) is stereochemically pure.

In one embodiment, the present invention provides a compound of formula (Ib) wherein the stereochemical configuration at the 4a, 5 and 7a ring positions is (4aS,5S,7aS). In a further aspect of this embodiment, the compound of formula (Ib) is stereochemically pure.

In the present specification, although crystal polymorphs of the compound may be present, the compound is similarly not limited thereto and may be present as a single crystal form or a mixture of single crystal forms. The compound may be an anhydride or a hydrate. Any of these forms is included in the claims of the present specification.

The present invention also includes isotopically-labelled compounds, which are identical to the compounds of formula (I), except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, fluorine, phosphorous, chlorine and iodine, such as $^{2}H$, $^{3}H$, $^{11}C$, $^{14}C$, $^{13}N$, $^{15}O$, $^{18}F$, $^{32}P$, $^{35}S$, $^{123}I$ and $^{131}I$.

Compounds of the present invention and pharmaceutically acceptable derivatives (e.g. salts) of said compounds that contain the aforementioned isotopes and/or other isotopes of other atoms are within the scope of the present invention. Isotopically labelled compounds of the present invention, for example those into which radioactive isotopes such as $^3$H and/or $^{14}$C are incorporated, are useful in drug and/or substrate tissue distribution assays. $^3$H and $^{14}$C are considered useful due to their ease of preparation and detectability. $^{11}$C, $^{15}$O and $^{18}$F isotopes are considered useful in PET (positron emission tomography), and $^{123}$I and $^{131}$I isotopes are considered useful in SPECT (single photon emission computerized tomography), all useful in brain imaging. Substitution with heavier isotopes such as $^2$H can afford certain therapeutic advantages resulting from greater metabolic stability, for example increased in vivo half-life or reduced dosage requirements and, hence, are considered useful in some circumstances. Isotopically labelled compounds of formula (I) of this invention can generally be prepared by carrying out the procedures disclosed in the Schemes and/or in the Examples below, by substituting a readily available isotopically labelled reagent for a non-isotopically labelled reagent.

The fused aminodihydrothiazine derivative of the formula (I) according to the present invention may be a pharmaceutically acceptable salt. Pharmaceutically acceptable salts include those described by Berge, Bighley and Monkhouse, J. Pharm. Sci., 1977, 766, 1-19. Specific examples of the pharmaceutically acceptable salt include inorganic acid salts (such as sulfates, nitrates, perchlorates, phosphates, carbonates, bicarbonates, hydrofluorides, hydrochlorides, hydro bromides and hydroiodides), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

The compound of the formula (I) according to the present invention can be converted to a pharmaceutically acceptable salt by a conventional method where necessary. The salt can be prepared by a method in which methods typically used in the field of organic synthetic chemistry and the like are appropriately combined. Specific examples of the method include neutralization titration of a free solution of the compound of the present invention with an acid solution.

The fused aminodihydrothiazine derivative of the formula (I) or pharmaceutically acceptable salt according to the present invention may be a solvate thereof. Examples of a solvate include a hydrate.

The compound of the formula (I) according to the present invention can be converted to a solvate by subjecting the compound to a solvate forming reaction known per se where necessary.

The present invention further provides a compound of formula (I) or a pharmaceutically acceptable salt thereof for use in therapy.

The fused aminodihydrothiazine derivative or pharmaceutically acceptable salt thereof according to the present invention has an excellent Aβ production inhibitory effect or BACE1 inhibitory effect and is useful as a prophylactic or therapeutic agent for a neurodegenerative disease caused by Aβ and typified by Alzheimer-type dementia. The compounds of the invention reduce both Aβ40 and Aβ42. Furthermore, the compounds of the present invention may have a BACE 2 inhibitory effect.

Thus, in another aspect, the present invention provides a compound of formula (I) as defined above, or a pharmaceutically acceptable salt thereof, for inhibiting production of amyloid-β protein.

In a further aspect, the present invention provides a compound of formula (I) as defined above, or a pharmaceutically acceptable salt thereof, for inhibiting beta-site amyloid-β precursor protein cleaving enzyme 1 (BACE 1).

In a further aspect, the present invention provides a compound of formula (I) as defined above, or a pharmaceutically acceptable salt thereof, for treating a neurodegenerative disease. Examples of neurodegenerative diseases include Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD. In one embodiment, the neurodegenerative disease is Alzheimer-type dementia or Down's syndrome. In another embodiment, the neurodegenerative disease is Alzheimer-type dementia (AD).

In another aspect, the invention provides the use of a compound of formula (I) as defined above, or a pharmaceutically acceptable salt thereof, for the manufacture of a medicament for the treatment or prevention of a neurodegenerative disease such as Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD. In one embodiment, the neurodegenerative disease is Alzheimer-type dementia or Down's syndrome. In another embodiment, the neurodegenerative disease is Alzheimer-type dementia (AD).

In another aspect, the invention provides the use of a compound of formula (I) as defined above, or a pharmaceutically acceptable salt thereof, for the manufacture of a medicament for the treatment or prevention of a neurodegenerative disease, such as Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD. In one embodiment, the neurodegenerative disease is Alzheimer-type dementia (AD).

In another aspect, the invention provides a method of inhibiting production of amyloid-β protein and/or of treating or preventing a neurodegenerative disease, such as Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD, involving administering to a human subject suffering from the condition a therapeutically or prophylactically effective amount of a compound of formula (I) or a pharmaceutically acceptable salt thereof. Examples of neurodegenerative diseases include those listed above. In one embodiment, the neurodegenerative disease is Alzheimer-type dementia (AD). "Effective amount" means an amount sufficient to cause a benefit to the subject or at least to cause a change in the subject's condition.

Additional conditions which may be treated by the compounds of the present invention include type 2 diabetes, Creutzfield-Jakob Disease (CJD), peripheral nerve injury, peripheral neuropathy, progressive supra-nuclear palsy, stroke, amyotrophic lateral sclerosis (ALS), autoimmune diseases, inflammation, arterial thrombosis, anxiety disorders, psychotic disorders, epilepsy, seizures, convulsions, stress disorders, vascular amyloidosis, pain, Gerstmann-Straeussler-Scheinker syndrome, scrapie, encephalopathy, spino cerebellar ataxia, Wilson's Disease, Graves Disease, Huntington's Disease, Whipple's Disease, Kostmann Disease, glaucoma, hereditary cerebral hemorrhage with amyloidosis, cerebral hemorrhage with amyloidosis, vascular amyloidosis, brain inflammation, fragile X syndrome, stroke, Tourette's syndrome, inclusion body myositis, stress disorders, depression, bipolar disorder and obsessive compulsive disorder.

In one aspect the present invention further provides a compound of formula (I) as defined above, or a pharmaceutically acceptable salt thereof, for treating type 2 diabetes. In a further aspect the present invention further provides the use of a compound of formula (I) as defined above, or a pharmaceutically acceptable salt thereof, for the manufacture of a medicament for the treatment or prevention of type 2 diabetes. In a yet further aspect the present invention further provides a method of inhibiting production of amyloid-β protein and/or of treating or preventing type 2 diabetes involving administering to a human subject suffering from the condition a therapeutically or prophylactically effective amount of a compound of formula (I) or a pharmaceutically acceptable salt thereof.

A further aspect of the invention provides a pharmaceutical composition comprising a compound of formula (I) as defined above, or a pharmaceutically acceptable salt thereof, as active ingredient in association with a pharmaceutically acceptable earner. The composition may be in any suitable form, depending on the intended method of administration. It may for example be in the form of a tablet, capsule or liquid for oral administration, or of a solution or suspension for administration parenterally.

The fused aminodihydrothiazine derivative or pharmaceutically acceptable salt thereof according to the present invention can be formulated by a conventional method. Preferable examples of the dosage form include tablets, coated tablets such as film tablets and sugar-coated tablets, fine granules, granules, powders, capsules, syrups, troches, inhalants, suppositories, injections, ointments, eye drops, nasal drops, ear drops, cataplasms and lotions.

These solid preparations such as tablets, capsules, granules and powders can contain generally 0.01 to 100 wt %, and preferably 0.1 to 100 wt % of the fused aminodihydrothiazine derivative or pharmaceutically acceptable salt thereof according to the present invention as an active ingredient.

The active ingredient is formulated by blending ingredients generally used as materials for a pharmaceutical preparation and adding an excipient, a disintegrant, a binder, a lubricant, a colorant and a corrective typically used, and adding a stabilizer, an emulsifier, an absorbefacient, a surfactant, a pH adjuster, a preservative and an antioxidant where necessary, for example, using a conventional method. Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrant used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those permitted to be added to pharmaceuticals. Examples of the corrective used include cocoa powder, menthol, empasm, mentha oil, borneol and cinnamon powder. Obviously, the ingredients are not limited to the above additive ingredients.

For example, an oral preparation is prepared by adding the fused aminodihydrothiazine derivative or pharmaceutically acceptable salt thereof according to the present invention as an active ingredient, an excipient and, where necessary, a binder, a disintegrant, a lubricant, a colorant, a corrective and the like, and then forming the mixture into powder, fine granules, granules, tablets, coated tablets, capsules or the like by a conventional method. Obviously, tablets or granules may be appropriately coated, for example, sugar coated, where necessary.

For example, a syrup or an injection preparation is prepared by adding a pH adjuster, a solubilizer, an isotonizing agent and the like, and a solubilizing agent, a stabilizer and the like where necessary by a conventional method. The injection may be a previously prepared solution, or may be powder itself or powder containing a suitable additive, which is dissolved before use. The injection can contain usually 0.01 to 100 wt %, and preferably 0.1 to 100 wt % of the active ingredient. Further, a liquid preparation for oral administration such as a suspension or a syrup can contain usually 0.01 to 100 wt %, and preferably 0.1 to 100 wt % of the active ingredient.

For example, an external preparation can be prepared by any conventional method without specific limitations. As a base material, any of various materials usually used for a pharmaceutical, a quasi drug, a cosmetic or the like can be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like can be added where necessary. Further, ingredients such as an ingredient having a differentiation inducing effect, a blood flow enhancer, a bactericide, an antiphlogistic, a cell activator, vitamin, amino acid, a humectant and a keratolytic agent can be blended where necessary.

The dose of the fused aminodihydrothiazine derivative or pharmaceutically acceptable salt thereof according to the present invention varies according to the degree of symptoms, age, sex, body weight, mode of administration, type of salt and specific type of disease, for example. Typically, the active ingredient is orally administered to an adult at about 30 µg to 10 g, preferably 100 µg to 5 g, and more preferably 100 µg to 1 g per day, or is administered to an adult by injection at about 30 µg to 1 g, preferably 100 µg to 500 mg, and more preferably 100 µg to 300 mg per day, in one or several doses, respectively.

Compounds of formula (I) may be used in combination with other therapeutic agents, for example medicaments claimed to be useful as either disease modifying or symptomatic treatments of a neurodegenerative disease such as Alzheimer's disease. Thus, in a further aspect, the present invention provides a pharmaceutical product comprising, in combination, a first active ingredient which is a compound of formula (I) or a pharmaceutically acceptable salt thereof and at least one further active ingredient useful in treating a neurodegenerative disease. In one embodiment of the invention, the neurodegenerative disease is Alzheimer-type dementia (AD). Suitable examples of such further active ingredients may be symptomatic agents, for example those known to modify cholinergic transmission such as M1 and M3 muscarinic receptor agonists or allosteric modulators, M2 muscarinic antagonists, M4 agonists or positive allosteric modulators (PAMs), acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-$HT_4$ receptor agonists or partial agonists, histamine H3 antagonists, $5HT_{1A}$ receptor antagonists or $5HT_{1A}$ receptor ligands and NMDA receptor antagonists or modulators, 5-$HT_{2A}$ antagonists, 5-$HT_7$ antagonists, D1 agonists or PAMs, D4 agonists or PAMs, D5 agonists or PAMs, GABA-A α5 inverse agonists or negative allosteric modulators (NAMs), GABA-A α2/3 agonists or PAMs, mGluR2 modulators (PAMs or NAMs), mGluR3 PAMs, mGluR5 PAMs, PDE 1 inhibitors, PDE 2 inhibitors, PDE 4 inhibitors, PDE 5 inhibitors, PDE 9 inhibitors, PDE 10 inhibitors, GlyT1 inhibitors, DAAO inhibitors, ASC1 inhibitors, AMPA modulators, SIRT1 activators or inhibitors, AT4 antagonists, GalR1 antagonists, GalR3 ligands, adenosine A1 antagonists, adenosine A2a antagonists, α2A antagonists or agonists, selective and unselective norepinephrine reuptake inhibitors (SNRIs), or potential disease modifying agents such as gamma secretase inhibitors or modulators, alpha secretase activators or modulators, amyloid aggregation inhibitors, amyloid antibodies, tau aggregation inhibitors or tau phosphorylation/kinase inhibitors, tau dephosphorylation/phosphatase activators, mitogen-activated protein kinase kinase 4 (MKK4/MEK4/MAP2K4) inhibitors, c-Jun N-terminal kinase (JNK) inhibitors, casein kinase inhibitors, MK2 (mitogen activated protein kinase-activated protein kinase 2) inhibitors, MARK (microtubule affinity regulating kinase) inhibitors, CDK5 (cyclin dependent kinase 5) inhibitors, GSK-3 (glycogen synthase kinase-3) inhibitors and tau-tubulin kinase-1 (TTBK1) inhibitors. Further examples of such other therapeutic agents may be calcium channel blockers, HMG-CoA (3-hydroxy-3-methyl-glutaryl-CoA) reductase inhibitors (statins) and lipid lowering agents, NGF (nerve growth factor) mimics, antioxidants, GPR3 ligands, plasmin activators, neprilysin (NEP) activators, IDE (insulin degrading enzyme) activators, melatonin MT1 and/or MT2 agonists, TLX/NR2E1 (tailless X receptor) ligands, GluR1 ligands, RAGE (receptor for advanced glycation end-products) antagonists, EGFR (epidermal growth factor receptor) inhibitors, FPRL-1 (formyl peptide-like receptor-1) ligands, GABA antagonists, and MICAL (molecule interacting with casL) inhibitors, e.g. oxoreductase inhibitors, CB1 antagonists/inverse agonists, non-steroidal anti-inflammatory drugs (NSAIDs), anti-inflammatory agents (for example agents that could be used to treat neuroinflammation either by enhancing or reducing neuroinflammation), amyloid precursor protein (APP) ligands, anti-amyloid vaccines and/or antibodies, agents that promote or enhance amyloid efflux and/or clearance, histone deacetylase (HDAC) inhibitors, EP2 antagonists, 11-beta HSD1 (hydroxysteroid dehydrogenase) inhibitors, liver X receptor (LXR) agonists or PAMs, lipoprotein receptor-related protein (LRP) mimics and/or ligands and/or enhancers and/or inhibitors, butyryl cholinesterase inhibitors, kynurinic acid antagonists and/or inhibitors of kynurenine aminotransferease (KAT), orphanin FQ/nociceptin (NOP)/opioid-like receptor 1 (ORL1) antagonists, excitatory amino acid transporter (EAAT) ligands (activators or inhibitors), and plasminogen activator inhibitor-1 (PAI-1) inhibitors, niacin and/or GPR109 agonists or PAMs in combination with cholesterol lowering agents and/or HMGCoA reductase inhibitors (statins), dimebolin or similar agents, antihistamines, metal binding/chelating agents, antibiotics, growth hormone secretagogues, cholesterol lowering agents, vitamin E, cholesterol absorption inhibitors, cholesterol efflux promoters and/or activators, and insulin upregulating agents.

In one embodiment, the present invention provides a pharmaceutical product comprising, in combination, a first active ingredient which is a compound of formula (I) or a pharmaceutically acceptable salt thereof and at least one further active ingredient selected from:— cholinesterase inhibitors, e.g. donepezil, galantamine, rivastigamine, tetrahydroaminoacridine and pharmaceutically acceptable salts thereof, 5-$HT_6$ antagonists, e.g. SB-742457 and pharmaceutically acceptable salts thereof, HMGCoA reductase inhibitors e.g. lovastatin, rosuvastatin, atorvastatin, simvastatin, fluvastatin, pitavastatin, pravastatin and pharmaceutically acceptable salts thereof.

The individual components of such combinations may be administered either sequentially or simultaneously in separate or combined pharmaceutical formulations. Consequently, the pharmaceutical product may, for example be a pharmaceutical composition comprising the first and further active ingredients in admixture. Alternatively, the pharmaceutical product may for example comprise the first and further active ingredients in separate pharmaceutical preparations suitable for simultaneous, sequential or separate administration to a patient in need thereof.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention.

When a compound of formula (I) or a pharmaceutically acceptable salt thereof is used in combination with a second therapeutic agent active, the dose of each compound may differ from that when the compound is used alone. Appropriate doses will be readily appreciated by those skilled in the art.

Thus, an additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

In one embodiment, the present invention provides a pharmaceutical composition comprising a compound of formula (I), one or more other agents for the treatment of Alzheimer's disease such as symptomatic agents, for examples those known to modify cholinergic transmission such as M1 and M3 muscarinic receptor agonists or allosteric modulators, M2 muscarinic antagonists, acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-HT$_4$ receptor agonists or partial agonists, histamine H3 antagonists, 5-HT$_6$ receptor antagonists or 5HT1A receptor ligands and NMDA receptor antagonists or modulators, 5-HT$_{2A}$ antagonists, 5-HT$_7$ antagonists, D1 agonists or positive allosteric modulators (PAMs), D4 agonists or PAMs, GABA-A a5 inverse agonists or negative allosteric modulators (NAMs), GABA-A α2/3 agonists or PAMs, mGluR2 modulators (PAMs or NAMs), mGluR3 PAM, mGluR5 PAM, PDE 1 inhibitors, PDE 2 inhibitors, PDE 4 inhibitors, PDE 5 inhibitors, PDE 9 inhibitors, PDE 10 inhibitors, GlyT1 inhibitors, DAAO inhibitors, ASC1 inhibitors, AMPA modulators, SIRT1 activators or inhibitors, AT4 antagonists, GalR1 antagonists, GalR3 ligands, adenosine A1 antagonists, adenosine A2a antagonists, α2A antagonists or agonists, selective and unselective norepinephrine reuptake inhibitors (SNRIs), or potential disease modifying agents such as gamma secretase inhibitors or modulators, alpha secretase activators or modulators, amyloid aggregation inhibitors, amyloid antibodies, tau aggregation inhibitors or tau phosphorylation inhibitors, in association with a pharmaceutically acceptable carrier. In a further embodiment the present invention provides a combination comprising a compound of formula (I) or a pharmaceutically acceptable salt thereof, together with a further therapeutic agent as described herein above for sequential or simultaneous administration in separate or combined pharmaceutical formulations.

In a further aspect, the invention provides a method of inhibiting production of amyloid-β protein and/or of treating or preventing a neurodegenerative disease, such as Alzheimer-type dementia and Down's syndrome, the method involving administering to a human subject suffering from the condition a therapeutically or prophylactically effective amount of the pharmaceutical composition described above or of a compound of formula (I) as defined above, or a pharmaceutically acceptable salt thereof "Effective amount" means an amount sufficient to cause a benefit to the subject or at least to cause a change in the subject's condition.

Next, methods for preparing the compound of the formula (I) [hereinafter referred to as compound (I); a compound represented by another formula is similarly described] or pharmaceutically acceptable salt thereof according to the present invention will be described.

The compound represented by the formula (I):

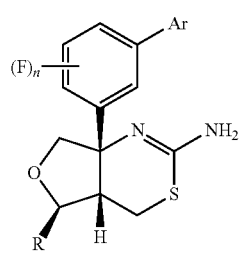

(I)

(wherein R, n and Ar are as defined above) or the intermediate thereof are synthesized by, for example, the General Preparation Methods described below.

1. General Preparation Method 1:

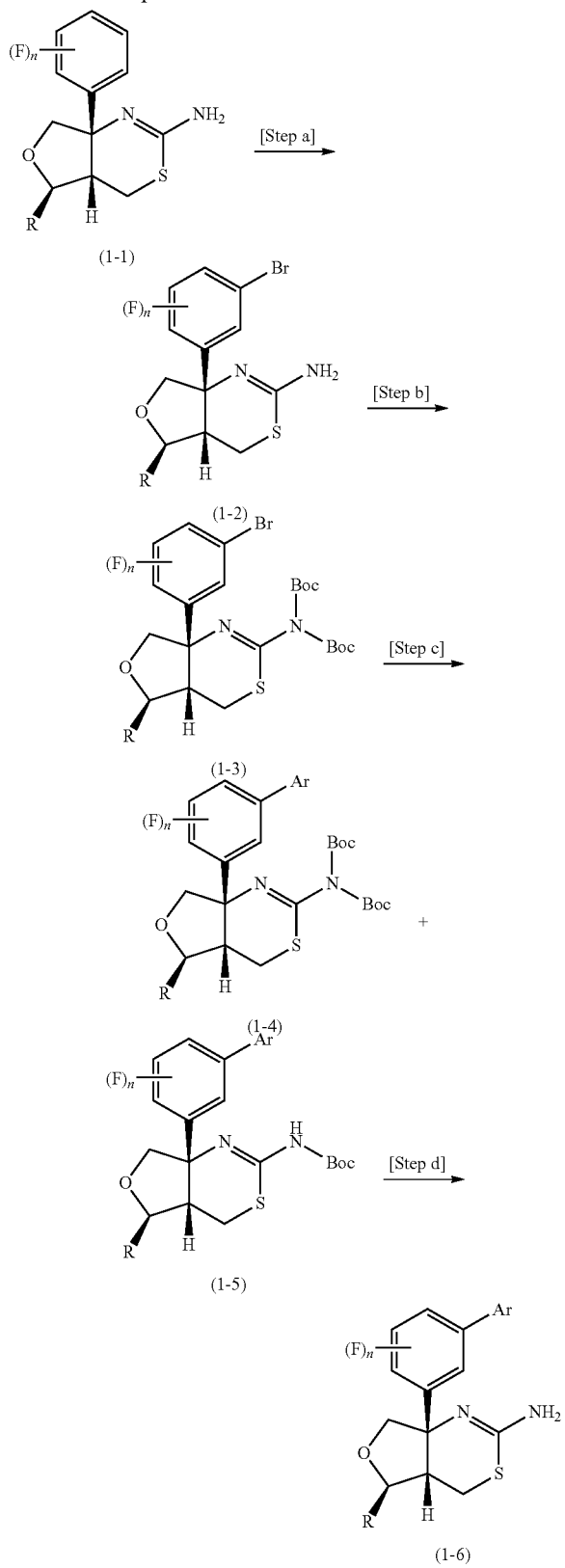

In the formula R, Ar and n are as defined above.

General Preparation Method 1 is a method for preparing a compound (1-6) which corresponds to compound (I) according to the present invention from a compound (1-1) as a raw material through multiple steps of Step a to Step d.

The compound (1-1) can be prepared as described in WO2009/091016.

Step a:

This step is a step of obtaining a compound (1-2) by bromination of compound (1-1) when R and n are defined as above.

The bromination may be carried out under various conditions, for example by reaction with a suitable brominating reagent, such as N-bromosuccinimide, in a suitable solvent, for example trifluoroacetic acid/sulfuric acid. The reaction may be carried out at various temperatures, for example at room temperature, or at elevated temperatures, for example 60° C.

Step b:

This step is a step of obtaining a compound (1-3) by t-butoxycarbonylation of the amino group of the compound (1-2) when R and n are defined as above.

The reaction can be performed under the same conditions as those generally used in t-butoxycarbonylation of an amino compound such as the conditions described in a document such as T. W. Green and P. G. M. Wuts, "Protective Groups in Organic Chemistry, Second Edition", John Wiley & Sons (1991), P. 327-330. The compound (1-3) can be obtained by reacting the compound (1-2) with di-tert-butyl dicarbonate using N,N-dimethylpyridin-4-amine as a base in a solvent such as dichloromethane, for example.

Step c:

This step is a step of obtaining compounds (1-4 and 1-5) from compound (1-3) by utilizing a transition metal-mediated coupling reaction when R, Ar and n are defined as above.

Those skilled in the art will appreciate that this transformation can be accomplished by a range of conditions. Those skilled in the art will also understand that these conditions may give products with one or two Boc groups (compounds 1-4 and 1-5). These may be produced in different ratios according to the reaction conditions. Those skilled in the art will also appreciate that these products may be isolated and treated separately in subsequent transformations or they be used together.

For example compound (1-3) can be transformed to (1-4 and 1-5) by using a transition metal catalyst, for example a palladium catalyst such as dichlorobis(triphenylphosphine) palladium or palladium dichloride with triphenylphosphine in a 1:2 ratio. Alternatively, a wide variety of related palladium catalysts may also be suitable for this transformation, for example tetrakis(triphenylphosphine)palladium and the like. Those skilled in the art will understand that many such catalysts are known and that many of such catalysts are capable of effecting this transformation and that the substrate (1-3) or the coupling partner may dictate which catalyst can or cannot be used.

The aforementioned transition metal mediated coupling reactions require a suitably functionalized reaction partner, examples include boronic acids/esters (eg Suzuki-Miyaura reaction; Pure Appl. Chem. 1991, 63, 419-422; Organometallic Chem, 1999, 576, 147-168; Chem. Rev., 1979, 95 (7): 2457-2483; J. Org. Chem. 2007, 72, 7207-7213; J. Am. Chem. Soc. 2000, 122, 4020-4028 and J. Org. Chem. 2007, 72, 5960-5967), stannanes (eg Stile reaction; J. Am. Chem. Soc. 1978, 100, 3636; Org. Synth., 1998, Coll. Vol. 9, 553; Angew. Chem. Int. Ed. Engl. 1986, 25, 508-524; Org. React. 1998, 50, 1-652 and J. Am, Chem. Soc. 1990, 112, 3093-3100), zinc reagents (eg Negishi reaction; J. Chem. Soc., Chem. Commun., 1977, 683; J. Org. Chem., 2008, 73, 7380-7382; J. Am. Chem. Soc., 2003, 125, 12527-12530) and even Grignard reagents (catalysed by palladium or nickel, e.g. Kumada coupling; J. Am. Chem. Soc. 1972, 94 (12), 4374-4376). Those skilled in the art will appreciate the intricacies of these reagents and which ones it is most appropriate to use.

In addition to the aforementioned catalyst and reaction partner, these transition-metal mediated reactions require a solvent and often a base is present. Suitable solvents include mixtures of water and DME or toluene and ethanol or toluene and water or toluene and DME or the like.

The reaction may be conducted at various temperatures, for example room temperature to 120° C., or for example 100° C.

Preferable examples of the organometallic catalyst include metal catalysts such as tetrakis(triphenylphosphine)palladium (0), dichlorobis(triphenylphosphine)palladium (II), [1,1'-bis(diphenylphosphino)ferrocene]palladium (II) dichloride, bis(tert-butylphosphine)palladium (0), palladium (II) acetate and [1,3-bis(diphenylphosphino)propane]nickel (II), and mixtures of these metal catalysts. The amount of the organometallic catalyst used is about 0.001 to 0.5 equivalent with respect to the raw material. The amount of the coupling partner, for example organoboron derivative, organostannane, organozinc and the like, used is not particularly limited and is usually 1 to 5 equivalents with respect to the compound (1-3). The solvent used in this reaction is not particularly limited insofar as it does not inhibit the reaction. Preferable examples of the solvent include benzene, toluene, xylene, N,N-dimethylformamide, 1-methyl-2-pyrrolidone, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 48 hours, and preferably 0.5 to 24 hours.

A more preferable result such as an improved yield may be achieved by carrying out this reaction in the presence of a base or a salt. Such a base or salt is not particularly limited. Preferable examples of the base or salt include bases or salts such as sodium carbonate, potassium carbonate, barium hydroxide, cesium carbonate, potassium phosphate, potassium fluoride and solutions thereof, and triethylamine, N,N-diisopropylethylamine, lithium chloride and copper (I) iodide.

Step d:

This step is a step of obtaining compound (1-6) using a deprotection reaction of the t-butoxycarbonyl group(s) of the compounds (1-4 and 1-5) when R, Ar and n are defined as above.

The reaction can be performed under the same conditions as those generally used in a deprotection reaction of a t-butoxycarbonyl group such as the conditions described in a document such as T. W. Green and P. G. M. Wuts, "Protective Groups in Organic Chemistry, Second Edition", John Wiley & Sons (1991), P. 327-330. The compound (1-6) can be obtained by reacting trifluoroacetic acid with the compound(s) (1-4 and 1-5) in a solvent such as dichloromethane, for example.

2. Alternative Method for the Preparation of Compound (1-6)

It will be appreciated by those skilled in the art that alternative methods exist for the transformation of compound (1-2) to compound (1-6). The nature of this transformation may involve more steps or less steps and may result in higher overall yields or lower overall yields and may or may not be substrate dependent. Those skilled in the art will appreciate these factors and select the most appropriate conditions for the aforementioned transformation.

One such alternative transformation is outlined below and described by step e to step g.

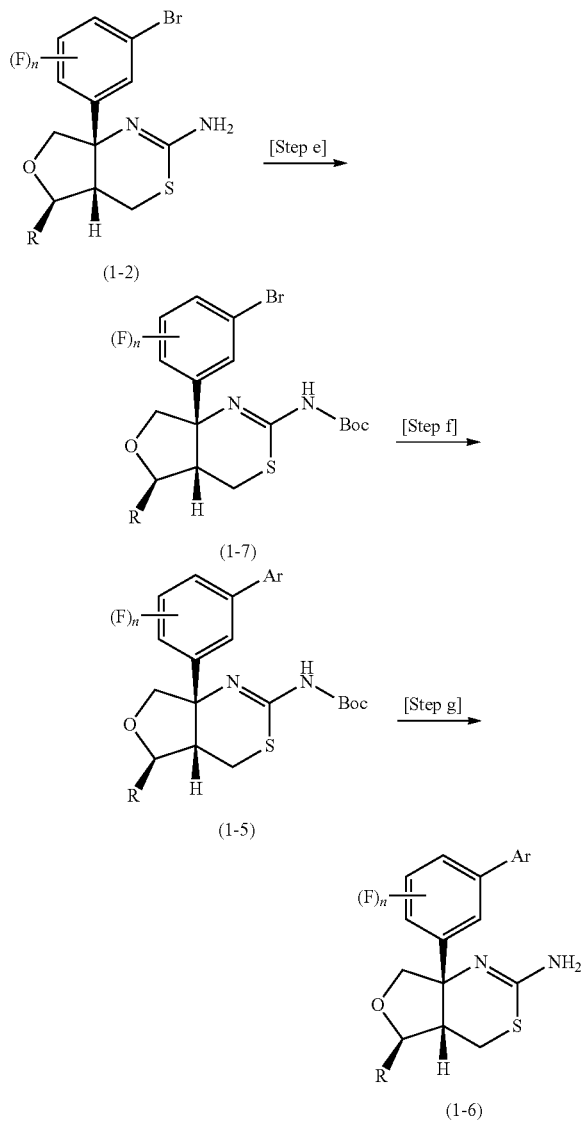

Step e:

This step is a step of obtaining a compound (1-7) by t-butoxycarbonylation of the amino group of the compound (1-2) when R and n are defined as above.

The reaction can be performed under the same conditions as those generally used in t-butoxycarbonylation of an amino compound such as the conditions described in a document such as T. W. Green and P. G. M. Wuts, "Protective Groups in Organic Chemistry, Second Edition", John Wiley & Sons (1991), P. 327-330. The compound (1-7) can be obtained by reacting the compound (1-2) with di-tert-butyl dicarbonate in a solvent such as tetrahydrofuran, for example. The reaction may be carried out at various temperatures, for example at room temperature, or at elevated temperatures, for example 80° C.

Step f:

This step is a step of obtaining compound (1-5) from compound (1-7) by utilizing a transition metal-mediated coupling reaction when R, Ar and n are defined as above.

Those skilled in the art will appreciate that this transformation can be accomplished by a range of conditions.

For example compound (1-7) can be transformed to (1-5) by using a transition metal catalyst, for example a palladium catalyst such as dichlorobis(triphenylphosphine)palladium or palladium dichloride with triphenylphosphine in a 1:2 ratio. Alternatively, a wide variety of related palladium catalysts may also be suitable for this transformation, for example tetrakis(triphenylphosphine)palladium and the like. Those skilled in the art will understand that many such catalysts are known and that many of such catalysts are capable of effecting this transformation and that the substrate (1-7) or the coupling partner may dictate which catalyst can or cannot be used.

The aforementioned transition metal mediated coupling reactions require a suitably functionalized reaction partner, examples include boronic acids/esters (eg Suzuki-Miyaura reaction; Pure Appl. Chem., 1991, 63, 419-422; Organometallic Chem. 1999, 576, 147-168; Chem. Rev., 1979, 95 (7): 2457-2483; J. Org. Chem. 2007, 72, 7207-7213; J. Am. Chem. Soc. 2000, 122, 4020-4028 and J. Org. Chem. 2007, 72, 5960-5967), stannanes (eg Stille reaction; J. Am. Chem. Soc. 1978, 100, 3636; Org. Synth., 1998, Coll. Vol. 9, 553; Angew. Chem. Int. Ed. Engl. 1986, 25, 508-524; Org. React. 1998, 50, 1-652 and J. Am, Chem. Soc. 1990, 112, 3093-3100), zinc reagents (eg Negishi reaction; J. Chem. Soc., Chem. Commun., 1977, 683; J. Org. Chem., 2008, 73, 7380-7382; J. Am. Chem. Soc., 2003, 125, 12527-12530) and even Grignard reagents (catalysed by palladium or nickel, eg Kumada coupling; J. Am. Chem. Soc. 1972, 94 (12), 4374-4376). Those skilled in the art will appreciate the intricacies of these reagents and which ones it is most appropriate to use.

In addition to the aforementioned catalyst and reaction partner, these transition-metal mediated reactions require a solvent and often a base is present. Suitable solvents include mixtures of water and DME or toluene and ethanol or toluene and water or toluene and DME or the like.

The reaction may be conducted at various temperatures, for example room temperature to 120° C., or for example 100° C.

Preferable examples of the organometallic catalyst include metal catalysts such as tetrakis(triphenylphosphine)palladium (0), dichlorobis(triphenylphosphine)palladium (II), [1,1'-bis(diphenylphosphino)ferrocene]palladium (II) dichloride, bis(tert-butylphosphine)palladium (0), palladium (II) acetate and [1,3-bis(diphenylphosphino)propane]nickel (II), and mixtures of these metal catalysts. The amount of the organometallic catalyst used is about 0.001 to 0.5 equivalent with respect to the raw material. The amount of the coupling partner, for example organoboron derivative, organostannane, organozinc and the like, used is not particularly limited and is usually 1 to 5 equivalents with respect to the compound (1-7). The solvent used in this reaction is not particularly limited insofar as it does not inhibit the reaction. Preferable examples of the solvent include benzene, toluene, xylene, N,N-dimethylformamide, 1-methyl-2-pyrrolidone, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 48 hours, and preferably 0.5 to 24 hours.

A more preferable result such as an improved yield may be achieved by carrying out this reaction in the presence of a base or a salt. Such a base or salt is not particularly limited. Preferable examples of the base or salt include bases or salts such as sodium carbonate, potassium carbonate, barium hydroxide, cesium carbonate, potassium phosphate, potassium fluoride and solutions thereof, and triethylamine, N,N-diisopropylethylamine, lithium chloride and copper (I) iodide.

Step g:

This step is a step of obtaining compound (1-6) using a deprotection reaction of the t-butoxycarbonyl group of the compound (1-5) when R, Ar and n are defined as above.

The reaction can be performed under the same conditions as those generally used in a deprotection reaction of a t-butoxycarbonyl group such as the conditions described in a document such as T. W. Green and P. G. M. Wuts, "Protective Groups in Organic Chemistry, Second Edition", John Wiley & Sons (1991), P. 327-330. The compound (1-6) can be obtained by reacting trifluoroacetic acid with the compound (1-5) in a solvent such as dichloromethane, for example.

3. Alternative Method for the Preparation of Compounds (1-4 and 1-5) from Compound (1-3)

It will be appreciated by those skilled in the art that alternative methods may exist for the preparation of compounds (1-4 and 1-5) from compound (1-3) and those skilled in the art will be able to ascertain when it is best to apply the aforementioned alternative conditions. An example of an alternative procedure is outlined below by step h to step j.

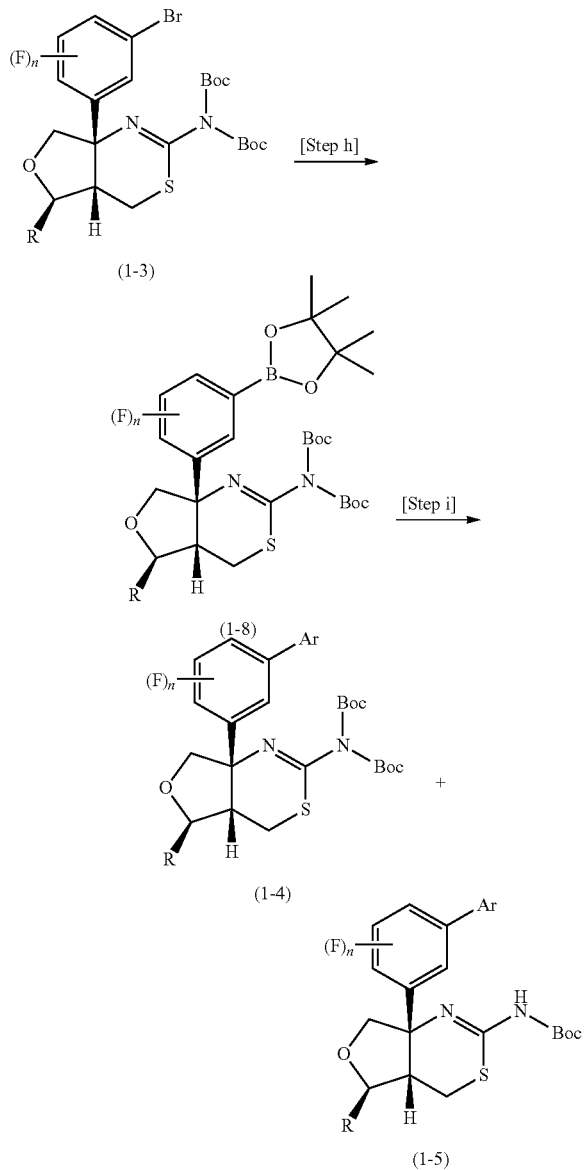

Step h:

This step is a step of obtaining compounds (1-8) from compound (1-3) by utilizing a transition metal-mediated coupling reaction when R and n are defined as above.

Those skilled in the art will appreciate that this transformation can be accomplished by a range of conditions.

For example compound (1-3) can be transformed to (1-8) by using a transition metal catalyst, for example a palladium catalyst such as 1,1'-bis(diphenylphosphino)ferrocenepalladium dichloride. Alternatively, a wide variety of related palladium and nickel catalysts may also be suitable for this transformation, for example tetrakis(triphenylphosphine)palladium, [1,3-Bis(diphenylphosphino)propane]dichloronickel (II) and the like. Those skilled in the art will understand that many such catalysts are known and that many of such catalysts are capable of effecting this transformation and that the substrate (1-3) or the coupling partner may dictate which catalyst can or cannot be used.

The aforementioned transition metal mediated coupling reactions require a suitably functionalized reaction partner, examples include bis(pinacolato)diboron (eg; J. Org. Chem. 1995, 60, 7508-7510) and 4,4,5,5-tetramethyl-1,3,2-dioxaborolane (eg, J. Org. Chem. 1997, 62, 6458-6459). Those skilled in the art will appreciate the intricacies of these reagents and which ones it is most appropriate to use.

In addition to the aforementioned catalyst and reaction partner, these transition-metal mediated reactions require a solvent. Suitable solvents include DMSO, DMF, toluene, dioxane or the like.

Frequently a salt or base is also present. Such a base or salt is not particularly limited. Preferable examples of the base or salt include bases or salts such as potassium acetate and triethylamine.

The reaction may be conducted at various temperatures, for example room temperature to 140° C., or for example 80° C. The reaction time is not particularly limited and is usually 0.5 to 48 hours, and preferably 0.5 to 24 hours.

Step i:

This step is a step of obtaining compounds (1-4 and 1-5) from compound (1-8) by utilizing a transition metal-mediated coupling reaction when R, Ar and n are defined as above.

Those skilled in the art will appreciate that this transformation can be accomplished by a range of conditions. Those skilled in the art will also understand that these conditions may give products with one or two Boc groups (compounds I-4 and 1-5). These may be produced in different ratios according to the reaction conditions. Those skilled in the art will also appreciate that these products may be isolated and treated separately in subsequent transformations or they be used together.

For example compound (1-8) can be transformed to (1-4 and 1-5) by using a transition metal catalyst, for example a palladium catalyst such as dichlorobis(triphenylphosphine) palladium or palladium dichloride with triphenylphosphine in a 1:2 ratio. Alternatively, a wide variety of related palladium catalysts may also be suitable for this transformation, for example tetrakis(triphenylphosphine)palladium and the like. Those skilled in the art will understand that many such catalysts known and that many of such catalysts are capable of effecting this transformation and that the substrate (1-8) or the coupling partner may dictate which catalyst can or cannot be used.

The aforementioned transition metal mediated coupling reactions require a suitably functionalized reaction partner, examples include aromatic halides (Metal-Catalyzed Cross-Coupling Reactions 1998, 49-97), aromatic sulfonates (Tet. Lett. 1997, 38(44), 7645-7648), aromatic diazonium compounds (Tet. Lett. 2000, 41(33), 6271-6274; Bulletin de la Societe Chimique de France 1996, 133(11), 1095-1102). Those skilled in the art will appreciate the intricacies of these reagents and which ones it is most appropriate to use.

In addition to the aforementioned catalyst and reaction partner, these transition-metal mediated reactions require a solvent and often a base is present. Suitable solvents include mixtures of water and DME or toluene and ethanol or toluene and water or toluene and DME or the like.

The reaction may be conducted at various temperatures, for example room temperature to 120° C., or for example 100° C.

Preferable examples of the organometallic catalyst include metal catalysts such as tetrakis(triphenylphosphine)palladium (0), dichlorobis(triphenylphosphine)palladium (II), [1,1'-bis(diphenylphosphino)ferrocene]palladium (II) dichloride, bis(tert-butylphosphine)palladium (0), palladium (II) acetate and [1,3-bis(diphenylphosphino)propane]nickel (II), and mixtures of these metal catalysts. The amount of the organometallic catalyst used is about 0.001 to 0.5 equivalent with respect to the raw material. The amount of the coupling partner, for example aromatic halide, aromatic sulfonate, aromatic diazonium compound and the like, used is not particularly limited and is usually 1 to 5 equivalents with respect to the compound (1-8). The solvent used in this reaction is not particularly limited insofar as it does not inhibit the reaction. Preferable examples of the solvent include benzene, toluene, xylene, N,N-dimethylformamide, 1-methyl-2-pyrrolidone, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 48 hours, and preferably 0.5 to 24 hours.

A more preferable result such as an improved yield may be achieved by carrying out this reaction in the presence of a base or a salt. Such a base or salt is not particularly limited. Preferable examples of the base or salt include bases or salts such as sodium carbonate, potassium carbonate, barium hydroxide, cesium carbonate, potassium phosphate, potassium fluoride and solutions thereof, and triethylamine, N,N-diisopropylethylamine, lithium chloride.

The present invention will be described more specifically below with reference to Examples, Preparation Examples and Test Example. However, the present invention is not limited thereto. The abbreviations used in Examples are conventional abbreviations known to a person skilled in the art. Some abbreviations are shown below.

Abbreviations

BOC & Boc: tert-butoxycarbonyl; br: broad; Bn: benzyl; Bu: butyl; BuLi: n-butyl lithium; d: doublet; DCM: dichloromethane; dd: doublet of doublets; DME: 1,2-dimethoxyethane; DMF (N,N-dimethylformamide); DMAP: (4-N,N-dimethylaminopyridine); DMSO (dimethylsulfoxide); EDC & EDAC: (N-3(-dimethylaminopropyl) N'ethylcarbodiimide hydrochloride); Et: ethyl; Et$_2$O: diethyl ether; EtOAc: ethyl acetate; EtOH: ethanol; h, hr, hrs: hours; IPA: isopropyl alcohol; HCl: hydrochloric acid; HPLC: high performance liquid chromatography; LCMS, LC/MS & LC-MS: liquid chromatography/mass spectrometry; m: multiplet; Me: methyl; MeCN: acetonitrile; MeOH: methanol; MS: mass spectrometry; MDAP: mass directed auto purification; min & mins: minutes; MTBE: methyl tert-butyl ether; NaOH: sodium hydroxide; NBS: N-bromosuccinimde; NMP: N-methylpyrrolidinone or 1-methyl-2-pyrrolidinone; NMR: nuclear magnetic resonance; Ph: phenyl; PhCH$_3$ & PhMe: toluene; Pr: propyl; Rt: retention time; RT, rt & r.t.: room temperature; s: singlet; SCX: strong cation exchange:—Isolute Flash SCX-2, Biotage; t: triplet; TBAF: tetrabutylammonium fluoride; TEA: triethylamine; THF: tetrahydrofuran; TFA: Trifluoroacetic acid; tlc: thin layer chromatography; UV (ultraviolet).

$^1$H NMR spectra were recorded on a Bruker AM series spectrometer operating at a (reported) frequency of 400 MHz. Chemical shifts in proton nuclear magnetic resonance spectra are recorded in δ units (ppm) relative to tetramethylsilane and coupling constants (J) are recorded in Hertz (Hz). Patterns are designated as s: singlet, d: doublet, t; triplet, br; broad.

The "room temperature" in the following Examples and Preparation Examples typically refers to about 10° C. to about 35° C. "%" indicates wt % unless otherwise specified.

Chemical names were generated from chemical structures using ChemBioDraw Ultra 11.0 and 12.0.

HPLC Conditions:
Analytical:
Method A: Agilent ZORBAX Eclipse XDB-C18, 4.6×150 mm, 5.0 μm, 1.5 mL per min, gradient 5-95% MeCN in water (0.1% formic acid) over 5.00 min—held for 3.00 min.

Purification:
Method B: Reverse phase HPLC (Phenomenex Luna C18, 250×50 mm, 10 um, 80 mL per min, gradient 35% to 100% (over 20 min) then 100% (5 min) MeCN in H$_2$O [0.1% acetic acid]).

Intermediate A: (±)-2-But-3-en-2-yloxy)-N-methoxy-N-methylacetamide

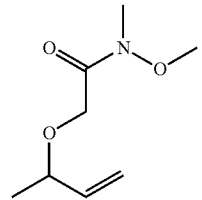

Step 1: (±)-tert-Butyl 2-(but-3-en-2-yloxy)acetate

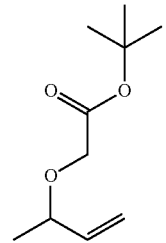

Tetrabutylammonium hydrogen sulfate (1.87 g, 5.51 mmol) was dissolved in 2-methoxy-2-methylpropane (32.18 ml). Maintaining the internal temperature <10° C., 25M NaOH in water (2.3 mL, 50% wt % aq sodium hydroxide) was added, followed by 3-buten-2ol (3.97 g, 55.1 mmol). Acetic acid bromo-1,1dimethyl ethyl ester (10.7 g, 55.0 mmol) was added, keeping the internal temperature 20-25° C. and the reaction was stirred for 1 hour at this temperature. Water (32.2 mL) and MTBE (64.4 mL) were added and the mixture was stirred vigorously for 15 minutes, then the layers allowed to separate. The organic layer was washed with water (6.1 mL) and MTBE (2×25 mL). The combined organics were concentrated (T<40° C., not less than 300 mBar) to leave the title product (10.1 g). $^1$H NMR (400 MHz, CDCl$_3$) δ ppm: 5.72

(ddd, J=7.71, 10.04, 17.37 Hz, 1H), 5.09-5.26 (m, 2H), 3.81-4.02 (m, 3H), 1.46-1.49 (m, 9H), 1.31 (d, J=6.32 Hz, 3H).

Step 2: (±)-2-But-3-en-2-yloxy)-N-methoxy-N-methylacetamide

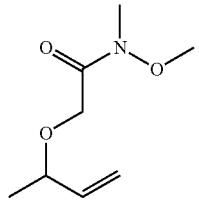

(±)-tert-Butyl 2-(but-3-en-2-yloxy)acetate (13.9 g, 74.8 mmol) was cooled over an ice bath and formic acid (50 mL, 74.8 mmol) was added. The solution was stirred at 0° C. for 15 minutes, before warming to room temperature and stirring for 4 hours. The formic acid was removed under vacuum and the residue was azeotroped with toluene (2×100 mL) to leave a yellow oil. This crude intermediate (9.9 g, 76.07 mmol) was dissolved in DCM (76 mL) and cooled to 0° C. N,N-Carbonyldiimidazole (14.19 g, 87.5 mmol) was added portionwise over 5 minutes. After stirring for a further 5 minutes at 0° C., N,O-dimethylhydroxylamine hydrochloride (7.04 g, 91.3 mmol) was added. The reaction was stirred at 0° C. for 10 minutes and allowed to warm to room temperature overnight. 2N HCl (100 mL) was added and stirred for 10 minutes. The mixture was extracted with DCM (3×50 mL), washed with saturated NaHCO₃ and concentrated in vacuo. The residue was filtered through a plug of silica (100 g), washing with EtOAc. The solvent was removed in vacuo to give the desired product as a clear oil (10.6 g). ¹H NMR (400 MHz, CDCl₃) δ ppm: 5.75 (ddd, J=7.71, 10.04, 17.37 Hz, 1H), 5.10-5.27 (m, 2H), 4.13-4.33 (m, 2H), 3.99 (quin, J=6.69 Hz, 1H), 3.67 (s, 3H), 3.18 (s, 3H), 1.33 (d, J=6.32 Hz, 3H).

EXAMPLE 1

(4aS,5R,7aS)-7a-(2-Fluoro-5-(pyrimidin-5-yl)phenyl)-5-methyl-4a,5,7,7a-tetrahydro-4H-furo[3,4-d][1,3]thiazin-2-amine

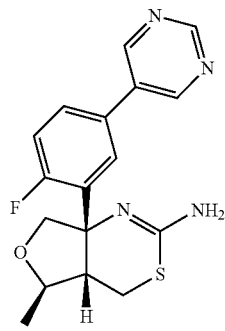 [SMILES: C[C@H]1OC[C@]2(c3cc(-c4cncnc4)ccc3F)N=C(N)SC[C@H]12]

Step 1: (4aS,5R,7aS)-7a-(5-bromo-2-fluorophenyl)-5-methyl-4a,5,7,7a-tetrahydro-4H-furo[3,4-d][1,3]thiazin-2-amine

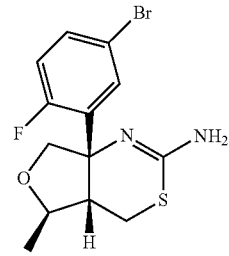 [SMILES: C[C@H]1OC[C@]2(c3cc(Br)ccc3F)N=C(N)SC[C@H]12]

(4aS,5R,7aS)-7a-(2-Fluorophenyl)-5-methyl-4a,5,7,7a-tetrahydro-4H-furo[3,4-d][1,3]thiazin-2-amine* (1.0 g, 3.75 mmol) was dissolved in trifluoroacetic acid (3.5 mL, 45.4 mmol). Sulfuric acid (1.2 mL, 22 mmol) was carefully added dropwise, keeping temperature below 30° C. N-Bromosuccinimide (0.74 g, 4.13 mmol) was added portionwise and the reaction was warmed to 55-60° C. After 30 minutes, the reaction was cooled to room temperature and added dropwise to a cooled solution of sodium hydroxide (3.00 g, 75.1 mmol) in water (25 mL). The solution of reaction mixture in sodium hydroxide solution was extracted with EtOAc (×2), checking the pH to ensure the TFA/H₂SO₄ had all been neutralised. The organic layer was washed with brine and concentrated to leave a brown solid. The solid was recrystalised from IPA (10 mL): heating to 50° C. for 15 minutes on the rotavap under slight vacuum. The suspension was cooled to room temperature, filtered and washed with IPA (2 mL) and heptane (10 mL). The solid was dried overnight to give the title compound (1.30 g). ¹H NMR (400 MHz, CDCl₃) δ ppm: 7.55 (dd, J=7.2, 2.7 Hz, 1H), 7.36 (ddd, J=8.7, 4.2, 2.5 Hz, 1H), 6.94 (dd, J=11.6, 8.6 Hz, 1H), 4.55 (dd, J=8.8, 1.3 Hz, 1H), 4.35 (q, J=1.0 Hz, 1H), 3.77 (dd, J=8.8, 2.3 Hz, 1H), 3.07 (dd, J=13.4, 3.5 Hz, 1H), 2.71 (dd, J=13.3, 3.9 Hz, 1H), 2.44-2.53 (m, 1H), 1.37 (d, J=6.1 Hz, 3H)

* Prepared as described in example 7, US2009/0209755 A1

Step 2: di-tert-Butyl[(4aS,5R,7aS)-7a-(5-bromo-2-fluorophenyl)-5-methyl-4a,5,7,7a-tetrahydro-4H-furo[3,4-d][1,3]thiazin-2-yl]imidodicarbonate

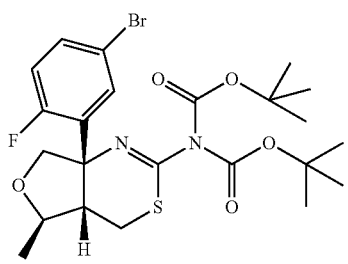 [SMILES: C[C@H]1OC[C@]2(c3cc(Br)ccc3F)N=C(N(C(=O)OC(C)(C)C)C(=O)OC(C)(C)C)SC[C@H]12]

(4aS,5R,7aS)-7a-(5-Bromo-2-fluorophenyl)-5-methyl-4a,5,7,7a-tetrahydro-4H-furo[3,4-d][1,3]thiazin-2-amine (2.10 g, 6.07 mmol) was dissolved in DCM (10 mL). To the reaction was added di-tert butyl dicarbonate (6.63 g, 30.4 mmol) and N,N-dimethylpyridin-4-amine (2.23 g, 18.2 mmol). The reaction mixture was stirred at room temperature overnight then partitioned between saturated aqueous NaHCO₃ and DCM.

The layers were separated and the aqueous layer extracted with DCM (×2). The combined organic layers were dried (MgSO₄), filtered and evaporated. The residue was purified by column chromatography, (gradient 0% to 40% EtOAc in hexane) to give the title compound (1.63 g). $^1$H NMR (400 MHz, CDCl₃) δ ppm: 7.54 (dd, J=7.07, 2.53 Hz, 1 H), 7.40 (ddd, J=8.59, 3.92, 2.65 Hz, 1 H), 6.99 (dd, J=11.62, 8.84 Hz, 1 H), 4.61 (d, J=9.35 Hz, 1 H), 4.26-4.36 (m, 1 H), 3.85 (dd, J=9.22, 2.15 Hz, 1 H), 3.09 (dd, J=13.64, 3.03 Hz, 1 H), 2.75 (dd, J=13.64, 3.54 Hz, 1 H), 2.55 (dt, J=9.35, 3.28 Hz, 1 H), 1.53-1.60 (s, 18 H), 1.40 (d, J=6.06 Hz, 3 H).

Step 3: N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-(difluoromethyl)pyrazine-2-carboxamide

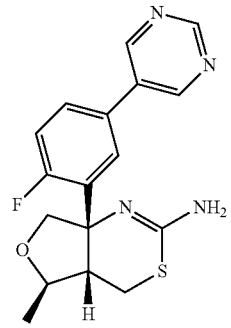 [SMILES: C[C@H]1OC[C@]2(c3cc(-c4cncnc4)ccc3F)N=C(N)SC[C@H]12]

di-tert-Butyl[(4aS,5R,7aS)-7a-(5-bromo-2-fluorophenyl)-5-methyl-4a,5,7,7a-tetrahydro-4H-furo[3,4-d][1,3]thiazin-2-yl]imidodicarbonate (0.15 g, 0.28 mmol) was dissolved in 1,2-dimethoxyethane (1.5 mL), water (0.7 mL) and ethanol (0.5 mL). The resulting solution was heated to 100° C. and to it was added pyrimidin-5-ylboronic acid (0.23 g, 1.9 mmol), cesium carbonate (0.538 g, 1.65 mmol) and dichloropalladium-triphenylphosphane (0.039 g, 0.055 mmol) and the reaction was stirred at 100° C. After 1 hour, the reaction mixture was cooled to room temperature, diluted with saturated aqueous NaHCO₃ and extracted with EtOAc (×3). The combined organic layers were dried (MgSO₄), filtered and concentrated in vacuo. The residue was purified using column chromatography, (gradient 0-100% EtOAc in hexane) to give the bis boc product (60 mg) and mono boc product (40 mg). $^1$H NMRs were consistent with desired structures. The products were combined in DCM (2 mL) and trifluoroacetic acid (2 mL). After 1 hour, the solvents were removed in vacuo. The residue was neutralised with saturated aqueous NaHCO₃ and extracted with DCM (×2). The combined organic layers were dried (MgSO₄), filtered and concentrated to leave the title compound (50 mg). $^1$H NMR (400 MHz, CDCl₃) δ ppm: 9.22 (s, 1H), 8.94 (s, 2H), 7.66 (dd, J=7.7, 2.4 Hz, 1H), 7.47 (ddd, J=1.0 Hz 1H), 7.23 (dd, J=11.7, 8.5 Hz, 1H), 4.66 (d, J=9.1 Hz, 1H), 4.35-4.41 (m, 1H), 3.84 (d, J=8.1 Hz, 1H), 3.10 (dd, J=13.5, 3.7 Hz, 1H), 2.77 (dd, J=13.4, 4.0 Hz, 1H), 2.53-2.63 (m, 1H), 1.40 (d, J=6.1 Hz, 3H)

EXAMPLE 2

(4aS,5R,7aS)-7a-(2-Fluoro-5-(1H-imidazo-2-yl)phenyl)-5-methyl-4a,5,7,7a-tetrahydro-4H-furo[3,4-d][1,3]thiazin-2-amine

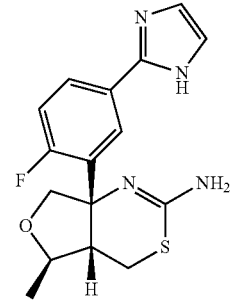 [SMILES: C[C@H]1OC[C@]2(c3cc(-c4ncc[nH]4)ccc3F)N=C(N)SC[C@H]12]

Step 1: di-tert-Butyl {(4aS,5R,7aS)-7a-[2-fluoro-5-(4,4,5,5-tetramethyl-1,3,2-dioxaborolan-2-yl)phenyl]-5-methyl-4a,5,7,7a-tetrahydro-4H-furo[3,4-d][1,3]thiazin-2-yl}imidodicarbonate

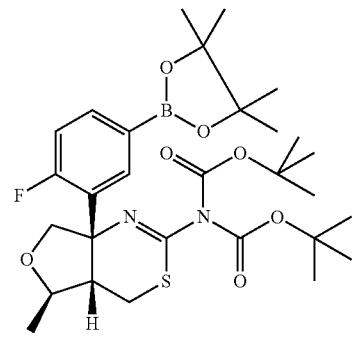 [SMILES: C[C@H]1OC[C@]2(c3cc(B4OC(C)(C)C(C)(C)O4)ccc3F)N=C(N(C(=O)OC(C)(C)C)C(=O)OC(C)(C)C)SC[C@H]12]

di-tert-Butyl [(4aS,5R,7aS)-7a-(5-bromo-2-fluorophenyl)-5-methyl-4a,5,7,7a-tetrahydro-4H-furo[3,4-d][1,3]thiazin-2-yl]imidodicarbonate (0.9 g, 1.7 mmol) was dissolved in dry dimethylsulfoxide (3 mL). To the stirred solution was added 4,4,4',4',5,5,5',5'-octamethyl-2,2'-bi-1,3,2-dioxaborolane (4.19 g, 16.5 mmol), potassium acetate (0.65 g, 6.6 mmol) and 1,1'-bis(diphenylphosphino)ferrocene-palladium (II)dichloride dichloromethane complex (0.12 g, 0.17 mmol). The reaction mixture was stirred at 80° C. for 3 hours. The reaction mixture was cooled to room temperature and partitioned between saturated aqueous NH₄Cl and EtOAc and the layers were separated. The aqueous layer was extracted with EtOAc (×2) and the combined organics were dried (MgSO₄), filtered and concentrated. The residue was purified using column chromatography, eluting with DCM to give the title compound (0.5 g colourless foam).

$^1$H NMR (400 MHz, CDCl₃) δ ppm: 7.73-7.82 (m, 2 H), 7.08 (dd, J=12.5, 8.2 Hz, 1 H), 4.58 (d, J=9.1 Hz, 1 H), 4.30-4.39 (m, 1 H), 3.88 (d, J=7.8 Hz, 1 H), 3.14 (dd, J=13.4, 2.8 Hz, 1 H), 2.74 (dd, J=13.5, 3.4 Hz, 1 H), 2.57-2.66 (m, J=9.3 Hz, 1 H), 1.48-1.59 (m, 18 H), 1.41 (d, J=6.1 Hz, 3 H), 1.32 (s, 12 H)

Step 2: 2-Iodo-1-((2-trimethylsilyl)ethoxy)methyl)-1H-imidazole

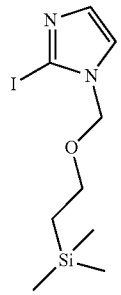

To a solution of 2-iodo-1H-imidazole (0.2 g, 1.0 mmol) in DMF (10 mL) was added sodium hydride (60% dispersion in oil, 83 mg, 2.0 mmol) and the subsequent reaction mixture was stirred at 40° C. for 2 hours. [2-(Chloromethoxy)ethyl](trimethyl)silane (0.37 mL, 2.1 mmol) was added and the reaction stirred at 40° C. for a further 5 hours. The reaction mixture was partitioned between EtOAc and water and the layers separated. The aqueous layers was extracted with EtOAc (×2) and the combined organic layers were dried (MgSO$_4$), filtered and concentrated in vacuo. The reaction mixture was purified by purification method B to give the title compound (73 mg). $^1$H NMR (400 MHz, CDCl$_3$) δ ppm: 7.15 (dd, J=10.0, 1.1 Hz, 2 H), 5.24 (s, 2 H), 3.54 (t, J=1.0 Hz, 2 H), 0.93 (t, J=1.0 Hz, 2 H), 0.01 (s, 9 H)

Step 3: (4aS,5R,7aS)-7a-(2-fluoro-5-(1H-imidazol-2-yl)phenyl)-5-methyl-4a,5,7,7a-tetrahydro-4H-furo[3,4-d][1,3]thiazin-2-amine

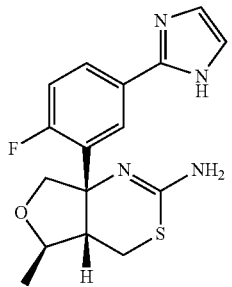 [SMILES: C[C@H]1OC[C@]2(c3cc(-c4ncc[nH]4)ccc3F)N=C(N)SC[C@H]12]

di-tert-Butyl{(4aS,5R,7aS)-7a-[2-fluoro-5-(4,4,5,5-tetramethyl-1,3,2-dioxaborolan-2-yl)phenyl]-5-methyl-4a,5,7,7a-tetrahydro-4H-furo[3,4-d][1,3]thiazin-2-yl}imidodicarbonate (0.1 g, 0.17 mmol) was dissolved in 1,2-dimethoxyethane (1.5 mL), water (0.7 mL) and ethanol (0.5 mL). The resulting solution was heated to 100° C. and to it was added 2-iodo-1-{[2-(trimethylsilyl)ethoxy]methyl}-1H-imidazole (0.1 g, 0.31 mmol), cesium carbonate (0.33 g, 1.0 mmol) and dichloropalladium-triphenylphosphane (0.02 g, 0.03 mmol) and the reaction was stirred at 100° C. for 1 hour. The reaction mixture was cooled to room temperature, diluted with saturated aqueous NaHCO$_3$ and extracted with EtOAc (×3). The combined organic layers were dried (MgSO$_4$), filtered and concentrated in vacuo. The residue was purified using column chromatography (gradient 0-100% EtOAc in hexane) to give a mixture of mono and bis BOC products. $^1$H NMRs consistent with desired structures. The residues were combined and dissolved in DCM (2 mL). Trifluoroacetic acid (1 mL) was added and the solution stirred at room temperature for 1 hour. The solvents were removed in vacuo and saturated aqueous NaHCO$_3$ added. The solution was extracted with DCM (×3). The combined organics were dried (MgSO$_4$), filtered and concentrated to give the title compound (48 mg). $^1$H NMR (400 MHz, CDCl$_3$) δ ppm: 7.76-7.89 (m, 2 H), 7.06-7.13 (m, 3 H), 4.57 (d, J=9.1 Hz, 1 H), 4.32-4.40 (m, 1 H), 3.81 (dd, J=8.8, 1.8 Hz, 1 H), 3.07 (dd, J=13.4, 3.5 Hz, 1 H), 2.71 (dd, J=13.3, 3.9 Hz, 1 H), 2.57-2.64 (m, 1 H), 1.37 (d, J=6.1 Hz, 3 H)

EXAMPLE 3

(4aS,5R,7aS)-7a-(2-fluoro-5-(2-(pyrazin-2-yl)-1H-imidazol-5-yl)phenyl)-5-methyl-4a,5,7,7a-tetrahydro-4H-furo[3,4-d][1,3]thiazin-2-amine

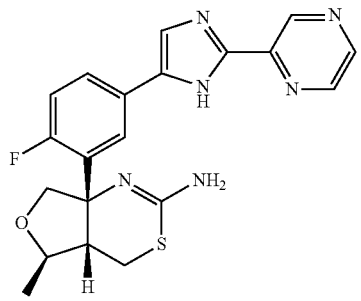 [SMILES: C[C@H]1OC[C@]2(c3cc(-c4cnc(-c5cnccn5)[nH]4)ccc3F)N=C(N)SC[C@H]12]

Step 1: 2-(1H-Imidazol-2-yl)pyrazine

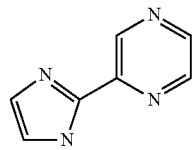 [SMILES: c1cnc(-c2ncc[nH]2)cn1]

2,2-Diethoxyethanamine (3 g, 2.25 mmol) was dissolved in dry methanol (20 mL). To this was added sodium methoxide (1.22 g, 22.5 mmol, as a 25% solution in methanol). After stirring for 25 minutes at room temperature, pyrazine-2-carbonitrile (2.37 g, 22.5 mmol) and acetic acid (1.35 g, 22.5 mmol) were added and the subsequent solution was stirred at 50° C. for 1 hour. MeOH (40 mL) and 6N HCl (12 mL) were added and the reaction was stirred at reflux overnight. The reaction mixture was cooled to room temperature and partitioned between 1:1 Et$_2$O and water (60 mL) and the layers were separated. The aqueous layer was basified to pH 9/10 and extracted with 10% MeOH in DCM. The combined organic extracts were dried (MgSO$_4$), filtered and concentrated to give the desired compound (1.49 g yellow solid). $^1$H NMR (400 MHz, MeOH-d$_4$) δ ppm: 7.67 (s, 1 H), 7.09 (d, J=1.8 Hz, 1 H), 6.99 (d, J=2.5 Hz, 1 H), 5.72 (s, 2 H)

Step 2: 2-(1-{[2-(Trimethylsilyl)ethoxy]methyl}-1H-imidazol-2-yl)pyrazine

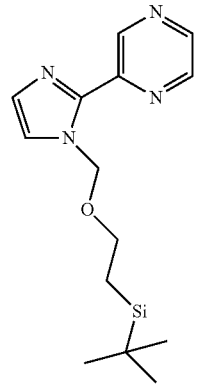

To a solution of 2-(4H-imidazol-2-yl)pyrazine (0.75 g, 5.1 mmol) in DMF (7 mL) was added sodium hydride (60% dispersion in oil, 0.42 g, 10.3 mmol) and the reaction stirred at 40° C. for 2 hours. [2-(chloromethoxy)ethyl](trimethyl) silane (1.71 g, 10.3 mmol) was added and the reaction was stirred at 40° C. for a further 3 hours The reaction mixture was partitioned between EtOAc and water and the layers separated. The aqueous layers was extracted with EtOAc (×2) and the combined organic layers were dried (MgSO$_4$), filtered and concentrated in vacuo. The residue was purified using column chromatography (gradient 20-60% EtOAc in hexane) to give the title compound (0.88 g, yellow oil). $^1$H NMR (400 MHz, CDCl$_3$) δ ppm: 9.47 (d, J=1.0 Hz, 1 H), 8.36-8.59 (m, 2 H), 7.26-7.28 (m, 1 H), 7.24 (d, J=1.3 Hz, 1 H), 5.96-6.00 (m, 2 H), 3.53-3.61 (m, 2 H), 0.86-0.94 (m, 2 H), −0.10-−0.05 (m, 9 H).

Step 3: 2-(5-Bromo-1-{[2-(trimethylsilyl)ethoxy]methyl}-1H-imidazol-2-yl)pyrazine and 2-(4-bromo-1-{[2-(trimethylsilyl)ethoxy]methyl}-1H-imidazol-2-pyrazine

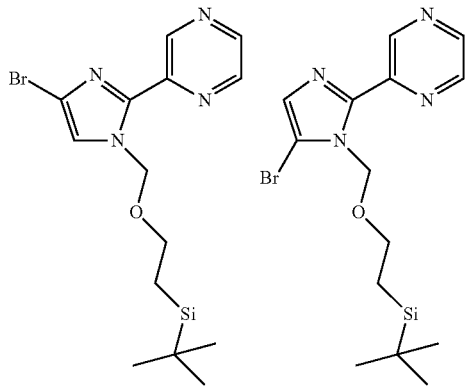

Potassium carbonate (0.1 g, 0.72 mmol) was added to a solution of 2-(1-{[2-(trimethylsilyl)ethoxy]methyl}-1H-imidazol-2-yl)pyrazine (0.1 g, 0.36 mmol) in dry THF (1 mL). Bromine (0.05 g, 0.33 mmol) was dissolved in dry THF (1 mL) and this solution was added dropwise to the reaction mixture. After 2 hours at room temperature, an additional aliquot of bromine (8 μL, 0.16 mmol) in 1 mL THF was added dropwise to the reaction. After 1 hour a further aliquot of bromine (8 μL, 0.16 mmol) was added. The reaction was partitioned between saturated aqueous NaHCO$_3$ and 10% MeOH in DCM. The layers were separated and the aqueous layer was extracted with 10% MeOH in DCM (×2). The combined organic layers were dried (MgSO$_4$), filtered and concentrated in vacuo. The residue was purified by column chromatography (gradient 0-60% EtOAc in hexane) to give a mixture of the title compounds (60 mg, purple oil).

$^1$H NMR (400 MHz, MeOH-d$_4$) δ ppm: 9.22 (d, J=1.3 Hz, 1 H), 8.66 (dd, J=2.5, 1.5 Hz, 1 H), 8.59 (d, J=2.5 Hz, 1 H), 7.53 (s, 1 H), 5.94 (s, 2 H), 3.56-3.63 (m, 2 H), 0.77-0.87 (m, 2 H), −0.13-−0.08 (m, 9 H)

$^1$H NMR (400 MHz, MeOH-d$_4$) δ ppm: 9.24 (d, J=1.5 Hz, 1 H), 8.66-8.71 (m, 1 H), 8.60 (d, J=2.5 Hz, 1 H), 7.25 (s, 1 H), 6.07 (s, 2 H), 3.58 (t, J=7.7 Hz, 2 H), 0.81 (t, J=7.8 Hz, 2 H), −0.14-−0.11 (m, 9 H)

Step 4: (4aS,5R,7aS)-7a-(2-Fluoro-5-(2-(pyrazin-2-yl)-1H-imidazol-5-yl)phenyl)-5-methyl-4a,5,7,7a-tetrahydro-4H-furo[3,4-d][1,3]thiazin-2-amine

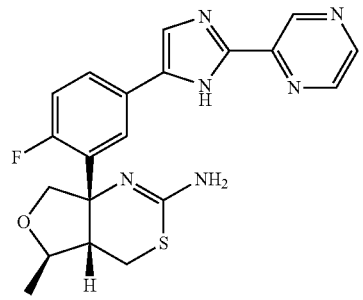 [SMILES: C[C@H]1OC[C@]2(c3cc(-c4cnc(-c5cnccn5)[nH]4)ccc3F)N=C(N)SC[C@H]12]

di-tert-Butyl {(4aS,5R,7aS)-7a-[2-fluoro-5-(4,4,5,5-tetramethyl-1,3,2-dioxaborolan-2-yl)phenyl]-5-methyl-4a,5,7,7a-tetrahydro-4H-furo[3,4-d][1,3]thiazin-2-yl}imidodicarbonate (0.1 g, 0.17 mmol) was dissolved in dry methanol (1 mL) and dry toluene (1 mL). To the solution was added 2-(5-bromo-1-{[2-(trimethylsilyl)ethoxy]methyl}-1H-imidazol-2-yl)pyrazine (mixture of isomers) (0.054 g, 0.15 mmol), palladium-triphenylphosphine (1:4) (0.020 g, 0.02 mmol) and Na$_2$CO$_3$ (0.33 mL, 1M solution in water) and the reaction was stirred at reflux in a sealed tube overnight. The reaction mixture was partitioned between saturated aqueous NaHCO$_3$ and DCM and the layers separated. The aqueous layer was extracted with DCM (×2) and the combined organics were dried (MgSO$_4$), filtered and concentrated in vacuo. The residue was purified by column chromatography (0-15% MeOH in DCM). The product, (4aS,5R,7aS)-7a-{2-fluoro-5-[2-(pyrazin-2-yl)-1-{[2-(trimethylsilyl)ethoxy]methyl}-1H-imidazol-5-yl]phenyl}-5-methyl-4a,5,7,7a-tetrahydro-4H-furo[3,4-d][1,3]thiazin-2-amine was dissolved in EtOH (5 mL) and CHCl (2 mL) and the reaction was stirred at reflux overnight to remove the SEM protecting group. The reaction mixture was concentrated in vacuo and loaded onto a SCX ion exchange cartridge washing with MeOH followed by 2N NH$_3$ in MeOH. The basic fraction was concentrated in vacuo. The residue was purified by column chromatography (gradient 0-15% MeOH in EtOAc) to afford the title compound (15 mg, yellow film). $^1$H NMR (400 MHz, MeOH-d$_4$) δ ppm: 9.32 (s, 1 H), 8.65 (t, J=1.0 Hz, 1 H), 8.54 (d, J=2.5 Hz, 1 H), 7.73-8.01 (m, 2 H), 7.58 (br. s., 1 H), 7.17 (dd, J=12.1, 8.6 Hz, 1 H), 4.63 (d, J=9.1 Hz, 1 H), 4.30-4.40 (m, 1 H), 3.82 (dd, J=8.6, 2.3 Hz, 1 H), 3.16 (dd, J=13.5, 3.9 Hz, 1 H), 2.88 (dd, J=13.4, 4.0 Hz, 1 H), 2.61 (dt, J=8.3, 4.1 Hz, 1 H), 1.34 (d, J=6.1 Hz, 3 H).

EXAMPLE 4

(4aS,5R,7aS)-7a-(2-Fluoro-5-(pyridin-3-yl)phenyl)-5-methyl-4a,5,7,7a-tetrahydro-4H-furo[3,4-d][1,3]thiazin-2-amine

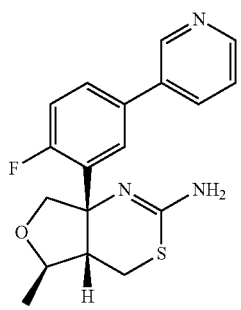 [SMILES: C[C@H]1OC[C@]2(c3cc(-c4cccnc4)ccc3F)N=C(N)SC[C@H]12]

This material was prepared using the procedures described in Example 1, replacing pyrimidin-5-ylboronic acid with the appropriate boronic acid.

¹H NMR (400 MHz, CDCl₃) δ ppm: 8.83 (d, J=1.8 Hz, 1 H), 8.60 (dd, J=4.8, 1.5 Hz, 1 H), 7.85 (dt, J=8.0, 1.9 Hz, 1 H), 7.63 (dd, J=7.7, 2.4 Hz, 1 H), 7.46 (ddd, J=8.4, 4.4, 2.4 Hz, 1 H), 7.36 (dd, J=7.8, 4.8 Hz, 1 H), 7.17 (dd, J=11.9, 8.3 Hz, 1 H), 4.66 (d, J=8.8 Hz, 1 H), 4.23-4.46 (m, 1 H), 3.84 (d, J=8.8 Hz, 1 H), 3.12 (dd, J=13.4, 3.8 Hz, 1 H), 2.75 (dd, J=13.4, 4.0 Hz, 1 H), 2.52-2.62 (m, 1 H), 1.38 (d, J=6.1 Hz, 3 H)

EXAMPLE 5

(4aS,5R,7aS)-7a-(4-Fluoro-[1,1'-biphenyl]-3-yl)-5-methyl-4a,5,7,7a-tetrahydro-4H-furo[3,4-d][1,3]thiazin-2-amine

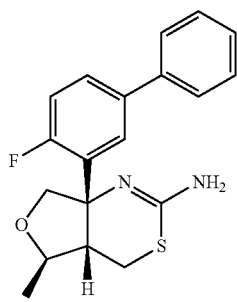 [SMILES: C[C@H]1OC[C@]2(c3cc(-c4ccccc4)ccc3F)N=C(N)SC[C@H]12]

This material was prepared using the procedures described in Example 1, replacing pyrimidin-5-ylboronic acid with the appropriate boronic acid.

¹H NMR (400 MHz, CDCl₃) δ ppm: 7.62 (dd, J=7.8, 2.3 Hz, 1 H), 7.53-7.58 (m, 2 H), 7.40-7.50 (m, 3 H), 7.36 (d, J=7.3 Hz, 1 H), 7.13 (dd, J=11.9, 8.3 Hz, 1 H), 4.66 (dd, J=9.0, 0.9 Hz, 1 H), 4.33-4.43 (m, 1 H), 3.91 (dd, J=9.0, 1.9 Hz, 1 H), 3.15 (dd, J=13.4, 3.8 Hz, 1 H), 2.76 (dd, J=13.4, 4.0 Hz, 1 H), 2.65 (dt, J=8.1, 3.9 Hz, 1 H), 1.39 (d, J=6.1 Hz, 3 H)

EXAMPLE 6

(4aS,5R,7aS)-7a-(2',4-difluoro-[1,1'-biphenyl]-3-yl)-5-methyl-4a,5,7,7a-tetrahydro-4H-furo[3,4-d][1,3]thiazin-2-amine

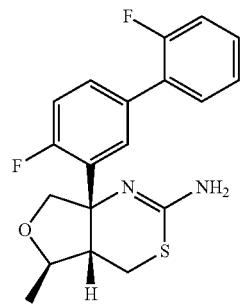 [SMILES: C[C@H]1OC[C@]2(c3cc(-c4ccccc4F)ccc3F)N=C(N)SC[C@H]12]

This material was prepared using the procedures described in Example 1, replacing pyrimidin-5-ylboronic acid with the appropriate boronic acid.

¹H NMR (400 MHz, CDCl₃) δ ppm: 7.56 (dd, J=1.0 Hz, 1 H), 7.40-7.49 (m, 2 H), 7.29-7.36 (m, 1 H), 7.21 (td, J=7.5, 1.0 Hz, 1 H), 7.11-7.17 (m, 2 H), 4.65 (dd, J=9.1, 0.8 Hz, 1 H), 4.32-4.43 (m, 1 H), 3.90 (dd, J=9.0, 1.9 Hz, 1 H), 3.16 (dd, J=13.4, 3.8 Hz, 1 H), 2.77 (dd, J=13.3, 3.9 Hz, 1 H), 2.57-2.66 (m, 1 H), 1.39 (d, J=6.1 Hz, 3 H)

EXAMPLE 7

(4aS,5R,7aS)-7a-(2-Fluoro-5-(2-fluoropyridin-3-yl)phenyl)-5-methyl-4a,5,7,7a-tetrahydro-4H-furo[3,4-d][1,3]thiazin-2-amine This material was prepared using the procedures described in Example 1, replacing pyrimidin-5-ylboronic acid with the appropriate boronic acid.

¹H NMR (400 MHz, CDCl₃) δ ppm: 8.20 (d, J=4.5 Hz, 1 H), 7.86 (ddd, J=9.8, 7.6, 1.8 Hz, 1 H), 7.59 (dd, J=1.0 Hz, 1 H), 7.48 (ddd, J=6.3, 4.3, 2.0 Hz, 1 H), 7.27-7.32 (m, 1 H), 7.16 (dd, J=11.9, 8.3 Hz, 1 H), 4.64 (d, J=1.0 Hz, 1 H), 4.32-4.42 (m, J=6.6, 6.6, 6.6, 6.6 Hz, 1 H), 3.85 (dd, J=8.8, 2.0

Hz, 1 H), 3.13 (dd, J=13.4, 3.8 Hz, 1 H), 2.76 (dd, J=13.4, 4.0 Hz, 1 H), 2.52-2.61 (m, 1 H), 1.38 (d, J=6.1 Hz, 3 H)

EXAMPLE 8

(4aS,5R,7aS)-7a-(2-fluoro-5-(5-methoxypyridin-3-yl)phenyl)-5-methyl-4a,5,7,7a-tetrahydro-4H-furo[3,4-d][1,3]thiazin-2-amine

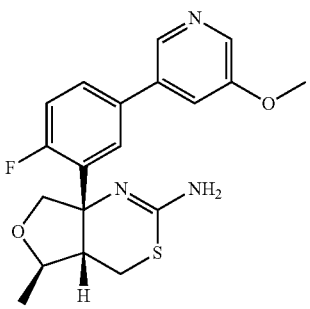 [SMILES: COc1cncc(-c2ccc(F)c([C@]34CO[C@H](C)[C@H]3CSC(N)=N4)c2)c1]

This material was prepared using the procedures described in Example 1, replacing pyrimidin-5-ylboronic acid with the appropriate boronic acid.

$^1$H NMR (400 MHz, CDCl$_3$) δ ppm: 8.41 (d, J=1.8 Hz, 1 H), 8.29 (d, J=2.8 Hz, 1 H), 7.62 (dd, J=7.8, 2.3 Hz, 1 H), 7.43-7.49 (m, 1 H), 7.33 (t, J=2.1 Hz, 1 H), 7.16 (dd, J=11.9, 8.6 Hz, 1 H), 4.64 (d, J=9.3 Hz, 1 H), 4.31-4.42 (m, 1 H), 3.91 (s, 3 H), 3.87-3.90 (m, 1 H), 3.13 (dd, J=13.4, 3.8 Hz, 1 H), 2.77 (dd, J=13.4, 4.0 Hz, 1 H), 2.58-2.69 (m, 1 H), 1.39 (d, J=6.1 Hz, 3 H)

EXAMPLE 9

(4aS,5R,7aS)-7a-(2-Fluoro-5-(5-fluoropyridin-3-yl)phenyl)-5-methyl-4a,5,7,7a-tetrahydro-4H-furo[3,4-d][1,3]thiazin-2-amine

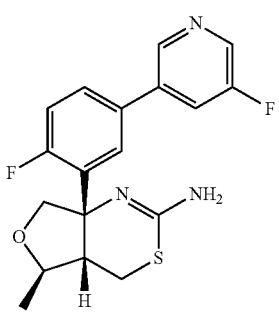 [SMILES: C[C@H]1OC[C@]2(c3cc(-c4cncc(F)c4)ccc3F)N=C(N)SC[C@H]12]

This material was prepared using the procedures described in Example 1, replacing pyrimidin-5-ylboronic acid with the appropriate boronic acid. However there was no purification at the intermediate stage. The final compound was purified by column chromatography (gradient 0-15% MeOH in EtOAc).

$^1$H NMR (400 MHz, CDCl$_3$) δ ppm: 8.64 (s, 1 H), 8.46 (d, J=2.5 Hz, 1 H), 7.64 (dd, J=7.7, 2.4 Hz, 1 H), 7.56 (dt, J=9.6, 2.3 Hz, 1 H), 7.46 (ddd, J=8.3, 4.5, 2.5 Hz, 1 H), 7.18 (dd, J=11.9, 8.3 Hz, 1 H), 4.65 (dd, J=8.8, 1.0 Hz, 1 H), 4.37 (quin, J=6.4 Hz, 1 H), 3.83 (dd, J=8.8, 2.0 Hz, 1 H), 3.10 (dd, J=13.4, 3.8 Hz, 1 H), 2.75 (dd, J=13.4, 4.0 Hz, 1 H), 2.53-2.60 (m, 1 H), 1.38 (d, J=6.1 Hz, 3 H)

EXAMPLE 10

(4aS,5R,7aS)-7a-(2-Fluoro-5-(6-fluoropyridin-3-yl)phenyl)-5-methyl-4a,5,7,7a-tetrahydro-4H-furo[3,4-d][1,3]thiazin-2-amine

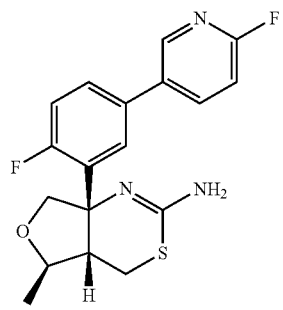 [SMILES: C[C@H]1OC[C@]2(c3cc(-c4ccc(F)nc4)ccc3F)N=C(N)SC[C@H]12]

This material was prepared using the procedures described in Example 1, replacing pyrimidin-5-ylboronic acid with the appropriate boronic acid. However there was no purification at the intermediate stage. The final compound was purified by column chromatography (gradient 0-15% MeOH in EtOAc).

$^1$H NMR (400 MHz, CDCl$_3$) δ ppm: 8.38 (d, J=2.3 Hz, 1 H), 7.93 (td, J=8.1, 2.5 Hz, 1 H), 7.58 (dd, J=7.7, 2.4 Hz, 1 H), 7.40 (ddd, J=8.4, 4.4, 2.4 Hz, 1 H), 7.16 (ddd, J=11.7, 8.5 Hz, 1 H), 6.99 (dd, J=8.6, 2.8 Hz, 1 H), 4.64 (dd, J=8.7, 1.1 Hz, 1 H), 4.32-4.41 (m, 1 H), 3.82 (dd, J=8.7, 2.1 Hz, 1 H), 3.10 (dd, J=13.4, 3.8 Hz, 1 H), 2.74 (dd, J=13.4, 4.0 Hz, 1 H), 2.53-2.59 (m, 1 H), 1.38 (d, J=6.1 Hz, 3 H)

EXAMPLE 11

(4aS,5R,7aS)-7a-(2-Fluoro-5-(6-methoxypyridin-3-yl)phenyl)-5-methyl-4a,5,7,7a-tetrahydro-4H-furo[3,4-d][1,3]thiazin-2-amine

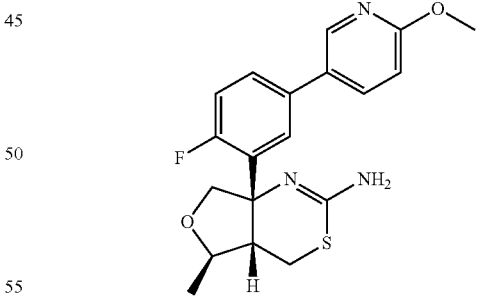

This material was prepared using the procedures described in Example 1, replacing pyrimidin-5-ylboronic acid with the appropriate boronic acid. However there was no purification at the intermediate stage. The final compound was purified using purification Method B.

$^1$H NMR (400 MHz, CDCl$_3$) δ ppm: 8.36 (d, J=2.3 Hz, 1 H), 7.77 (dd, J=8.6, 2.5 Hz, 1 H), 7.56 (dd, J=7.8, 2.3 Hz, 1 H), 7.39-7.48 (m, 1 H), 7.16 (dd, J=12.0, 8.5 Hz, 1 H), 6.83 (d, J=8.6 Hz, 1 H), 4.63 (d, J=9.3 Hz, 1 H), 4.34-4.43 (m, 1 H), 4.04 (dd, J=9.1, 2.0 Hz, 1 H), 3.99 (s, 3 H), 3.15-3.23 (m, 1 H), 2.73-2.87 (m, 2 H), 1.41 (d, J=6.1 Hz, 3 H)

EXAMPLE 12

(4aS,5R,7aS)-5-Methyl-7a-(2',4,5'-trifluoro-[1,1'-biphenyl]-3-yl)-4a,5,7,7a-tetrahydro-4H-furo[3,4-d][1,3]thiazin-2-amine

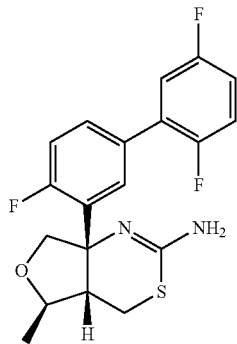 [SMILES: C[C@H]1OC[C@]2(c3cc(-c4cc(F)ccc4F)ccc3F)N=C(N)SC[C@H]12]

Step 1: tert-Butyl [(4aS,5R,7aS)-7a-(5-Bromo-2-fluorophenyl)-5-methyl-4a,5,7,7a-tetrahydro-4H-furo[3,4-d][1,3]thiazin-2-yl]carbamate

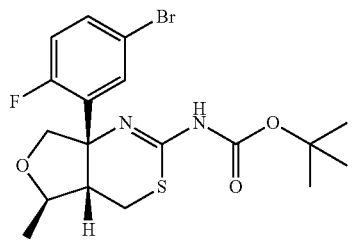 [SMILES: C[C@H]1OC[C@]2(c3cc(Br)ccc3F)N=C(NC(=O)OC(C)(C)C)SC[C@H]12]

(4aS,5R,7aS)-7a-(5-Bromo-2-fluorophenyl)-5-methyl-4a,5,7,7a-tetrahydro-4H-furo[3,4-d][1,3]thiazin-2-amine (3 g, 8.69 mmol) was dissolved THF (20 mL) and to the solution was added di-tert-butyl dicarbonate (2.28 g, 10.4 mmol). The reaction was stirred at 80° C. overnight. The solvents were removed in vacuo and the residue was purified using column chromatography (gradient 0-60% EtOAc in hexane) to give the title compound (3 g, colourless solid). $^1$H NMR (400 MHz. CDCl$_3$) δ ppm: 7.32-7.60 (m, 2H), 6.85-7.02 (m, 1H), 4.48-4.60 (m, 1H), 4.29-4.47 (m, 1H), 3.73-3.85 (m, 1H), 2.95-3.12 (m, 1H), 2.58-2.75 (m, 2H), 1.47-1.59 (m, 9H), 1.32-1.43 (m, 3H)

Step 2: (4aS,5R,7aS)-5-Methyl-7a-(2',4,5'-trifluoro-[1,1'-biphenyl]-3-yl)-4a,5,7,7a-tetrahydro-4H-furo[3,4-d][1,3]thiazin-2-amine

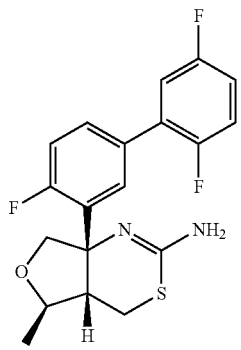 [SMILES: C[C@H]1OC[C@]2(c3cc(-c4cc(F)ccc4F)ccc3F)N=C(N)SC[C@H]12]

tert-Butyl[(4aS,5R,7aS)-7a-(5-bromo-2-fluorophenyl)-5-methyl-4a,5,7,7a-tetrahydro-4H-furo[3,4-d][1,3]thiazin-2-yl]imidodicarbonate (0.15 g, 0.34 mmol) was dissolved in 1,2-dimethoxyethane (1.5 mL), water (0.7 mL) and ethanol (0.5 mL). The resulting solution was heated to 100° C. and to it was added (2,5-difluorophenyl)boronic acid (0.11 g, 0.67 mmol), cesium carbonate (0.659 g, 2.02 mmol) and dichloropalladium-triphenylphosphane (0.047 g, 0.067 mmol) and the reaction was stirred at 100° C. After 1 hour, the reaction mixture was cooled to room temperature, diluted with saturated aqueous NaHCO$_3$ and extracted with EtOAc (×3). The combined organic layers were dried (MgSO$_4$), filtered and concentrated in vacuo. The residue was dissolved in DCM (2 mL) and trifluoroacetic acid (2 mL). After 1 hour, the solvents were removed in vacuo. The residue was neutralised with saturated aqueous NaHCO$_3$ and extracted with DCM (×2). The combined organic layers were dried (MgSO$_4$), filtered and concentrated. The residue was purified using column chromatography (gradient 0-15% MeOH in EtOAc) to give the title compound (18 mg, colourless solid). $^1$H NMR (400 MHz, CDCl$_3$) δ ppm: 7.50-7.58 (m, 2 H), 7.09-7.2 (m, 3 H), 6.97-7.06 (m, 1 H), 4.61 (d, J=10.1 Hz, 1 H), 4.35-4.47 (m, 1 H), 4.21 (dd, J=10.0, 1.6 Hz, 1 H), 3.28 (dd, J=13.5, 3.7 Hz, 1 H), 3.03 (dt, J=8.1, 4.0 Hz, 1 H), 2.91 (dd, J=13.6, 4.0 Hz, 1 H), 1.44 (d, J=6.1 Hz, 3 H)

EXAMPLE 13

5-(3-((4aS,5R,7aS)-2-Amino-5-methyl-4a,5,7,7a-tetrahydro-4H-furo[3,4-d][1,3]thiazin-7a-yl)-4-fluorophenyl)nicotinonitrile

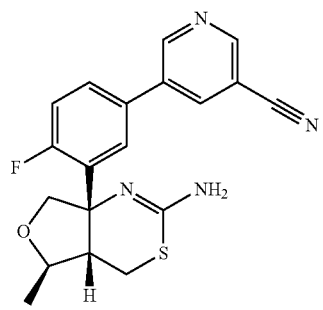 [SMILES: C[C@H]1OC[C@]2(c3cc(-c4cncc(C#N)c4)ccc3F)N=C(N)SC[C@H]12]

This material was prepared using the procedures described in Example 12, replacing (2,5-difluorophenyl)boronic acid with the appropriate boronic acid.

$^1$H NMR (400 MHz, CDCl$_3$) δ ppm: 9.02 (d, J=2.0 Hz, 1 H), 8.88 (d, J=1.8 Hz, 1 H), 8.33 (s, 1 H), 8.14 (t, J=2.0 Hz, 1 H), 7.67 (dd, J=7.6, 2.3 Hz, 1 H), 7.49-7.57 (m, 1 H), 4.62 (d, J=10.1 Hz, 1 H), 4.42 (t, J=6.7 Hz, 1 H), 4.04-4.12 (m, 1 H), 3.22 (d, J=9.9 Hz, 1 H), 2.82-2.92 (m, 2 H), 1.43 (d, J=6.1 Hz, 3 H)

EXAMPLE 14

(4aS,5R,7aS)-7a-(2-Fluoro-5-(5-(trifluoromethyl)pyridine-3-yl)phenyl)-5-methyl-4a,5,7,7a-tetrahydro-4H-furo[3,4-d][1,3]thiazin-2-amine

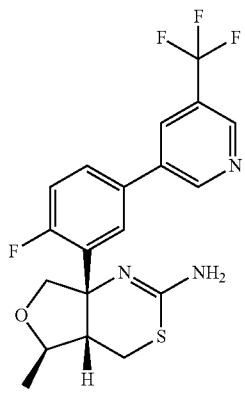 [SMILES: C[C@H]1OC[C@]2(c3cc(-c4cncc(C(F)(F)F)c4)ccc3F)N=C(N)SC[C@H]12]

tert-Butyl[(4aS,5R,7aS)-7a-(5-bromo-2-fluorophenyl)-5-methyl-4a,5,7,7a-tetrahydro-4H-furo[3,4-d][1,3]thiazin-2-yl]imidodicarbamate (0.15 g, 0.34 mmol) was dissolved in 1,2-dimethoxyethane (1.5 mL), water (0.7 mL) and ethanol (0.5 mL). The resulting solution was heated to 100° C. and to it was added [5-(trifluoromethyl)pyridin-3-yl]boronic acid (0.32 g, 1.68 mmol), cesium carbonate (0.659 g, 2.02 mmol) and dichloropalladium-triphenylphosphane (0.047 g, 0.067 mmol) and the reaction was stirred at 100° C. After 1 hour, the reaction mixture was cooled to room temperature, diluted with saturated aqueous NaHCO$_3$ and extracted with EtOAc (×3). The combined organic layers were dried (MgSO$_4$), filtered and concentrated in vacuo. The residue was purified using column chromatography (gradient 0-60% EtOAc in hexane). The purified product was dissolved in DCM (2 mL) and trifluoroacetic acid (2 L). After 1 hour, the solvents were removed in vacuo. The residue was neutralised with saturated aqueous NaHCO$_3$ and extracted with DCM (×2). The combined organic layers were dried (MgSO$_4$), filtered and concentrated to give the title compound (35 mg, colourless solid).

$^1$H NMR (400 MHz, CDCl$_3$) δ ppm: 9.00 (d, J=1.8 Hz, 1 H), 8.87 (s, 1 H), 8.06 (s, 1 H), 7.67 (dd, J=7.6, 2.3 Hz, 1 H), 7.48 (ddd, J=8.3, 4.4, 2.4 Hz, 1 H), 7.21 (dd, J=11.7, 8.5 Hz, 1 H), 4.65 (dd, J=8.8, 1.0 Hz, 1 H), 4.33-4.42 (m, 1 H), 3.84 (dd, J=9.0, 2.1 Hz, 1 H), 3.10 (dd, J=13.1, 3.8 Hz, 1 H), 2.76 (dd, J=13.4, 4.0 Hz, 1 H), 2.54-2.61 (m, 1 H), 1.39 (d, J=6.1 Hz, 3 H)

EXAMPLE 15

(4aS,5R,7aS)-7a-(2-Fluoro-5-(5-methylpyridin-3-yl)phenyl)-5-methyl-4a,5,7,7a-tetrahydro-4H-furo[3,4-d][1,3]thiazin-2-amine

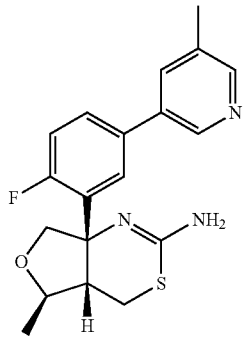 [SMILES: Cc1cncc(-c2ccc(F)c([C@]34CO[C@H](C)[C@H]3CSC(N)=N4)c2)c1]

This material was prepared using the procedures described in Example 14, replacing [5-(trifluoromethyl)pyridin-3-yl]boronic acid with the appropriate boronic acid.

$^1$H NMR (400 MHz, CDCl$_3$) δ ppm: 8.62 (d, J=1.8 Hz, 1 H), 8.42 (d, J=1.5 Hz, 1 H), 7.63-7.65 (m, 1 H), 7.61 (dd, J=7.8, 2.5 Hz, 1 H), 7.44 (ddd, J=8.3, 4.5, 2.4 Hz, 1 H), 7.15 (dd, J=11.9, 8.6 Hz, 1 H), 4.66 (dd, J=8.8, 1.0 Hz, 1 H), 4.37 (quin, J=6.6 Hz, 1 H), 3.84 (dd, J8.8, 2.3 Hz, 1 H), 3.12 (dd, J=13.3, 3.9 Hz, 1 H), 2.75 (dd, J=13.3, 3.9 Hz, 1 H), 2.50-2.63 (m, 1 H), 2.40 (s, 3 H), 1.38 (d, J=6.1 Hz, 3 H)

EXAMPLE 16

(4aS,5R,7aS)-7a-(2-fluoro-5-(2-fluoro-5-methylpyridin-3-yl)phenyl)-5-methyl-4a,5,7,7a-tetrahydro-4H-furo[3,4-d][1,3]thiazin-2-amine

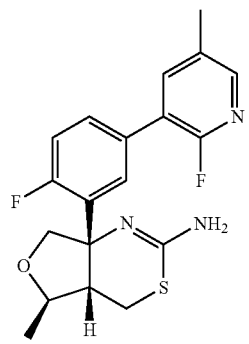 [SMILES: Cc1cnc(F)c(-c2ccc(F)c([C@]34CO[C@H](C)[C@H]3CSC(N)=N4)c2)c1]

This material was prepared using the procedures described in Example 14, replacing [5-(trifluoromethyl)pyridin-3-yl]boronic acid with the appropriate boronic acid.

$^1$H NMR (400 MHz, CDCl$_3$) δ ppm: 7.99 (s, 1 H), 7.65 (dd, J=7.3 Hz, 1 H), 7.58 (d, J=8.1 Hz, 1 H), 7.42-7.49 (m, 1 H), 7.15 (dd, J=11.9, 8.3 Hz, 1 H), 4.65 (d, J=8.8 Hz, 1 H), 4.32-4.41 (m, 1 H), 3.84 (dd, J=8.8, 1.8 Hz, 1 H), 3.13 (dd, J=13.3, 3.7 Hz, 1 H), 2.75 (dd, J=13.1, 4.0 Hz, 1 H), 2.52-2.60 (m, 1 H), 2.38 (s, 3 H), 1.38 (d, J=6.1 Hz, 3 H)

EXAMPLE 17

(4aS,5R,7aS)-7a-(2-Fluoro-5-(1H-pyrazol-5-yl)phenyl)-5-methyl-4a,5,7,7a-tetrahydro-4H-furo[3,4-d][1,3]-thiazin-2-amine

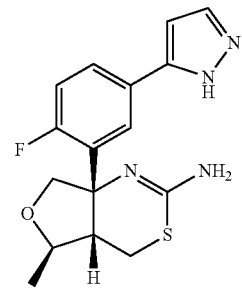 [SMILES: C[C@H]1OC[C@]2(c3cc(-c4ccn[nH]4)ccc3F)N=C(N)SC[C@H]12]

This material was prepared using the procedures described in Example 1, replacing pyrimidin-5-ylboronic acid with the appropriate boronic acid.

¹H NMR (400 MHz, CDCl₃) δ ppm: 7.87 (dd, J=7.8, 2.3 Hz, 1 H), 7.55-7.64 (m, 2 H), 7.09 (dd, J=12.0, 8.5 Hz, 1 H), 6.55 (d, J=2.3 Hz, 1 H), 4.64 (dd, J=8.8, 1.0 Hz, 1 H), 4.32-4.44 (m, 1 H), 3.86 (dd, J=8.7, 2.4 Hz, 1 H), 3.10 (dd, J=13.4, 3.8 Hz, 1 H), 2.72 (dd, J=13.1, 3.8 Hz, 1 H), 2.54-2.63 (m, 1 H), 1.38 (d, 0.1-6.1 Hz, 3 H).

EXAMPLE 18

(4aS,5R,7aS)-7a-(2-fluoro-5-(2-methylpyridin-3-yl)phenyl)-5-methyl-4a,5,7,7a-tetrahydro-4H-furo[3,4-d][1,3]thiazin-2-amine

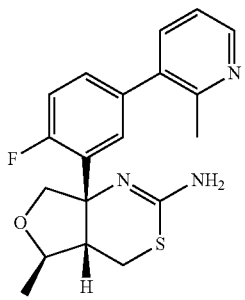 [SMILES: Cc1ncccc1-c1ccc(F)c([C@]23CO[C@H](C)[C@H]2CSC(N)=N3)c1]

This material was prepared using the procedures described in Example 12, replacing (2,5-difluorophenyl)boronic acid with 5 equivalents of the appropriate boronic acid.

¹H NMR (400 MHz, CDCl₃) δ ppm: 8.51 (dd, J=1.52, 4.80 Hz, 1H), 7.50 (dd, J=1.64, 7.71 Hz, 1H), 7.37 (dd, =2.15, 7.96 Hz, 1H), 7.09-7.24 (m, 3H), 4.66 (dd, J=0.76, 8.84 Hz, 1H), 4.29-4.40 (m, 1H), 3.84 (dd, J=2.15, 8.72 Hz, 114), 3.11 (dd, J=3.92, 13.26 Hz, 1H), 2.77 (dd, J=4.17, 13.26 Hz, 1H), 2.52-2.60 (m, 1H), 2.50 (s, 3H), 1.37 (d, J=6.06 Hz, 3H).

EXAMPLE 19

(4aS,5R,7aS)-7a-(2-fluoro-5-(5-(prop-1-yn-1-yl)pyridin-3-yl)phenyl)-5-methyl-4a 5,7,7a-tetrahydro-4H-furo[3,4-d][1,3]thiazin-2-amine

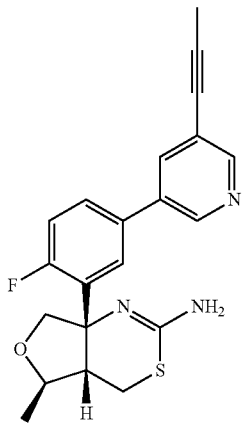

This material was prepared using the procedures described in Example 14, replacing replacing [5-(trifluoromethyl)pyridin-3-yl]boronic acid with the appropriate boronic acid.

¹H NMR (400 MHz, CDCl₃) δ ppm: 8.67 (d, J=2.02 Hz, 1H), 8.60 (d, J=2.02 Hz, 1H), 7.84 (t, J=2.02 Hz, 1H), 7.61 (dd, =2.40, 7.71 Hz, 1H), 7.47 (ddd, J=2.40, 4.42, 8.34 Hz, 1H), 7.18 (dd, J=8.34, 11.87 Hz, 1H), 4.64 (dd, J=0.88, 9.22 Hz, 1H), 4.35-4.44 (m, 1H), 3.93 (d, J=7.83 Hz, 1H), 3.16 (dd, J=3.54, 13.39 Hz, 1H), 2.80 (dd, J=3.92, 13.26 Hz, 1H), 2.70 (br. s., 1H), 2.11 (s, 3H), 1.40 (d, J=6.06 Hz, 3H).

EXAMPLE 20

(4aS,5R,7aS)-7a-(2-fluoro-5-(1-methyl-1H-pyrazol-5-yl)phenyl)-5-methyl-4a,5,7,7a-tetrahydro-4H-furo[3,4-d]thiazin-2-amine

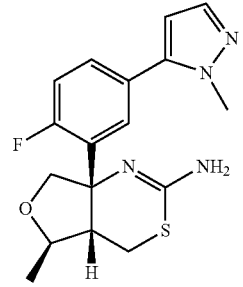 [SMILES: C[C@H]1OC[C@]2(c3cc(-c4ccnn4C)ccc3F)N=C(N)SC[C@H]12]

This material was prepared using the procedures described in Example 1, replacing pyrimidin-5-ylboronic acid with 5 equivalents of the appropriate boronic acid.

¹H NMR (400 MHz, CDCl₃) δ ppm: 7.52 (d, J=1.96 Hz, 1H), 7.48 (dd, J=2.26, 7.76 Hz, 1H), 7.32 (ddd, J=2.32, 4.52, 8.31 Hz, 1H), 7.15 (dd, J=8.44, 11.86 Hz, 1H), 6.31 (d, J=1.96 Hz, 1H), 4.65 (dd, J=1.22, 8.93 Hz, 1H), 4.31-4.40 (m, 1H), 3.88 (s, 3H), 3.85 (dd, J=2.08, 8.93 Hz, 1H), 3.10 (dd, J=3.91, 13.33 Hz, 1H), 2.77 (dd, J=4.03, 13.33 Hz, 1H), 2.53-2.59 (m, 1H), 1.38 (d, J=6.11 Hz, 3H).

EXAMPLE 21

(4aS,5R,7aS)-7a-(5-(5-cyclopropoxypyridin-3-yl)-2-fluorophenyl)-5-methyl-4a,5,7,7a-tetrahydro-4H-furo[3,4-d][1,3]thiazin-2-amine

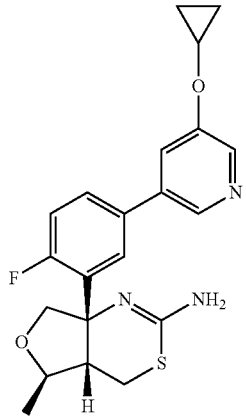 [SMILES: C[C@H]1OC[C@]2(c3cc(-c4cncc(OC5CC5)c4)ccc3F)N=C(N)SC[C@H]12]

di-tert-Butyl {(4aS,5R,7aS)-7a-[2-fluoro-5-(4,4,5,5-tetramethyl-1,3,2-dioxaborolan-2-yl)phenyl]-5-methyl-4a,5,7,7a-tetrahydro-4H-furo[3,4-d][1,3]thiazin-2-yl}imidodicarbonate (0.13 g, 0.22 mmol) was dissolved in 1,2-dimethoxyethane (1.5 mL), water (0.7 mL) and ethanol (0.5 mL) The resulting solution was heated to 100° C. and to it was added 3-bromo-5-(cyclopropyloxy)pyridine (0.28 g, 1.32 mmol), cesium carbonate (0.43 g, 1.32 mmol) and bis(triphenylphosphine)palladium (II) dichloride (0.046 g, 0.066 mmol) and the reaction was stirred at 100° C. After 1 hour, the reaction mixture was cooled to room temperature, diluted with saturated aqueous NaHCO₃ and extracted with EtOAc (×3). The combined organic layers were dried (MgSO₄), filtered and concentrated in vacuo. The residue was purified using column chromatography gradient 0-60% EtOAc in hexane). The purified product was dissolved in DCM (2 mL) and trifluoroacetic acid (1 mL). After 1 hour, the solvents were removed in vacuo. The residue was basified with saturated aqueous NaHCO₃ and extracted with DCM (×3). The combined organic layers were dried (MgSO₄), filtered and concentrated to leave the title compound. (58 mg)

¹H NMR (400 MHz, CDCl₃) δ ppm: 8.44 (dd, =2.15, 933 Hz, 2H), 7.63 (dd, J=2.40, 7.71 Hz, 1H), 7.44-7.50 (m, 2H), 7.17 (dd, J=8.34, 11.87 Hz, 1H), 4.66 (dd, J=1.01, 8.84 Hz, 1H), 4.32-4.44 (m, 1H), 3.80-3.92 (m, 2H), 3.12 (dd, J=3.79, 13.14 Hz, 1H), 2.76 (dd, J=4.04, 13.39 Hz, 1H), 2.52-2.62 (m, 1H), 1.39 (d, J=6.06 Hz, 3H), 1.26-1.30 (m, 4H).

EXAMPLE 22

(4aS,5R,7aS)-7a-(2-fluoro-5-(pyrazin-2-yl)phenyl)-5-methyl-4a,5,7,7a-tetrahydro-4H-furo[3,4-d][1,3]thiazin-2-amine

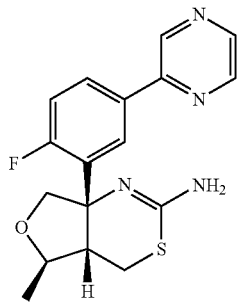 [SMILES: C[C@H]1OC[C@]2(c3cc(-c4cnccn4)ccc3F)N=C(N)SC[C@H]12]

This material was prepared using the procedures described in Example 21, replacing 3-bromo-5-(cyclopropyloxy)pyridine with the appropriate bromide.

¹H NMR (400 MHz, CDCl₃) δ ppm: 9.00 (d, J=1.52 Hz, 1H), 8.61 (dd, J=1.52, 2.27 Hz, 1H), 8.49 (d, J=2.53 Hz, 1H), 8.06 (dd, J=2.27, 7.83 Hz, 1H), 7.94 (ddd, J=2.40, 4.61, 8.40 Hz, 1H), 7.19 (dd, J=8.46, 11.75 Hz, 1H), 4.64 (dd, J=1.01, 8.84 Hz, 1H), 4.37 (quin, J=6.63 Hz, 1H), 3.84 (dd, J=2.27, 8.84 Hz, 1H), 3.11 (dd, J=3.79, 13.14 Hz, 1H), 2.74 (dd, J=3.92, 13.26 Hz, 1H), 2.54-2.59 (m, 1H), 1.37 (d, J=6.32 Hz, 3H)

EXAMPLE 23

(4aS,5R,7aS)-7a-(2-fluoro-5-(pyridazin-3-yl)phenyl)-5-methyl-4a,5,7,7a-tetrahydro-4H-furo[3,4-d][1,3]thiazin-2-amine

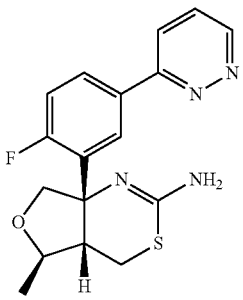 [SMILES: C[C@H]1OC[C@]2(c3cc(-c4cccnn4)ccc3F)N=C(N)SC[C@H]12]

This material was prepared using the procedures described in Example 21, replacing 3-bromo-5-(cyclopropyloxy)pyridine with the appropriate bromide.

¹H NMR (400 MHz, CDCl₃) δ ppm: 9.17 (t, J=1.00 Hz, 1H), 8.05-8.14 (m, 2H), 7.84-7.89 (m, 1H), 7.55 (t, J=1.00 Hz, 1H), 7.21-7.26 (m, 1H), 4.61-4.67 (m, 1H), 4.36-4.45 (m, 1H), 3.87-3.97 (m, 1H), 3.07-3.23 (m, 1H), 2.74-2.83 (m, 1H), 2.62-2.73 (m, 1H), 1.41 (d, J=6.06 Hz, 3H).

EXAMPLE 24

(4aS,5R,7aS)-7a-(2-fluoro-5-(6-methoxypyridin-2-yl)phenyl)-5-methyl-4a,5,7,7a-tetrahydro-4H-furo[3,4-d][1,3]thiazin-2-amine

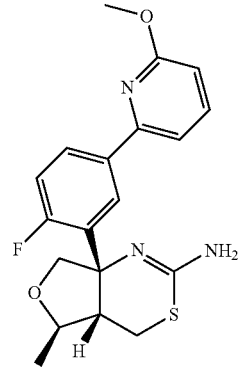 [SMILES: COc1cccc(-c2ccc(F)c([C@]34CO[C@H](C)[C@H]3CSC(N)=N4)c2)n1]

This material was prepared using the procedures described in Example 21, replacing 3-bromo-5-(cyclopropyloxy)pyridine with the appropriate bromide.

¹H NMR (400 MHz, CDCl₃) δ ppm: 8.12 (dd, J=2.32, 8.07 Hz, 1H), 7.90-8.02 (m, 1H), 7.63 (t, J=7.76 Hz, 1H), 7.32 (d, J=7.34 Hz, 1H), 7.14 (dd, J=8.44, 11.86 Hz, 1H), 6.69 (d, J=8.19 Hz, 1H), 4.68 (d, J=8.80 Hz, 1H), 4.29-4.43 (m, 1H), 4.04 (s, 3H), 3.90 (dd, J=2.08, 8.93 Hz, 1H), 3.16 (dd, J=3.91, 13.20 Hz, 1H), 2.77 (dd, 3.85, 13.27 Hz, 1H), 2.52-2.64 (m, 1H), 1.39 (d, J=6.11 Hz, 3H).

EXAMPLE 25

6-(3-((4aS,5R,7aS)-2-amino-5-methyl-4a,5,7,7a-tetrahydro-4H-furo[3,4-d][1,3]thiazin-7a-yl)-4-fluorophenyl)pyridin-2(1H)-one

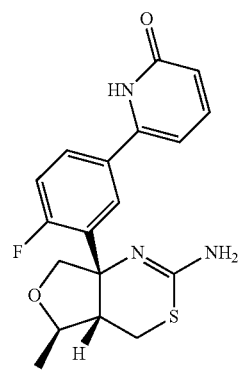 [SMILES: C[C@H]1OC[C@]2(c3cc(-c4cccc(=O)[nH]4)ccc3F)N=C(N)SC[C@H]12]

This material was prepared using the procedures described in Example 21, replacing 3-bromo-5-(cyclopropyloxy)pyridine with the appropriate bromide.

¹H NMR (400 MHz, CDCl₃) δ ppm: 1.39 (d, J=6.11 Hz, 3 H) 2.58-2.66 (m, 1 H) 2.75 (dd, J=13.33, 3.91 Hz, 1 H) 3.17 (dd, J=13.27, 3.85 Hz, 1 H) 3.87 (dd, J=8.86, 1.90 Hz, 1 H) 4.33-4.43 (m, 1 H) 4.60 (dd, J=8.93, 0.98 Hz, 1 H) 6.47 (d, J=6.97 Hz, 1 H) 6.53 (d, J=9.17 Hz, 1 H) 7.17 (dd, J=11.68, 8.50 Hz, 1 H) 7.47 (dd, J=9.05, 7.09 Hz, 1 H) 7.57 (ddd, J=8.47, 4.31, 2.51 Hz, 1 H) 7.78 (dd, J=7.58, 2.20 Hz, 1 H).

EXAMPLE 26

(4aS,5R,7aS)-7a-(5-(5-difluoromethoxy)pyridin-3-yl)-2-fluorophenyl)-5-methyl-4a,5,7,7a-tetrahydro-4H-furo[3,4-d][1,3]thiazin-2-amine

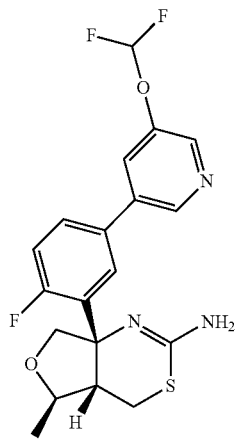 [SMILES: C[C@H]1OC[C@]2(c3cc(-c4cncc(OC(F)F)c4)ccc3F)N=C(N)SC[C@H]12]

This material was prepared using the procedures described in Example 21, replacing 3-bromo-5-(cyclopropyloxy)pyridine with 2 equivalents of 3-bromo-5-(difluoromethoxy)pyridine (U.S. Pat. No. 6,642,237 B1).

$^1$H NMR (400 MHz, CDCl$_3$) δ ppm: 8.70 (d, J=1.71 Hz, 1H), 8.48 (d, J=2.20 Hz, 1H), 7.62-7.67 (m, 2H), 7.44-7.51 (m, 1H), 7.19 (dd, J=8.44, 11.74 Hz, 1H), 6.62 (td, J=1.00, 72.50 Hz, 1H), 4.65 (d, J=8.93 Hz, 1H), 4.38 (quin, J=6.57 Hz, 1H), 3.86 (dd, J=1.90, 8.86 Hz, 1H), 3.11 (dd, J=3.73, 13.27 Hz, 1H), 2.77 (dd, J=3.91, 13.33 Hz, 1H), 2.60 (td, J=3.90, 8.22 Hz, 1H), 1.40 (d, J=6.11 Hz, 3H).

EXAMPLE 27

(4aS,5S,7aS)-7a-(2,4-Difluoro-5-(pyrimidin-5-yl)phenyl)-5-(fluoromethyl)-4a,5,7,7a-tetrahydro-4H-furo[3,4-d][1,3]thiazin-2-amine

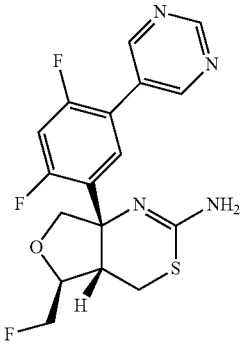 [SMILES: NC1=N[C@@]2(c3cc(-c4cncnc4)c(F)cc3F)CO[C@H](CF)[C@H]2CS1]

Step 1: (3aR,4S,6aS)-6a-(3-Chloro-2,4-difluorophenyl)-4-((trityloxy)methyl) hexahydrofuro[3,4-c]isoxazole

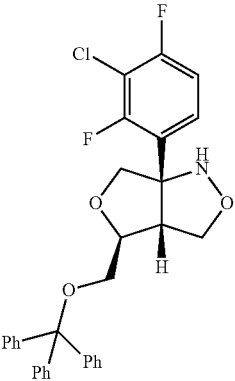 [SMILES: Fc1ccc([C@]23CO[C@H](COC(c4ccccc4)(c4ccccc4)c4ccccc4)[C@H]2CON3)c(F)c1Cl]

A stirred solution of 2,2,6,6-tetramethylpiperidine (1.31 mL, 7.78 mmol) in dry THF (20 mL) under nitrogen was cooled in an acetone/dry ice cooling bath. n-Butyl lithium (2.5 M in hexanes, 3.11 mL, 7.78 mmol) was added to this solution such that the internal temperature remained below −75° C. The pale yellow solution was stirred at this temperature for 15 minutes before the addition of a solution of 2-chloro-1,3-difluoro-benzene (0.86 mL, 7.78 mmol) in dry THF (2 mL). The solution was stirred for an additional 30 minutes at −78° C. before the addition of a solution of (3aR, 4S)-4-((trityloxy)methyl)-3,3a,4,6-tetrahydrofuro[3,4-c]isoxazole (1.5 g, 3.89 mmol) in dry THF (12 mL). The reaction was stirred at −78° C. After 60 min, the reaction was quenched with saturated aqueous ammonium chloride and then removed from the cooling bath. The mixture was partitioned between EtOAc and water and the layers were separated. The aqueous layer was extracted with EtOAc (3×). The combined organic extracts were washed with brine (1×), then dried over (Na$_2$SO$_4$), filtered and evaporated. The residue was purified by column chromatography (normal phase, 50 g, Biotage SNAP cartridge KP-Sil, 50 mL per min, gradient 5% to 20% to 30% EtOAc in n-hexane) to give the title compound (712 mg). $^1$H NMR (400 MHz, CDCl$_3$) δ ppm: 3.23-3.35 (m, 2 H) 3.47 (dd, J=9.84, 6.42 Hz, 1 H) 3.86 (dd, J=8.31, 3.79 Hz, 1 H) 3.91 (dd, J=10.33, 1.90 Hz, 1 H) 4.08-4.20 (m, 2 H) 4.22-4.33 (m, 1 H) 6.92-7.00 (m, 1 H) 7.20-7.36 (m, 9 H) 7.41-7.48 (m, 6 H) 7.57-7.67 (m, 1 H).

Step 2: ((2S,3R,4S)-4-Amino-4-(3-chloro-2,4-difluorophenyl)-2-((trityloxy)methyl) tetrahydrofuran-3-yl)methanol

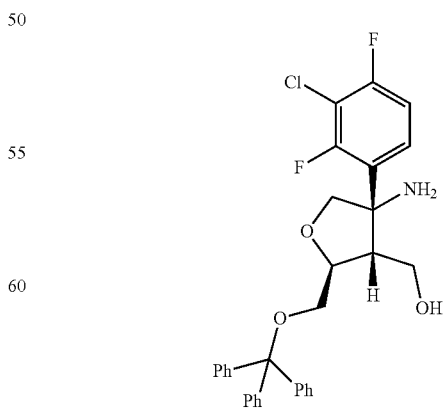

Zinc (2.75 g, 42.1 mmol) was added in one portion to a stirred suspension of (3aR,4S,6aS)-6a-(3-chloro-2,4-difluorophenyl)-4-((trityloxy)methyl)hexahydrofuro[3,4-c]isoxazole (4.5 g, 8.43 mmol) in acetic acid (15 mL) at RT. An exotherm was noted. The mixture was stirred at RT overnight. The zinc was removed by filtration through Celite® washing with methanol. The filtrate was evaporated and the residue was partitioned between DCM and saturated aqueous NaHCO$_3$. The mixture was filtered through Celite® again—washing with DCM and water. The layers were separated and the aqueous layer was further extracted with DCM (×3). The combined extracts were dried by passing through a hydrophobic frit and evaporated to give the title compound (4.38 g). $^1$H NMR (400 MHz, CDCl$_3$) δ ppm: 2.61-2.71 (m, 1 H) 3.23-3.32 (m, 2 H) 3.68 (dd, J=12.04, 5.32 Hz, 1 H) 3.91 (dd, J=12.10, 4.28 Hz, 1 H) 3.96 (dd, J=9.23, 2.63 Hz, 1 H) 4.28-4.37 (m, 2 H) 6.94-7.01 (m, 1 H) 7.20-7.34 (m, 9 H) 7.38-7.53 (m, 7 H.

Step 3: ((2S,3R,4S)-4-Amino-4-(2,4-difluorophenyl)-2-((trityloxy)methyl) tetrahydrofuran-3-yl)methanol

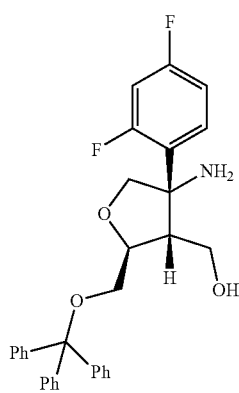 [SMILES: N[C@@]1(c2ccc(F)cc2F)CO[C@H](COC(c2ccccc2)(c2ccccc2)c2ccccc2)[C@H]1CO]

A mixture of ((2S,3R,4S)-4-amino-4-(3-chloro-2,4-difluorophenyl)-2-((trityloxy)methyl)tetrahydrofuran-3-yl)methanol (4.49 g, 8.4 mmol), ammonium formate (3.2 g, 50 mmol) and 10% palladium on carbon (500 mg) in dry MeOH (40 mL) was stirred at RT under nitrogen overnight. The catalyst was removed by filtration through Celite®—washing with methanol. The filtrate was evaporated and the residue was partitioned between DCM (100 mL) and saturated aqueous NaHCO$_3$ (50 mL). The layers were separated and the aqueous layer was further extracted with DCM (100 mL×4). The combined extracts were dried (Na$_2$SO$_4$), filtered and evaporated to give the title compound (4.18 g). $^1$H NMR (400 MHz, MeOH-d$_4$) δ ppm: 2.73-2.84 (m, 1 H) 3.17 (dd, J=10.03, 5.14 Hz, 1 H) 3.27 (dd, J=9.96, 3.61 Hz, 1 H) 3.65-3.79 (m, 2 H) 3.88 (dd, J=8.93, 3.06 Hz, 1 H) 4.16-4.24 (m, 1 H) 4.27 (d, J=9.05 Hz, 1 H) 6.88-7.00 (m, 2 H) 7.18-7.31 (m, 9 H) 7.38-7.45 (m, 6 H) 7.58-7.67 (m, 1 H).

Step 4: N-(((3S,4R,5S)-3-(2,4-Difluorophenyl)-4-(hydroxymethyl)-5-((trityloxy)methyl)tetrahydrofuran-3-yl)carbamothioyl)benzamide

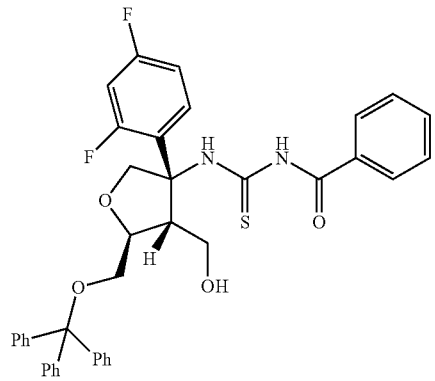 [SMILES: O=C(NC(=S)N[C@@]1(c2ccc(F)cc2F)CO[C@H](COC(c2ccccc2)(c2ccccc2)c2ccccc2)[C@H]1CO)c1ccccc1]

Benzoyl isothiocyanate (1.24 mL, 9.2 mmol) was added to a stirred solution of ((2S,3R,4S)-4-amino-4-(2,4-difluorophenyl)-2-((trityloxy)methyl)tetrahydrofuran-3-yl)methanol (4.2 g, 8.4 mmol) in dry DCM (20 mL) at RT under nitrogen. After 1 hour the volatiles were removed in vacuo and then the residue was purified by column chromatography (normal phase, 100 g, Biotage SNAP cartridge KP-Sil, 50 mL per min, gradient 5% to 30% EtOAc in n-hexane) to give the title compound (5.4 g). $^1$H NMR (400 MHz, MeOH-d$_4$) δ ppm: 2.71-2.83 (m, 1 H) 3.12 (dd, J=10.15, 4.52 Hz, 1 H) 3.27 (dd, J=10.15, 3.67 Hz, 1 H) 3.83 (d, J=5.26 Hz, 2 H) 4.19-4.27 (m, 1 H) 4.55 (d, J=9.78 Hz, 1 H) 5.18 (d, J=9.78 Hz, 1 H) 6.82-6.96 (m, 2 H) 7.17-7.32 (m, 9 H) 7.36-7.41 (m, 6 H) 7.49-7.57 (m, 3 H) 7.60-7.67 (m, 1 H) 7.89-7.94 (m, 2 H), Step 5: N-((4aS,5S,7aS)-7a-(2,4-Difluorophenyl)-5-((trityloxy)methyl)-4a,5,7,7a-tetrahydro-4H-furo[3,4-d][1,3]thiazin-2-yl)benzamide

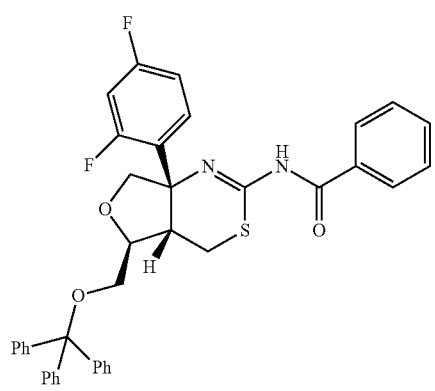 [SMILES: O=C(NC1=N[C@@]2(c3ccc(F)cc3F)CO[C@H](COC(c3ccccc3)(c3ccccc3)c3ccccc3)[C@H]2CS1)c1ccccc1]

Trifluoromethanesulphonic acid anhydride (0.40 mL, 2.35 mmol) was added slowly to a stirred solution of N-(((3S,4R,5S)-3-(2,4-difluorophenyl)-4-(hydroxymethyl)-5-((trityloxy)methyl)tetrahydrofuran-3-yl)carbamothioyl)benzamide (1.3 g, 1.96 mmol) in dry pyridine (4 mL) under nitrogen such that the internal temperature remained below −20° C. Upon complete addition, the reaction was stirred at −20° C. for a further 10 minutes and then transferred to an ice bath. After 2 hours at 0° C. the reaction was quenched with saturated aqueous NH$_4$Cl (20 mL) and then the mixture was partitioned between EtOAc (50 mL) and water (25 mL). The layers were separated and the aqueous layer was further extracted with EtOAc (50 mL×1). The combined extracts were washed with half saturated brine (2×50 mL) and brine (50 mL×1), then dried (Na$_2$SO$_4$), filtered and evaporated. The residue was azeotroped with toluene (×2) to give 1.6 g (oil). The reaction was repeated starting with 5.0 g of N-(((3S,4R,5S)-3-(2,4-difluorophenyl)-4-(hydroxymethyl)-5-((trityloxy)methyl)tetrahydrofuran-3-yl)carbamothioyl)benzamide and the crude product from the two experiments was combined for purification by column chromatography (normal phase, 100 g, Biotage SNAP cartridge KP-Sil, 50 mL per min, gradient 5% to 20% to 30% EtOAc in n-hexane) to give the title compound. (3.99 g). $^1$H NMR (400 MHz, MeOH-d$_4$) δ ppm: 2.71 (dd, J=13.76, 3.97 Hz, 1 H) 3.02-3.17 (m, 1 H) 3.19-3.28 (m, 1 H) 3.31-3.35 (m, 1 H) 3.40 (dd, J=10.27, 4.28 Hz, 1 H) 4.00-4.07 (m, 1 H) 4.38-4.47 (m, 1 H) 4.54 (d, J=9.17 Hz, 1 H) 6.96-7.13 (m, 2 H) 7.17-7.39 (m, 9 H) 7.42-7.58 (m, 10 H) 8.03 (br. s., 2 H).

Step 6: N-((4aS,5S,7aS)-7a-(2,4-Difluorophenyl)-5-(hydroxymethyl)-4a,5,7,7a-tetrahydro-4H-furo[3,4-d][1,3]thiazin-2-yl)benzamide

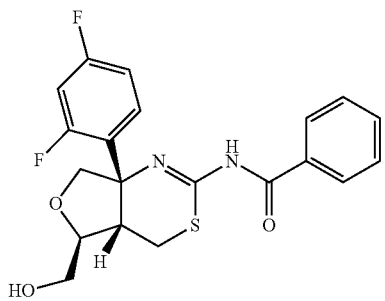 [SMILES: O=C(NC1=N[C@@]2(c3ccc(F)cc3F)CO[C@H](CO)[C@H]2CS1)c1ccccc1]

N-((4aS,5S,7aS)-7a-(2,4-Difluorophenyl)-5-((trityloxy)methyl)-4a,5,7,7a-tetrahydro-4H-furo[3,4-d][1,3]thiazin-2-yl)benzamide (3.99 g, 6.169 mmol) was taken up in formic acid (12 mL) at RT. The mixture was stirred at RT for 2.5 hours, then water (12 mL) was added. The mixture was stirred for 10 minutes and then filtered—washing with formic acid/water (1:1, 20 mL). The filtrate was evaporated and the residue was azeotroped with toluene (×2). The residue was taken up in dry MeOH (20 mL) and treated with potassium carbonate (1.0 g, 7.2 mmol). The mixture was stirred at RT for 30 minutes. The volatiles were removed in vacuo and the residue was partitioned between DCM and water. The layers were separated and the aqueous layer was further extracted with DCM (×4). The combined extracts were dried (Na$_2$SO$_4$), filtered and evaporated. The residue was purified by column chromatography (normal phase, 50 g, Biotage SNAP cartridge KP-Sil, 50 mL per min, gradient 40% to 90% EtOAc in n-hexane) to give the title compound (2.23 g). $^1$H NMR (400 MHz, MeOH-d$_4$) δ ppm: 2.85-3.05 (m, 1 H) 3.10-3.27 (m, 2 H) 3.68-3.80 (m, 2 H) 4.02 (br. d, J=7.90 Hz, 1 H) 4.36-4.43 (m, 1 H) 4.47 (d, J=9.16 Hz, 1 H) 6.95-7.13 (m, 2 H) 7.39-7.50 (m, 2 H) 7.50-7.60 (m, 2 H) 7.96-8.16 (m, 2 H)

Step 7: N-((4aS,5S,7aS)-7a-(2,4-Difluorophenyl)-5-(fluoromethyl)-4a,5,7,7a-tetrahydro-4H-furo[3,4-d][1,3]thiazin-2-yl)benzamide

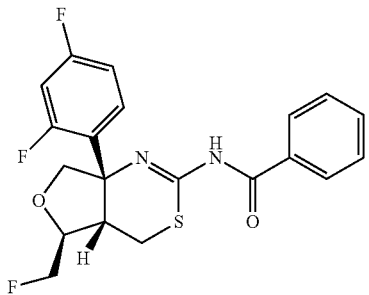 [SMILES: O=C(NC1=N[C@@]2(c3ccc(F)cc3F)CO[C@H](CF)[C@H]2CS1)c1ccccc1]

A solution of N-((4aS,5S,7aS)-7a-(2,4-difluorophenyl)-5-(hydroxymethyl)-4a,5,7,7a-tetrahydro-4H-furo[3,4-d][1,3]thiazin-2-yl)benzamide (2.2 g, 5.44 mmol) in dry THF (40 mL) under nitrogen was cooled to 0° C. Triethylamine (4.55 mL, 32.6 mmol), triethylamine tri-hydrogen fluoride (1.77 mL, 10.9 mmol) and nonafluorobutanesulfonyl fluoride (1.95 mL, 10.9 mmol) were then added. The colourless solution was stirred at 0° C. for 10 minutes and then removed from the ice bath. After 120 minutes at RT, the reaction was quenched with saturated aqueous NaHCO$_3$ (25 mL). The THF was removed in vacuo and then the mixture was partitioned between EtOAc and water. The layers were separated and the aqueous layer was further extracted with EtOAc (×2). The combined extracts were washed with brine (×1), then dried (Na$_2$SO$_4$), filtered and evaporated. The residue was treated with DCM (~20 mL) to give a gelatinous precipitate. This mixture was filtered (washing with DCM). The filtrate was concentrated to ~3 mL and loaded directly on to the column and purified by chromatography (normal phase, 50 g, Biotage SNAP cartridge KP-Sil, 50 mL per mm, gradient 5% to 35% n-hexane in EtOAc) to give the title compound (1.45 g). $^1$H NMR (400 MHz, MeOH-d$_4$) δ ppm: 2.97 (br. d, J=13.00 Hz, 1 H) 3.10-3.28 (m, 2 H) 4.02 (br. s., 1 H) 4.45-4.61 (m, 3 H) 4.62-4.71 (m, 1 H) 6.98-7.12 (m, 2 H) 7.40-7.51 (m, 2 H) 7.51-7.62 (m, 2 H) 8.03 (br. s., 2 H).

Step 8: (4aS,5S,7aS)-7a-(2,4-Difluorophenyl)-5-(fluoromethyl)-4a,5,7,7a-tetrahydro-4H-furo[3,4-d][1,3]thiazin-2-amine

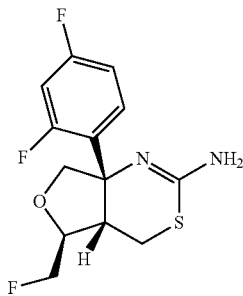 [SMILES: NC1=N[C@@]2(c3ccc(F)cc3F)CO[C@H](CF)[C@H]2CS1]

1,8-Diazabicyclo[5.4.0]undec-7-ene (0.99 mL, 6.6 mmol) was added to a stirred suspension of N-((4aS,5S,7aS)-7a-(2,4-difluorophenyl)-5-(fluoromethyl)-4a,5,7,7a-tetrahydro-4H-furo[3,4-d][1,3]thiazin-2-yl)benzamide (1.34 g, 3.30 mmol) in dry MeOH (10 mL) at RT under nitrogen. The reaction was stirred and heated at 65° C. overnight, under nitrogen. The reaction was allowed to cool to RT and the volatiles were removed in vacuo. The residue was purified by column chromatography (normal phase, 25 g, Biotage SNAP cartridge KP-Sil, 25 mL per min, gradient 20% to 100% EtOAc in n-hexane) to give the title compound (1.04 g). $^1$H NMR (400 MHz, CDCl$_3$) δ ppm: 2.78 (dd, J=13.33, 4.03 Hz, 1 H) 2.93-3.01 (m, 1 H) 3.09 (dd, J=13.39, 3.61 Hz, 1 H) 3.83 (dd, J=8.44, 2.45 Hz, 1 H) 4.44-4.56 (m, 3 H) 4.62 (d, J=4.40 Hz, 1 H) 6.75-6.92 (m, 2 H) 7.36-7.47 (m, 1 H).

Step 9: (4aS,5S,7aS)-7a-(5-bromo-2,4-difluorophenyl)-5-(fluoromethyl)-4a,5,7,7a-tetrahydro-4H-furo[3,4-d][1,3]thiazin-2-amine

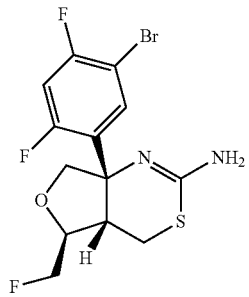 [SMILES: NC1=N[C@@]2(c3cc(Br)c(F)cc3F)CO[C@H](CF)[C@H]2CS1]

(4aS,5S,7aS)-7a-(2,4-Difluorophenyl)-5-(fluoromethyl)-4a,5,7,7a-tetrahydro-4H-furo[3,4-d][1,3]thiazin-2-amine (700 mg, 2.32 mmol) was dissolved in TFA (2.1 mL) and sulfuric acid (864 μL, 16.2 mmol). NBS (453 mg, 2.55 mmol) was added and the reaction was stirred at 60° C. for 45 minutes. The reaction was cooled to room temperature and basified with 2N NaOH. The mixture was then extracted with EtOAc (×3). The combined organics were dried (MgSO$_4$) and concentrated in vacuo. The residue was purified using column chromatography, eluting with 20-80% EtOAc in n-hexane to give the title compound. (620 mg). $^1$H NMR (400 MHz, CDCl$_3$) δ ppm: 7.67 (t, J=8.13 Hz, 1H), 6.94 (dd, J=8.01, 11.55 Hz, 1H), 4.65 (d, J=4.16 Hz, 1H), 4.47-4.57 (m, 3H), 3.84-3.98 (m, 1H), 3.01-3.20 (m, 2H), 2.77-2.91 (m, J=13.40 Hz, 1H).

Step 10: tert-Butyl ((4aS,5S,7aS)-7a-(5-bromo-2,4-difluorophenyl)-5-(fluoromethyl)-4a,5,7,7a-tetrahydro-4H-furo[3,4-d][1,3]thiazin-2-yl)carbamate

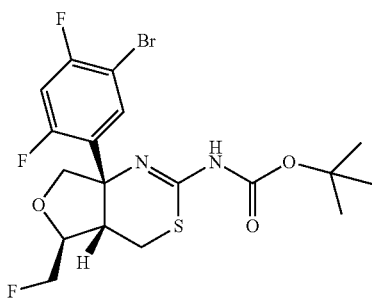 [SMILES: CC(C)(C)OC(=O)NC1=N[C@@]2(c3cc(Br)c(F)cc3F)CO[C@H](CF)[C@H]2CS1]

(4aS,5S,7aS)-7a-(5-Bromo-2,4-difluorophenyl)-5-(fluoromethyl)-4a,5,7,7a-tetrahydro-4H-furo[3,4-d][1,3]thiazin-2-amine (620 mg, 1.63 mmol) was dissolved in THF (10 mL). (BOC)$_2$O (0.45 mL, 1.95 mmol) and Et$_3$N (0.27 mL, 1.95 mmol) were added and the reaction was stirred at 100° C. After 1 hour, the solvents were removed in vacuo. The residue was purified using column chromatography (Biotage SNAP 25 g, 20 mL/min eluting with 20-80% EtOAc in n-hexane) to leave the title compound as a foam. (704 mg). $^1$H NMR (400 MHz, CDCl$_3$) δ ppm: 7.54 (t, J=1.00 Hz, 1H), 6.86-7.01 (m, 1H), 4.49-4.71 (m, 3H), 4.45 (dd, J=1.22, 8.56 Hz, 1H), 3.68-3.92 (m, 1H), 2.95-3.20 (m, 2H), 2.73 (t, J=1.00 Hz, 1H), 1.46-1.64 (m, 9H)

Step 11: (4aS,5S,7aS)-7a-(2,4-difluoro-5-(pyrimidin-5-yl)phenyl)-5-(fluoromethyl)-4a,5,7,7a-tetrahydro-4H-furo[3,4-d][1,3]thiazin-2-amine

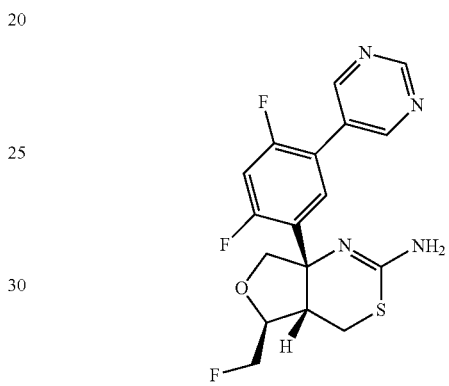

tert-Butyl ((4aS,5S,7aS)-7a-(5-bromo-2,4-difluorophenyl)-5-(fluoromethyl)-4a,5,7,7a-tetrahydro-4H-furo[3,4-d][1,3]thiazin-2-yl)carbamate (100 mg, 0.21 mmol) was dissolved in DME (1.5 mL), EtOH (0.7 mL) and water (0.5 mL). The solution was heated to 100° C. Pyrimidin-5-ylboronic acid (51.5 mg, 0.416 mmol), bis(triphenylphosphine)palladium (II) chloride (29.2 mg, 0.042 mmol) and cesium carbonate (406 mg, 1.25 mmol) were added and the reaction was stirred at 100° C. for 45 minutes. The reaction was cooled to room temperature and partitioned between DCM and saturated aqueous NaHCO$_3$. The layers were separated and the aqueous layer was extracted with DCM (×2). The organic layers were combined, dried (MgSO$_4$) and concentrated in vacuo. The residue was purified by column chromatography (Biotage SNAP 10 g, 12 mL/min eluting with 20-80% EtOAc in n-hexane). The material was stirred in DCM (2 mL, 31.08 mmol) and TFA (2 mL) for 1 hour at room temperature. The solvents were removed in vacuo. The residue was passed over a 5 g SCX cartridge, washing with MeOH then 2N NH$_3$/MeOH. The basic fractions were concentrated in vacuo and the residue was purified by column chromatography (Biotage SNAP 10 g, 12 mL/min gradient 0-20% MeOH in EtOAc) to leave the title compound as a white solid.

$^1$H NMR (400 MHz, CDCl$_3$) δ ppm: 9.24 (s, 1H), 8.93 (s, 2H), 7.59 (t, J=8.68 Hz, 1H), 7.03 (dd, J=9.78, 11.62 Hz, 1H), 4.65-4.69 (m, 1H), 4.48-4.61 (m, 3H), 3.89 (dd, J=1.83, 8.56 Hz, 1H), 3.11-3.16 (m, 1H), 3.08 (td, J=3.67, 7.58 Hz, 1H), 2.84 (dd, J=3.73, 13.27 Hz, 1H)

EXAMPLE 28

(4aS,5S,7aS)-7a-(2,4-difluoro-5-(2-fluoropyridin-3-yl)-5-(fluoromethyl)-4a,5,7,7a-tetrahydro-4H-furo[3,4-d][1,3]thiazin-2-amine

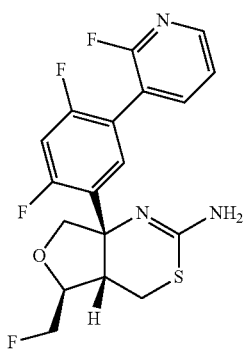 [SMILES: NC1=N[C@@]2(c3cc(-c4cccnc4F)c(F)cc3F)CO[C@H](CF)[C@H]2CS1]

The compound was prepared using the same method as that described in Example 27, replacing pyrimidin-5-ylboronic acid with the appropriate boronic acid.

$^1$H NMR (400 MHz, CDCl$_3$) δ ppm: 8.25-8.31 (m, 1H), 7.82-7.90 (m, 1H), 7.50 (t, J=8.56 Hz, 1H), 7.31 (ddd, J=1.71, 5.07, 7.15 Hz, 1H), 6.99 (dd, J=9.29, 11.86 Hz, 1H), 4.66 (d, J=4.28 Hz, 1H), 4.47-4.62 (m, 3H), 3.90-3.98 (m, 1H), 3.19 (dd, J=3.48, 13.39 Hz, 1H), 3.12 (td, J=3.59, 7.61 Hz, 1H), 2.85 (dd, J=3.91, 13.45 Hz, 1H)

EXAMPLE 29

(4aS,5S,7aS)-7a-(2,4-difluoro-5-(5-methoxypyridin-3-yl)phenyl)-5-(fluoromethyl)-4a,5,7,7a-tetrahydro-4H-furo[3,4-d][1,3]thiazin-2-amine

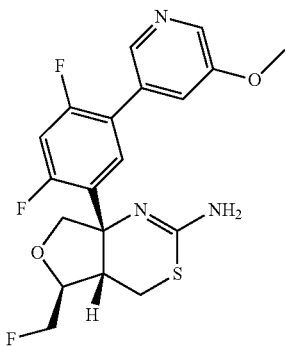 [SMILES: COc1cncc(-c2cc([C@]34CO[C@H](CF)[C@H]3CSC(N)=N4)c(F)cc2F)c1]

The compound was prepared using the same method as that described in Example 27, replacing pyrimidin-5-ylboronic acid with the appropriate boronic acid.

$^1$H NMR (400 MHz, CDCl$_3$) δ ppm: 8.36 (t, J=1.47 Hz, 1H), 8.31 (d, J=2.81 Hz, 1H), 7.55 (t, J=8.86 Hz, 1H), 7.35 (td, J=1.57, 2.84 Hz, 1H), 6.97 (dd, J=9.90, 11.74 Hz, 1H), 4.65 (d, J=4.16 Hz, 1H), 4.46-4.60 (m, 3H), 3.91 (s, 3H), 3.87 (dd, J=2.32, 8.56 Hz, 1H), 3.14 (dd, J=3.48, 13.39 Hz, 1H), 3.05 (td, J=3.79, 7.82 Hz, 1H), 2.81 (dd, J=3.91, 13.45 Hz, 1H)

EXAMPLE 30

(4aS,5S,7aS)-7a-(2,4-difluoro-5-(6-fluoropyridin-3-yl)phenyl)-5-(fluoromethyl)-4a,5,7,7a-tetrahydro-4H-furo[3,4-d][1,3]thiazin-2-amine

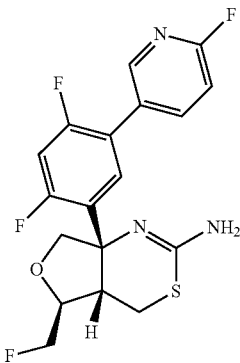 [SMILES: NC1=N[C@@]2(c3cc(-c4ccc(F)nc4)c(F)cc3F)CO[C@H](CF)[C@H]2CS1]

The compound was prepared using the same method as that described in Example 27, replacing pyrimidin-5-ylboronic acid with the appropriate boronic acid.

$^1$H NMR (400 MHz, CDCl$_3$) δ ppm: 8.36 (d, J=0.86 Hz, 1H), 7.90-7.99 (m, 1H), 7.52 (t, J=8.86 Hz, 1H), 6.94-7.05 (m, 2H), 4.66 (d, J=4.28 Hz, 1H), 4.48-4.59 (m, 3H), 3.87 (dd, J=2.20, 8.56 Hz, 1H), 3.14 (dd, J=3.55, 13.33 Hz, 1H), 3.06 (td, J=3.79, 7.83 Hz, 1H), 2.83 (dd, J=3.91, 13.45 Hz, 1H)

EXAMPLE 31

(4aS*,5R*,7aS*)-7a-(2,4-Difluoro-5-(pyrimidin-5-yl)phenyl)-5-methyl-4a,5,7,7a-tetrahydro-4H-furo[3,4-d][1,3]thiazin-2-amine

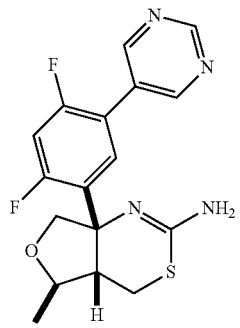 [SMILES: C[C@H]1OC[C@]2(c3cc(-c4cncnc4)c(F)cc3F)N=C(N)SC[C@H]12]

Step 1: (±)-1-(5-Bromo-2,4-difluorophenyl)-2-(but-3-en-2-yloxy)ethanone

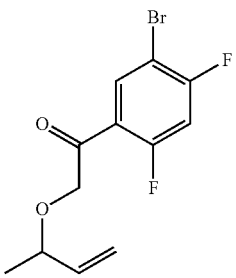 [SMILES: C=CC(C)OCC(=O)c1cc(Br)c(F)cc1F]

1,5-Dibromo-2,4-difluorobenzene (1.16 g, 4.28 mmol) was dissolved in Et$_2$O (2 mL) and the solution was cooled to −78° C. $^n$BuLi (1.26 mL 2.5M solution in hexanes) was added dropwise, maintaining the internal temperature below −70° C. Immediately after addition of "BuLi is complete, a solution of (±)-2-(but-3-en-2-yloxy)-N-methoxy-N-methylacetamide (0.5 g, 2.85 mmol) in Et₂O (2 mL) was added dropwise, keeping the internal temperature below −70° C. The reaction was stirred at −78° C. for 15 minutes before quenching with saturated NH₄Cl. The mixture was extracted with DCM (×3), dried (MgSO₄) and concentrated in vacuo. The reaction was repeated a further 5 times on the same scale. The residues from all six reactions were combined and purified by column chromatography (Biotage SNAP 25 g 0-10% EtOAc in hexane) to leave the desired compound as a yellow oil (2 g). ¹H NMR (400 MHz, CDCl₃) δ ppm: 8.20 (t, J=7.46 Hz, 1H), 6.98 (dd, J=7.95, 10.15 Hz, 1H), 5.76 (ddd, J=7.70, 10.09, 17.42 Hz, 1H), 5.16-5.26 (m, 2H), 4.51-4.69 (m, 2H), 3.93-4.04 (m, 1H), 1.34-1.40 (m, 3H)

Step 2: (±)-(E/Z)-1-(5-Bromo-2,4-difluorophenyl)-2-(but-3-en-2-yloxy)ethanone oxime

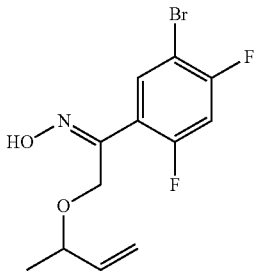 [SMILES: C=CC(C)OC/C(=N\O)c1cc(Br)c(F)cc1F]

(±)-1-(5-Bromo-2,4-difluorophenyl)-2-(but-3-en-2-yloxy)ethanone (2 g, 6.55 mmol) was dissolved in methanol (10 mL). Hydroxylamine hydrochloride (0.59 g, 8.52 mmol) and sodium acetate (0.81 g, 9.83 mmol) were added and the milky solution was stirred at 50° C. for 2 hours. The reaction was filtered, washing with EtOAc. The filtrate was transferred to a separating funnel and the layers were separated. The aqueous layer was extracted with EtOAc (×3). The combined organics were dried (MgSO₄) and purified using column chromatography, eluting with 0-25% EtOAc in n-hexane to leave the title compound as a clear oil. (1.1 g). ¹H NMR (400 MHz, CDCl₃) δ ppm: 7.91 (br. s., 1H), 7.69 (t, J=7.52 Hz, 1H), 6.93 (dd, J=8.44, 9.78 Hz, 1H), 5.57-5.73 (m, 1H), 5.09-5.23 (m, 2H), 4.57-4.66 (m, 2H), 3.78 (quin, J=6.54 Hz, 1H), 1.13 (d, J=6.36 Hz, 3H)

Step 3: (3aR*,4R*,6aS*)-6a-(5-Bromo-2,4-difluorophenyl)-4-methylhexahydro furo[3,4-c]isoxazole

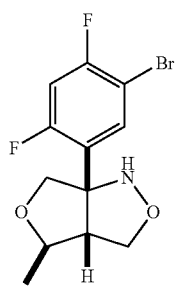

(±)-(E/Z)-1-(5-Bromo-2,4-difluorophenyl)-2-(but-3-en-2-yloxy)ethanone oxime (1.1 g, 3.46 mmol) was dissolved in xylene (20 mL). Benzene-1,4-diol (0.068 g, 0.62 mmol) was added and the reaction was stirred at 150° C. for 3 hours. The reaction mixture was concentrated in vacuo. EtOAc was added and the material was reconcentrated (×2). The residue was dissolved in DCM and purified using column chromatography, eluting with 0-30% EtOAc in n-hexane to leave the title compound. (700 mg).

Step 4: ((2R*,3R*,4S*)-4-Amino-4-(2,4-difluorophenyl)-2-methyltetrahydrofuran-3-yl)methanol

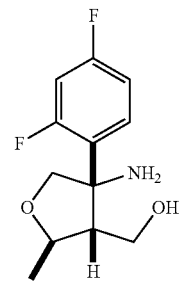

(3aR*,4R*,6aS*)-6a-(5-Bromo-2,4-difluorophenyl)-4-methylhexahydro furo[3,4-c]isoxazole (200 mg, 0.62 mmol) was dissolved in THF (10 mL). Zinc dust (0.49 g, 7.50 mmol) was added, followed by acetic acid (143 µl, 2.50 mmol) and the reaction was stirred at room temperature overnight. The reaction was filtered through Celite®, washing with MeOH and the filtrate was concentrated in vacuo. The residue was basified with saturated NaHCO₃ and DCM added. The mixture was filtered and the layers separated. The aqueous layer was extracted with DCM (×2) and the combined organics were dried (MgSO₄) and concentrated to leave the title compound (120 mg).
¹H NMR (400 MHz, CDCl₃) δ ppm: 7.41 (dt, J=6.36, 8.99 Hz, 1H), 6.66-6.92 (m, 2H), 4.13-4.30 (m, 2H), 3.94 (dd, J=3.55, 11.98 Hz, 1H), 3.60-3.81 (m, 2H), 2.04-2.20 (m, 1H), 1.39-1.74 (m, 2H), 1.24 (d, J=6.11 Hz, 3H)

Step 5: N-(((3S*,4R*,5R*)-3-(2,4-Difluorophenyl)-4-(hydroxymethyl)-5-methyltetrahydrofuran-3-yl)carbamothioyl)benzamide

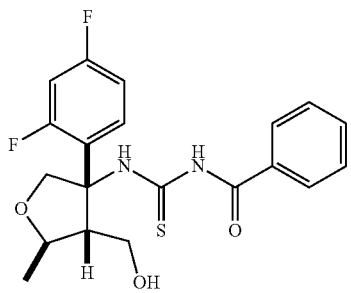

((2R*,3R*,4S*)-4-Amino-4-(2,4-difluorophenyl)-2-methyltetrahydrofuran-3-yl)methanol (120 mg, 0.49 mmol) was dissolved in DCM (2 mL). Benzoyl isothiocyanate (66 µl, 0.49 mmol) was added and the reaction was stirred at room temperature for 30 minutes. The reaction mixture was concentrated in vacuo and purified by column chromatography, eluting with 0-30% EtOAc in n-hexane to leave the title compound as a yellow oil (165 mg). ¹H NMR (400 MHz, CDCl₃) δ ppm: 11.81 (s, 1H), 8.89 (s, 1H), 7.84-7.91 (m, 2H), 7.62-7.75 (m, 2H), 7.49-7.58 (m, 2H), 6.91 (dt, J=1.71, 8.38

Hz, 1H), 6.80 (ddd, J=2.63, 8.80, 11.80 Hz, 1H), 4.69 (d, J=10.15 Hz, 1H), 4.39 (dd, J=1.71, 10.15 Hz, 1H), 3.91-4.08 (m, 3H), 2.85 (dd, J=4.58, 6.79 Hz, 1H), 2.59 (dt, J=3.73, 8.10 Hz, 1H), 1.37 (d, J=5.99 Hz, 3H).

Step 6: N-((4aS*,5R*,7aS*)-7a-(2,4-Difluorophenyl)-5-methyl-4a,5,7,7a-tetrahydro-4H-furo[3,4-d][1,3]thiazin-2-yl)benzamide

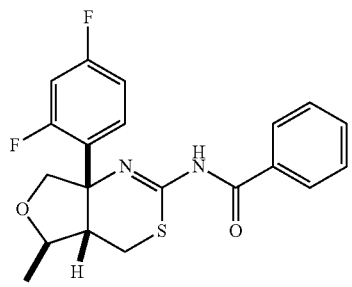

N-(((3S*,4R*,5R*)-3-(2,4-Difluorophenyl)-4-(hydroxymethyl)-5-methyltetrahydrofuran-3-yl)carbamothioyl)benzamide (165 mg, 0.41 mmol) was dissolved in pyridine (2 mL) and the solution was cooled to −20° C. Trifluoromethanesulfonic acid anhydride (68 µl, 0.41 mmol) was added dropwise into the reaction. After 45 minutes, the reaction was incomplete so a further aliquot of trifluoromethanesulfonic acid anhydride (68 µl, 0.41 mmol) was added and the reaction stirred for a further 1 hour. The reaction was quenched with saturated NaHCO₃ and extracted with Et₂O (×2). The combined organics were concentrated and the residue purified by column chromatography, eluting with 0-30% EtOAc in n-hexane to leave the title compound as a yellow foam. (95 mg). ¹H NMR (400 MHz, CDCl₃) δ ppm: 8.11-8.17 (m, 2H), 7.38-7.62 (m, 4H), 6.86-7.02 (m, 2H), 4.47-4.58 (m, 2H), 4.01 (dd, J=2.63, 9.48 Hz, 1H), 3.17-3.26 (m, 1H), 2.75-2.86 (m, 2H), 1.42 (d, J=6.11 Hz, 3H).

Step 7: N-((4aS*,5R*,7aS*)-7a-(5-Bromo-2,4-difluorophenyl)-5-methyl-4a,5,7,7a-tetrahydro-4H-furo[3,4-d][1,3]thiazin-2-yl)benzamide

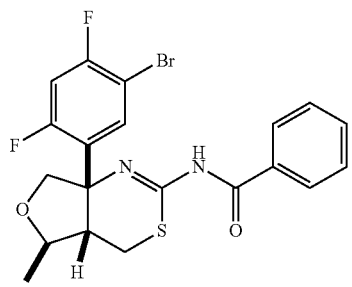

N-((4aS*,5R*,7aS*)-7a-(2,4-Difluorophenyl)-5-methyl-4a,5,7,7a-tetrahydro-4H-furo[3,4-d][1,3]thiazin-2-yl)benzamide (95 mg, 0.24 mmol) was dissolved in TFA (218 µL, 2.93 mmol) and sulfuric acid (78.2 µl, 1.47 mmol). NBS (39 mg, 0.22 mmol) was added and the reaction was stirred at 60° C. for 1 hour. The reaction mixture was cooled to room temperature, neutralized with 2N NaOH and extracted with EtOAc (×3). The combined organics were dried and concentrated in vacuo. The residue was purified by column chromatography, eluting with 0-30% EtOAc in n-hexane to give the desired compound. (78 mg). ¹H NMR (400 MHz, CDCl₃) δ ppm: 8.05-8.10 (m, 2H), 7.52-7.62 (m, 2H), 7.44-7.51 (m, 2H), 6.95-7.04 (m, 1H), 4.46-4.53 (m, 2H), 3.95 (dd, J=2.45, 9.41 Hz, 1H), 3.17 (dd, J=3.42, 13.45 Hz, 1H), 2.77-2.83 (m, 1H), 2.70-2.77 (m, 1H), 1.37-1.46 (m, 3H).

Step 8: (4aS*,5R*,7aS*)-7a-(2,4-Difluoro-5-(pyrimidine-5-yl)phenyl)-5-methyl-4a 5,7,7a-tetrahydro-4H-furo[3,4-d][1,3]thiazin-2-amine

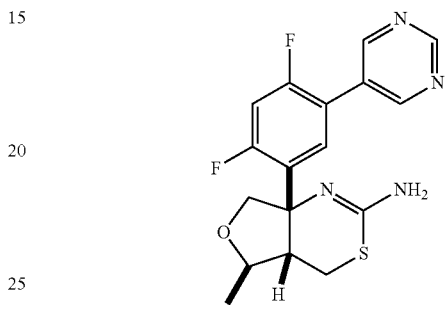

N-((4aS*,5R*,7aS*)-7a-(5-Bromo-2,4-difluorophenyl)-5-methyl-4a,5,7,7a-tetrahydro-4H-furo[3,4-d][1,3]thiazin-2-yl)benzamide (57 mg, 0.12 mmol) was dissolved in DME (1.5 mL), H₂O (0.7 mL) and EtOH (0.5 mL). The solution was heated to 100° C. Pyrimidine-5-yl boronic acid (91 mg, 0.73 mmol) was added, followed by Cs₂CO₃ (0.24 g, 0.73 mmol) and bis(triphenylphosphine)palladium(II) chloride (26 mg, 0.037 mmol) were added and the reaction was stirred at 100° C. for 45 minutes. The reaction was cooled to room temperature and partitioned between DCM and saturated NaHCO₃. The layers were separated and the aqueous layer was extracted with EtOAc (×3). The organic layers were combined, dried (MgSO₄) and concentrated in vacuo. The residue was purified by column chromatography, Biotage SNAP 10 g, 12 mL/min eluting with 0-30% EtOAc in n-hexane.

The benzoyl group was removed in an analogous manner to the procedure described in Example 27 (Step 8) to give the title compound. ¹H NMR (400 MHz, MeOH-d₄) δ ppm: 9.19 (s, 1H), 8.99 (d, J=1.10 Hz, 2H), 7.64 (t, J=8.68 Hz, 1H), 7.27 (dd, J=10.27, 11.74 Hz, 1H), 4.60 (d, J=9.29 Hz, 1H), 4.29-4.38 (m, 1H), 3.87 (dd, 0.1=2.08, 9.05 Hz, 1H), 3.19 (dd, J=4.16, 13.57 Hz, 1H), 2.97 (dd, J=4.52, 13.57 Hz, 1H), 2.62-2.69 (m, 1H), 1.35 (d, J=6.11 Hz, 3H).

Pharmacological Analysis

In vitro Cellular Assay (Aβ42):

Quantification of AβPeptide in Culture of Neurons from Rat Fetus Brain (1) Rat Primary Neuronal Culture Primary neuronal cultures were prepared from the cerebral cortex of embryonic day 18 Wistar rats (Charles River, UK). Specifically, the embryos were aseptically removed from pregnant rats under ether anesthesia. The brain was isolated from the embryo and immersed in HBSS (Sigma Aldrich #H9269) containing 10 mM HEPES (Gibco #15630-056). The cerebral cortex was collected from the isolated brain under a stereoscopic microscope. The cerebral cortex fragments collected were enzymatically treated in an enzyme solution containing 0.05% trypsin-EDTA solution (GIBCO, #25300) at 37° C. for 20 minutes to disperse the cells. The cells were then washed twice and then gently resuspended in Neurobasal medium (Gibco #21103) supplemented with 2% B27 supplement (GIBCO #17504-044), 0.5 mM L-glutamine (GIBCO #25030), 1×N2 (GIBCO #17502-048), 100 ug/ml Pen/Strep (GIBCO 15140-122) and 5% heat inactivated FCS (PAA #A15-701). The cell dispersion was filtered through a 40-μm nylon mesh (BD Falcon #352340) to remove the remaining cell mass, and thus a neuronal cell suspension was obtained. The neuronal cell suspension was diluted with the medium above and then plated in a volume of 100 μL/well at an initial cell density of $3.25 \times 10^5$ cells/ml in poly-D-lysine coated 96-well culture plate (Greiner #655940). The plated cells were cultured in the culture plate at 37° C. in 5% $CO_2$-95% air for 24 hrs. The total amount of the medium was replaced with 'assay Neurobasal medium' (as above excluding heat inactivated FCS), and then the cells were cultured for a further five days.

(2) Addition of Compound

The drug was added to the culture plate on Day 6 of culture as follows. 8 point compound serial dilutions were generated in DMSO at a concentration of ×1000 that of the final assay concentration (FAC). Compound solutions were then prepared by adding 999 ul of 'Assay Neurobasal media' (as described in above section) to 1 ul of DMSO compound stock. The total amount of the medium was removed from each of the cell plate wells, and 200 μL/well of compound solution was added. The final DMSO concentration was 0.1%.

(3) Sampling

The cells were cultured for either 1 or 3 days after addition of the compound for ABx-40 and ABx-42 assays respectively. 150 μl of sample medium was collected and used as the ELISA sample.

(4) Evaluation of Cell Survival

Cell survival was evaluated using an Alamar assay according to the following procedure. After collecting the sample to be used in the ELISA assay, 50 μl of 20% Alamar blue solution (Invitrogen #DAL1100) in assay Neurobasal media, was added to 50 μl of remaining sample within each well. Cells were then incubated at 37° C. in 5% $CO_2$-95% air for 1 hr.

Measurement of fluorescence intensity for each well was the carried out at 540/590 nm using a Pherastar plus plate reader (BMG labtech). Upon measurement, wells having no cells plated and containing only the medium and Alamar solution were set as background (bkg).

(5) Aβ ELISA

Human/Rat β Amyloid (42) ELISA Kit Wako (#290-62601) and Human/Rat β Amyloid (40) ELISA Kit Wako (#294-62501) from Wako Pure Chemical Industries, Ltd. were used for Aβ ELISA Aβ ELISA was carried out according to the protocols recommended by the manufacturers, described in the documents accompanying the kits. The results were shown as percentage of the control groups and IC50 values for each compound were determined using four parameter logistic fit model using the XLFIT5 software package (IDBS).

The compounds of the present invention have an Aβ42 production reducing effect.

The compound of the general formula (I) or pharmaceutically acceptable salt thereof according to the present invention has an Aβ42 production reducing effect. Thus, the present invention can particularly provide a prophylactic or therapeutic agent for a neurodegenerative disease caused by Aβ such as Alzheimer-type dementia or Down's syndrome.

As measured by the above in vitro assay, compound Examples 1 to 30 showed $IC_{50}$ values as displayed in Table 1:

Table of Activities (Table 1)

| Example No. | Cell $IC_{50}$ (μM) |
|---|---|
| 1 | 0.065 |
| 2 | 0.749 |
| 3 | 0.069 |
| 4 | 0.106 |
| 5 | 0.450 |
| 6 | 0.244 |
| 7 | 0.062 |
| 8 | 0.023 |
| 9 | 0.060 |
| 10 | 0.094 |
| 11 | 0.839 |
| 12 | 0.114 |
| 13 | 0.062 |
| 14 | 0.136 |
| 15 | 0.101 |
| 16 | 0.058 |
| 17 | 0.977 |
| 18 | 0.217 |
| 19 | 0.017 |
| 20 | >1 |
| 21 | 0.127 |
| 22 | 0.055 |
| 23 | 0.572 |
| 24 | >1 |
| 25 | 0.342 |
| 26 | 0.064 |
| 27 | 0.059 |
| 28 | 0.046 |
| 29 | 0.015 |
| 30 | 0.223 |
| 31 | 0.020 |

Human Liver Microsomal Stability Assay

The following experimental protocol is a prophetic method with which the Human Liver microsomal stability of the presently claimed compounds of formula (I) might be evaluated.

The compound is dissolved in DMSO to prepare 1 mmol/L DMSO solution. The DMSO solution is diluted with distilled water to prepare 1 μmol/L compound dosing solution (DMSO conc.: 0.1%).

105 μL of reaction buffer (1 mol/L phosphate buffer (pH 7.4)/1 mmol/L EDTA (pH 7.4)/distilled water=1/1/5, v/v/v), 15 μL of 1 μmol/L compound dosing solution, and 15 μL of rat or human liver microsomes (5 mg/mL) is mixed, and preincubated for 5 min at 37° C. Metabolic reaction is initiated by adding 15 μL of NADPH generating system (3.3 mmol/L β-NADPH+, 80 mmol/L glucose 6-phosphate, 1 unit/mL glucose 6-phosphate dehydrogenase, 60 mmol/L $MgCl_2$). For the control sample, NADPH generating system is replaced with 60 mmol $MgCl_2$. The 150 μL of reaction mixture (final compound conc.: 0.1 μmol/L, final DMSO conc.: 0.01%) is incubated for 30 min at 37° C., and the reaction terminated by adding 150 μL of methanol/acetonitrile solution containing an appropriate internal standard compound. The sample is vertexed and centrifuged, and obtained supernatant is subject to LC/MS analysis.

The invention claimed is:
1. A compound of formula (Ib):

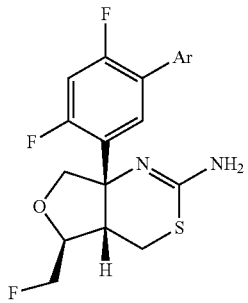

or a pharmaceutically acceptable salt thereof,
wherein Ar is phenyl or a 5- or 6-membered heteroaromatic group containing 1, 2 or 3 N atoms, which Ar is optionally substituted by one to three substituents selected from hal, hydroxyl, —CN, $C_{1-6}$alkyl, $C_{2-3}$alkenyl, $C_{2-3}$alkynyl, $C_{1-6}$alkoxy, $C_{3-6}$cycloalkoxy and pyrazine, where $C_{1-6}$alkyl and $C_{1-6}$alkoxy are optionally substituted by one to three halogen atoms.

2. A compound is selected from the group consisting of:
(4aS,5S,7aS)-7a-(2,4-Difluoro-5-(pyrimidin-5-yl)phenyl)-5-(fluoromethyl)-4a,5,7,7a-tetrahydro-4H-furo[3,4-d][1,3]thiazin-2-amine,
(4aS,5S,7aS)-7a-(2,4-difluoro-5-(2-fluoropyridin-3-yl)phenyl)-5-(fluoromethyl)-4a,5,7,7a-tetrahydro-4H-furo[3,4-d][1,3]thiazin-2-amine,
(4aS,5S,7aS)-7a-(2,4-difluoro-5-(5-methoxypyridin-3-yl)phenyl)-5-(fluoromethyl)-4a,5,7,7a-tetrahydro-4H-furo[3,4-d][1,3]thiazin-2-amine, and,
(4aS,5S,7aS)-7a-(2,4-difluoro-5-(6-fluoropyridin-3-yl)phenyl)-5-(fluoromethyl)-4a,5,7,7a-tetrahydro-4H-furo[3,4-d][1,3]thiazin-2-amine
or a pharmaceutically acceptable salt thereof.

3. A pharmaceutical composition comprising the compound or pharmaceutically acceptable salt thereof according to claim 1, as an active ingredient in association with a pharmaceutically acceptable carrier.

4. The compound or pharmaceutically acceptable salt thereof according to claim 1, wherein Ar is pyridinyl or pyrimidinyl, which Ar is optionally substituted by one or two substituents selected from fluorine, $C_{1-2}$alkyl and $C_{1-2}$alkoxy.

5. A compound which is (4aS,5S,7aS)-7a-(2,4-difluoro-5-(pyrimidin-5-yl)phenyl)-5-(fluoromethyl)-4a,5,7,7a-tetrahydro-4H-furo [3,4-d][1,3]thiazin-2-amine, or a pharmaceutically acceptable salt thereof.

6. A pharmaceutical composition comprising the compound or pharmaceutically acceptable salt thereof according to claim 2, as an active ingredient in association with a pharmaceutically acceptable carrier.

7. A pharmaceutical composition comprising the compound or pharmaceutically acceptable salt thereof according to claim 5, as an active ingredient in association with a pharmaceutically acceptable carrier.

8. A method of treating Down's syndrome, comprising administering to a human subject with Down's syndrome an effective amount of the compound or pharmaceutically acceptable salt thereof according to claim 1.

9. A method of treating Down's syndrome, comprising administering to a human subject with Down's syndrome an effective amount of the compound or pharmaceutically acceptable salt thereof according to claim 2.

10. A method of treating Down's syndrome, comprising administering to a human subject with Down's syndrome an effective amount of the compound or pharmaceutically acceptable salt thereof according to claim 5.

11. A method of treating Alzheimer-type dementia, comprising administering to a human subject suffering from Alzheimer-type dementia an effective amount of the compound or pharmaceutically acceptable salt thereof according to claim 1.

12. A method of treating Alzheimer-type dementia, comprising administering to a human subject suffering from Alzheimer-type dementia an effective amount of the compound or pharmaceutically acceptable salt thereof according to claim 2.

13. A method of treating Alzheimer-type dementia, comprising administering to a human subject suffering from Alzheimer-type dementia an effective amount of the compound or pharmaceutically acceptable salt thereof according to claim 5.

* * * * *